United States Patent
McConnell et al.

(10) Patent No.: US 8,895,581 B2
(45) Date of Patent: Nov. 25, 2014

(54) 1*H*-IMIDAZO[4,5-*C*]QUINOLINES

(75) Inventors: Darryl McConnell, Vienna (AT); Harald Engelhardt, Ebreichsdorf (AT); Christiane Kofink, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/697,034

(22) PCT Filed: May 17, 2011

(86) PCT No.: PCT/EP2011/057985
§ 371 (c)(1),
(2), (4) Date: Jan. 22, 2013

(87) PCT Pub. No.: WO2011/144622
PCT Pub. Date: Nov. 24, 2011

(65) Prior Publication Data
US 2013/0210832 A1    Aug. 15, 2013

(30) Foreign Application Priority Data
May 17, 2010   (EP) .................................... 10163019

(51) Int. Cl.
  *A61K 31/437*   (2006.01)
  *C07D 471/04*   (2006.01)
  *A61K 31/501*   (2006.01)
  *A61K 45/06*    (2006.01)
  *A61K 31/444*   (2006.01)
  *A61K 31/513*   (2006.01)
  *A61K 31/4545*  (2006.01)

(52) U.S. Cl.
  CPC ............ *C07D 471/04* (2013.01); *A61K 31/501* (2013.01); *A61K 45/06* (2013.01); *A61K 31/444* (2013.01); *A61K 31/513* (2013.01); *A61K 31/4545* (2013.01)
  USPC ............... 514/293; 546/79; 546/82; 514/279; 514/290

(58) Field of Classification Search
  CPC .......................... C07D 471/04; A61K 31/437
  USPC ................ 546/79, 81, 82; 514/279, 290, 293
  See application file for complete search history.

(56) References Cited

U.S. PATENT DOCUMENTS 8,575,203 B2 * 11/2013 Engelhardt et al. ........... 514/354
8,637,549 B2 *  1/2014 Engelhardt et al. ........... 514/333

FOREIGN PATENT DOCUMENTS

| WO | 2005054238 A1 | 6/2005 |
| WO | 2007075468 A1 | 7/2007 |
| WO | 2008005457 A2 | 1/2008 |
| WO | 2010007114 A2 | 1/2010 |
| WO | 2010007116 A2 | 1/2010 |
| WO | 2011144622 A1 | 11/2011 |

OTHER PUBLICATIONS

International Search Report and Written Opinion for PCT/EP2011/057986 mailed Nov. 16, 2011.

* cited by examiner

*Primary Examiner* — Golam M M Shameem
(74) *Attorney, Agent, or Firm* — Michael P. Morris; Anthony P. Bottino; Alan R. Stempel

(57) ABSTRACT

The present invention encompasses compounds of general formula (1), wherein the groups $R^1$ to $R^7$, $Q^a$, $Q^b$, L, n and m are defined as in claim 1, which are suitable for the treatment of diseases characterized by excessive or abnormal cell proliferation, pharmaceutical preparations containing such compounds and their use as medicaments.

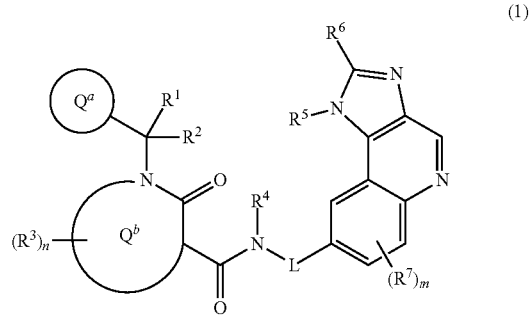

18 Claims, No Drawings

1H-IMIDAZO[4,5-C]QUINOLINES

The present invention relates to new 1H-imidazo[4,5-c]quinolines of general formula (1)

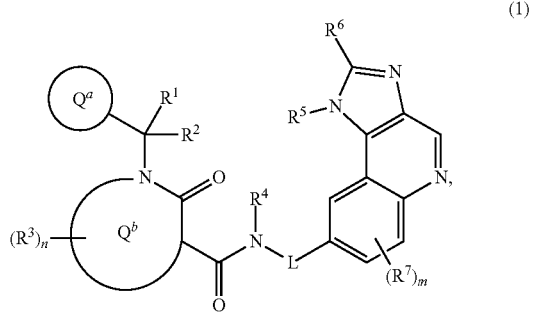

wherein the groups $R^1$ to $R^7$, $Q^a$, $Q^b$, L, m and n have the meanings given in the claims and specification, which are suitable for the treatment of diseases characterised by excessive or abnormal cell proliferation, pharmaceutical preparations containing such compounds and their use as medicaments. The compounds according to the invention exhibit an inhibitory effect on the serine/threonine kinase PDK 1

BACKGROUND TO THE INVENTION

1H-Imidazo[4,5-c]quinolines as kinase inhibitors are described in WO 2003/097641, WO 2005/054237 and WO 2005/054238.

The aim of the present invention is to indicate new compounds which can be used for the prevention and/or treatment of diseases characterised by excessive or abnormal cell proliferation. The compounds according to the invention are characterised by a powerful inhibitory effect on PDK 1 and a high efficacy against tumour cells, e.g. prostate carcinoma cells, which is mediated through inhibiting PDK 1. As well as the inhibitory effect and cell potency the compounds have good solubility and good selectivity with regard to other signal and cell cycle kinases.

The importance of the PI3K-PDK1-AKT pathway with its frequent aberrations (PTEN loss, PI3K mutation) in the major tumor indications is described in numerous scientific publications (e.g. Samuels et al. 2004; Science; 304: 554; Samuels and Velculescu 2004; Cell Cycle 3; 17-19; Samuels et al. 2005; Cancer Cell; 7: 561-573).

PDK1 alterations (mutations, CN gains) are rarely found isolated from other pathway alterations so that the importance of this target thrives from the fact that it acts as a central signaling node in a frequently altered pathway.

Active PI3K phosphorylates second messengers like Phosphatidylinositol(4,5)-bisphosphate (PtdIns(4,5)P2) to PtdIns(3,4,5)P3, or PtdIns(4)P to PtdIns(3,4,)P2. Such PI3K products recruit AKT and PDK1 kinases via their PH-domains (which bind the PI3 kinase products) to the plasma membrane and allow PDK1 to phosphorylate Thr308 of AKT and thereby activate the enzyme. A second step important for additional AKT activation and/or AKT-substrate selection is mediated by the mTOR/rictor/SIN1 complex which phosphorylates the hydrophobic motif of AKT at Ser473. Activated AKT regulates several other proteins, which are involved in cell proliferation, growth and survival.

Besides AKT, PDK1 has other substrates located in the cytoplasm, e.g. p70S6K, p90RSK, PKCs and SGK, which are also implicated in regulating cell proliferation and cell survival. The activation of these kinases is not dependent on phosphatidylinositols in vitro and functions properly in cells where the PDK1-PH-domain had been destroyed by knock-in mutation (McManus et al. 2004, EMBO J. 23, 2071-2082). For a review on PDK1 mouse mutants also see Bayascas 2008; Cell Cycle 7; 2978-2982).

In conclusion, PDK1 substrates (AKT, p90RSK) act at the crossroad of two important cancer signaling pathways.

A potent and selective inhibitor of the PDK1 kinase is predicted to inhibit tumor growth, delay relapse, or even induce objective tumor responses (i.e. complete or partial tumor shrinkage) in cancer patients.

DETAILED DESCRIPTION OF THE INVENTION

It has been found that, surprisingly, compounds of general formula (1) wherein the groups $R^1$ to $R^7$, $Q^a$, $Q^b$, L, m and n are defined as stated hereinafter act as inhibitors of specific signal enzymes which are involved in controlling the proliferation of cells. Thus, the compounds according to the invention may be used for example for the treatment of diseases which are connected with the activity of these signal enzymes and are characterised by excessive or abnormal cell proliferation.

The present invention therefore relates to compounds of general formula (1)

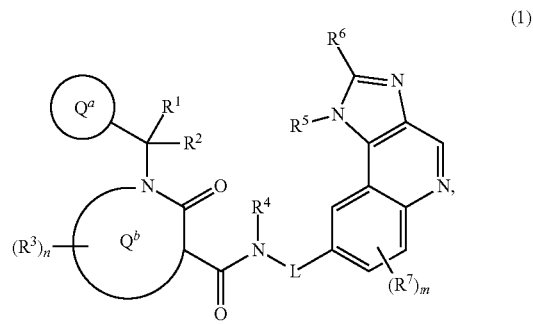

wherein (A0)

$Q^a$ is a ring system optionally substituted by one or more, identical or different $R^a$ and/or $R^b$, selected from among $C_{3-10}$cycloalkyl, $C_{6-10}$aryl, 5-12 membered heteroaryl and 3-14 membered heterocyclyl;

(B0)

$R^1$ and $R^2$ are selected independently from among hydrogen, halogen, $C_{1-4}$alkyl, $C_{2-4}$alkenyl, $C_{2-4}$alkynyl, $C_{1-4}$haloalkyl, —$NH_2$, —CN, —NH$C_{1-4}$alkyl, —N($C_{1-4}$alkyl)$_2$, —OH, —O$C_{1-4}$alkyl, HO—$C_{1-4}$alkylene-, $C_{1-4}$alkyl-O—$C_{1-4}$alkylene-, $H_2$N—$C_{1-4}$alkylene-, —O—$C_{1-4}$haloalkyl, ($C_{1-4}$alkyl)NH—$C_{1-4}$alkylene- and ($C_{1-4}$alkyl)$_2$N—$C_{1-4}$alkylene-, wherein the alkyl, alkenyl, alkynyl and alkylene mentioned in the above groups may optionally be substituted by one or more identical or different halogen atoms;

(C0)
the ring system $Q^b$ is selected from among

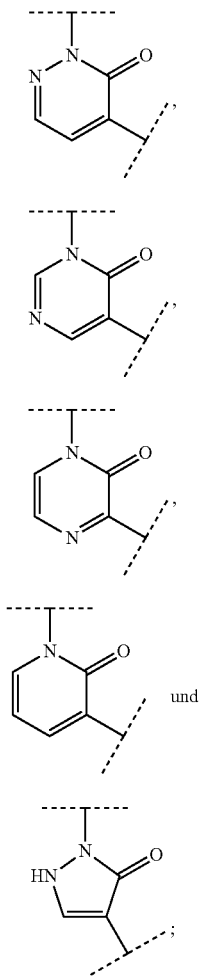

each $R^3$ is independently selected from among halogen, $C_{1-4}$alkyl, $C_{2-4}$alkenyl, $C_{2-4}$alkynyl, $C_{1-4}$haloalkyl, —NH$_2$, —CN, —NHC$_{1-4}$alkyl, —N(C$_{1-4}$alkyl)$_2$, —OH, —O—C$_{1-4}$alkyl, HO—C$_{1-4}$alkylene-, HO—C$_{2-4}$alkylene-O—, C$_{1-4}$alkyl-O—C$_{1-4}$alkylene-, —O—C$_{1-4}$haloalkyl-O—C$_{1-4}$alkylene-, H$_2$N—C$_{1-4}$alkylene-, C$_{1-4}$alkyl-O—C$_{2-4}$alkylene-O—, (C$_{1-4}$alkyl)NH—C$_{1-4}$alkylene-, (C$_{1-4}$alkyl)$_2$N—C$_{1-4}$alkylene-, —OC$_{1-4}$haloalkyl, H$_2$N—C$_{2-4}$alkylene-O—, —NH(C$_{2-4}$alkylene-NH$_2$), —NH[C$_{2-4}$alkylene-NH(C$_{1-4}$alkyl)], —NH[C$_{2-4}$alkylene-N(C$_{1-4}$alkyl)$_2$], (C$_{1-4}$alkyl)$_2$N—C$_{2-4}$alkylene-O—, (C$_{1-4}$haloalkyl)$_2$N—C$_{2-4}$alkylene-O—, (C$_{1-4}$haloalkyl)NH—C$_{2-4}$alkylene-O— and (C$_{1-4}$alkyl)NH—C$_{2-4}$alkylene-O—;

n denotes the number 0, 1, 2 or 3 if $Q^b$ corresponds to the ring system $Q^b$-4;

each n independently denotes the number 0, 1 or 2 if $Q^b$ corresponds to one of the ring systems $Q^b$-1, $Q^b$-2, $Q^b$-3 or $Q^b$-5;

wherein a group $R^3$ in the ring systems $Q^b$-1 to $Q^b$-5 replaces a hydrogen in each case;

(D0)
$R^4$ denotes hydrogen or $C_{1-4}$alkyl;

(E0)
L denotes the group

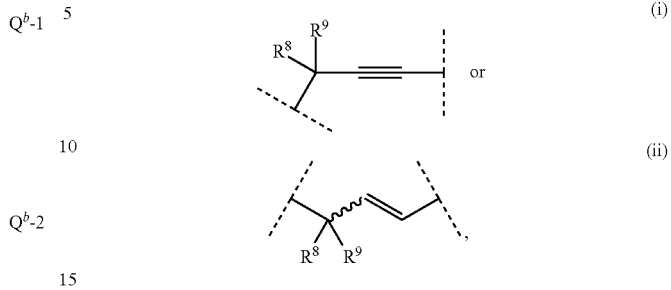

wherein
the group —CR$^8$R$^9$— binds to the group —NR$^4$—, in case (ii) both a cis and a trans configuration may be present with respect to the double bond and
$R^8$ and $R^9$ are independently selected from among hydrogen, halogen, $C_{1-4}$alkyl and $C_{1-4}$haloalkyl;

(F0)
$R^5$ is selected from among $R^a$ and $R^b$;

(G0)
$R^6$ is selected from among $R^a$ and $R^b$;

(H0)
each $R^7$ is independently selected from among $R^a$ and $R^b$;
m denotes the number 0, 1 or 2;

each $R^a$ independently denotes hydrogen or a group optionally substituted by one or more, identical or different $R^b$ and/or $R^c$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^b$ is independently selected from among —OR$^c$, —NR$^c$R$^c$, halogen, —CN, —NO$_2$, —C(O)R$^c$, —C(O)OR$^c$, —C(O)NR$^c$R$^c$, —S(O)$_2$R$^c$, —S(O)$_2$NR$^c$R$^c$, —NHC(O)R$^c$ and —N(C$_{1-4}$alkyl)C(O)R$^c$ as well as the bivalent substituent =O, wherein the latter may only be a substituent in non-aromatic ring systems;

each $R^c$ independently denotes hydrogen or a group optionally substituted by one or more, identical or different $R^d$ and/or $R^e$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^d$ is independently selected from among —OR$^e$, —NR$^e$R$^e$, halogen, —CN, —NO$_2$, —C(O)R$^e$, —C(O)OR$^e$, —C(O)NR$^e$R$^e$, —S(O)$_2$R$^e$, —S(O)$_2$NR$^e$R$^e$, —NHC(O)R$^e$ and —N(C$_{1-4}$alkyl)C(O)R$^e$, as well as the bivalent substituent =O, wherein the latter may only be a substituent in non-aromatic ring systems;

each $R^e$ independently denotes hydrogen or a group optionally substituted by one or more, identical or different $R^f$ and/or $R^g$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^f$ is independently selected from among —OR$^g$, —NR$^g$R$^g$, halogen, —CN, —NO$_2$, —C(O)R$^g$, —C(O)OR$^g$, —C(O)NR$^g$R$^g$, —S(O)$_2$R$^g$, —S(O)$_2$NR$^g$R$^g$, —NHC(O)R$^g$ and —N(C$_{1-4}$alkyl)C(O)R$^g$, as well as the bivalent substituent =O, wherein the latter may only be a substituent in non-aromatic ring systems and each $R^g$ is independently selected from among hydrogen, $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

wherein the compounds (1) may optionally also be present in the form of their tautomers, racemates, enantiomers, diastereomers or mixtures thereof or as the respective salts of all the above-mentioned forms.

In one aspect (A1) the invention relates to compounds (1), wherein
$Q^a$ is a ring system optionally substituted by one or more, identical or different $R^a$ and/or $R^b$, selected from among $C_{5-6}$cycloalkyl, phenyl, 5-6 membered heteroaryl and 5-7 membered heterocyclyl, and
$R^a$ and $R^b$ are as hereinbefore defined.

In another aspect (A2) the invention relates to compounds (1), wherein
$Q^a$ is a ring system optionally substituted by one or more, identical or different $R^a$ and/or $R^b$, selected from among phenyl and 5-6 membered heteroaryl, and
$R^a$ and $R^b$ are as hereinbefore defined.

In other aspects (A3)(A4) the invention relates to compounds with structural aspect (A1) and (A2), wherein the ring system $Q^a$ optionally carries one or more identical or different substituents, selected from among halogen and $C_{1-4}$alkyl.

In another aspect (A5) the invention relates to compounds (1), wherein
$Q^a$ is selected from among phenyl, 3-fluorophenyl, 4-fluorophenyl, 3,4,5-trifluorophenyl, 3,5-difluorophenyl and 3,4-difluorophenyl.

In another aspect (A6) the invention relates to compounds (1), wherein
$Q^a$ denotes 3,4-difluorophenyl.

In another aspect (B1) the invention relates to compounds (1), wherein
$R^1$ and $R^2$ are selected independently of one another from among hydrogen, $C_{1-4}$alkyl, $C_{2-4}$alkynyl, —CN, $H_2N$—$C_{1-4}$alkylene-, $H_2N$—$C_{1-4}$alkylene-, $(C_{1-4}$alkyl)NH—$C_{1-4}$alkylene-, $(C_{1-4}$halolkyl)NH—$C_{1-4}$alkylene-, $(C_{1-4}$alkyl)$_2$N—$C_{1-4}$alkylene- and $(C_{1-4}$haloalkyl)$_2$N—$C_{1-4}$alkylene-.

In another aspect (B2) the invention relates to compounds (1), wherein
$R^1$ and $R^2$ are selected independently of one another from among hydrogen, $C_{1-4}$alkyl, $H_2N$—$C_{1-4}$alkylene- and HO—$C_{1-4}$alkylene-.

In another aspect (B3) the invention relates to compounds (1), wherein
$R^1$ and $R^2$ are selected independently of one another from among hydrogen, methyl, aminomethyl and hydroxymethyl.

In other aspects (B4)(B5)(B6) the invention relates to compounds with the structural aspect (B1), (B2) and (B3), wherein
$R^1$ denotes hydrogen.

In another aspect (C1) the invention relates to compounds (1), wherein
the ring system $Q^b$ is selected from among

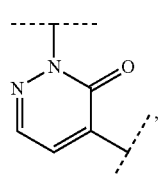

Q$^b$-1

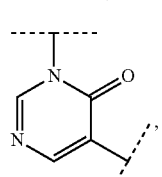

Q$^b$-2

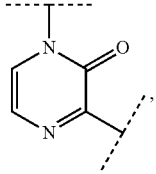

Q$^b$-3

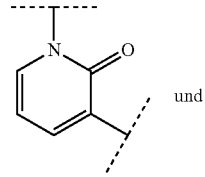

Q$^b$-4 und

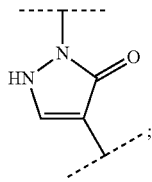

Q$^b$-5

;

each $R^3$ is independently selected from among halogen, $C_{1-4}$alkyl, —O$C_{1-4}$alkyl, HO—$C_{1-4}$alkylene-, $C_{1-4}$alkyl-O—$C_{1-4}$alkylene-, —NH($C_{2-4}$alkylene-NH$_2$), —NH[$C_{2-4}$alkylene-NH($C_{1-4}$alkyl)] and —NH[$C_{2-4}$alkylene-N($C_{1-4}$alkyl)$_2$];

n denotes the number 0, 1, 2 or 3 if $Q^b$ corresponds to the ring system $Q^b$-4 and each n independently denotes the number 0, 1 or 2 if $Q^b$ corresponds to one of the ring systems $Q^b$-1, $Q^b$-2, $Q^b$-3 or $Q^b$-5, wherein a group $R^3$ in the ring systems $Q^b$-1 to $Q^b$-5 replaces a hydrogen in each case.

In another aspect (C2) the invention relates to compounds (1), wherein
the ring system $Q^b$ is selected from among

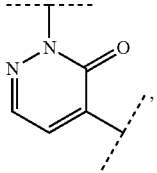

Q$^b$-1

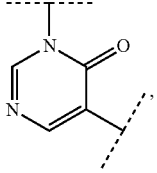

Q$^b$-2

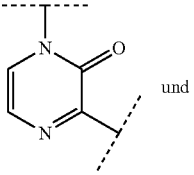

Q$^b$-3 und

-continued

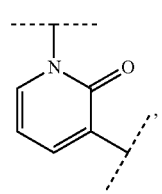
Q$^{b}$-4 and
n has the value 0.

In another aspect (C3) the invention relates to compounds (1), wherein
the ring system Q$^b$ is selected from among

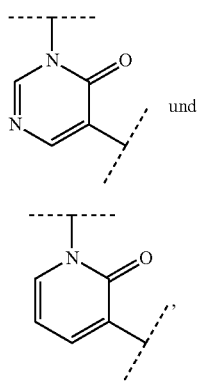

and
n has the value 0.

In another aspect (C4) the invention relates to compounds (1), wherein
the ring system Q$^b$ together with the n substituents R$^3$ is selected from among

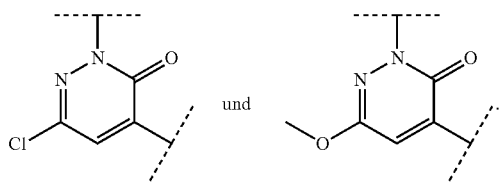

In another aspect (D1) the invention relates to compounds (1), wherein
R$^4$ denotes hydrogen or methyl.

In another aspect (D2) the invention relates to compounds (1), wherein
R$^4$ denotes hydrogen.

In another aspect (E1) the invention relates to compounds (1), wherein
L denotes the group

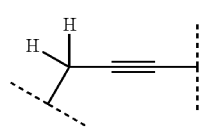

and
the group —CH$_2$— binds to the group —NR$^4$—.

In another aspect (F1) the invention relates to compounds (1), wherein
R$^5$ is selected from among R$^{a1}$ and R$^{b1}$;
R$^{a1}$ denotes hydrogen or a group optionally substituted by one or more, identical or different R$^{b1}$ and/or R$^{c1}$, selected from among C$_{1-6}$alkyl, C$_{2-6}$alkenyl, C$_{2-6}$alkynyl, C$_{3-10}$cycloalkyl, C$_{6-10}$aryl, 5-12 membered heteroaryl and 3-14 membered heterocyclyl;
each R$^{b1}$ is independently selected from among —OR$^{c1}$, —NR$^{c1}$R$^{c1}$, halogen, —CN, —NO$_2$, —C(O)R$^{c1}$, —C(O)OR$^{c1}$, —C(O)NR$^{c1}$R$^{c1}$—S(O)$_2$R$^{c1}$, —S(O)$_2$NR$^{c1}$R$^{c1}$—NHC(O)R$^{c1}$ and —N(C$_{1-4}$alkyl)C(O)R$^{c1}$ as well as the bivalent substituent =O, wherein the latter may only be a substituent in non-aromatic ring systems;
each R$^{c1}$ independently denotes hydrogen or a group optionally substituted by one or more, identical or different R$^{d1}$ and/or R$^{e1}$, selected from among C$_{1-6}$alkyl, C$_{2-6}$alkenyl, C$_{2-6}$alkynyl, C$_{3-10}$cycloalkyl, C$_{6-10}$aryl, 5-12 membered heteroaryl and 3-14 membered heterocyclyl;
each R$^{d1}$ is independently selected from among —OR$^{e1}$, —NR$^{e1}$R$^{e1}$, halogen, —CN, —NO$_2$, —C(O)R$^{e1}$, —C(O)OR$^{e1}$, —C(O)NR$^{e1}$R$^{e1}$, —S(O)$_2$R$^{e1}$, —S(O)$_2$NR$^{e1}$R$^{e1}$, —NHC(O)R$^{e1}$ and —N(C$_{1-4}$alkyl)C(O)R$^{e1}$, as well as the bivalent substituent =O, wherein the latter may only be a substituent in non-aromatic ring systems;
each R$^{e1}$ independently denotes hydrogen or a group optionally substituted by one or more, identical or different R$^{f1}$ and/or R$^{g1}$, selected from among C$_{1-6}$alkyl, C$_{2-6}$alkenyl, C$_{2-6}$alkynyl, C$_{3-10}$cycloalkyl, C$_{6-10}$aryl, 5-12 membered heteroaryl and 3-14 membered heterocyclyl;
each R$^{f1}$ is independently selected from among —OR$^{g1}$, —NR$^{g1}$R$^{g1}$, halogen, —CN, —NO$_2$, —C(O)R$^{g1}$, —C(O)OR$^{g1}$, —C(O)NR$^{g1}$R$^{g1}$, —S(O)$_2$R$^{g1}$, —S(O)$_2$NR$^{g1}$R$^{g1}$, —NHC(O)R$^{g1}$ and —N(C$_{1-4}$alkyl)C(O)R$^{g1}$, as well as the bivalent substituent =O, wherein the latter may only be a substituent in non-aromatic ring systems and
each R$^{g1}$ is independently selected from among hydrogen, C$_{1-6}$alkyl, C$_{2-6}$alkenyl, C$_{2-6}$alkynyl, C$_{3-10}$cycloalkyl, C$_{6-10}$aryl, 5-12 membered heteroaryl and 3-14 membered heterocyclyl.

In another aspect (F2) the invention relates to compounds (1), wherein
R$^5$ is selected from among R$^{a1}$ and R$^{b1}$;
R$^{a1}$ denotes hydrogen or a group optionally substituted by one or more, identical or different R$^{b1}$ and/or R$^{c1}$, selected from among C$_{1-6}$alkyl, C$_{2-6}$alkenyl, C$_{2-6}$alkynyl, C$_{3-10}$cycloalkyl, C$_{6-10}$aryl, 5-12 membered heteroaryl and 3-14 membered heterocyclyl;
each R$^{b1}$ is independently selected from among —OR$^{c1}$, —NR$^{c1}$R$^{c1}$ halogen, —CN, —NO$_2$, —C(O)R$^{c1}$, —C(O)OR$^{c1}$, —C(O)NR$^{c1}$R$^{c1}$, —S(O)$_2$R$^{c1}$, —S(O)$_2$NR$^{c1}$R$^{c1}$, —NHC(O)R$^{c1}$ and —N(C$_{1-4}$alkyl)C(O)R$^{c1}$ as well as the bivalent substituent =O, wherein the latter may only be a substituent in non-aromatic ring systems and
each R$^{c1}$ is independently selected from among hydrogen, C$_{1-6}$alkyl, C$_{2-6}$alkenyl, C$_{2-6}$alkynyl, C$_{3-10}$cycloalkyl, C$_{6-10}$aryl, 5-12 membered heteroaryl and 3-14 membered heterocyclyl.

In another aspect (F3) the invention relates to compounds (1), wherein
R$^5$ is selected from among R$^{a1}$ and R$^{b1}$;
R$^{a1}$ denotes hydrogen or a group optionally substituted by one or more, identical or different R$^{b1}$ and/or R$^{c1}$, selected from among C$_{1-6}$alkyl, C$_{3-10}$cycloalkyl and 3-14 membered heterocyclyl;

each $R^{b1}$ is independently selected from among —$OR^{c1}$ and —$NR^{c1}R^{c1}$ and each $R^{c1}$ is independently selected from among hydrogen, $C_{1-6}$alkyl and $C_{6-10}$aryl.

In another aspect (F4) the invention relates to compounds (1), wherein
$R^5$ is selected from among hydrogen, $C_{1-6}$alkyl, HO—$C_{1-4}$alkylene-, $C_{4-6}$cycloalkyl, $H_2N$—$C_{1-4}$alkylene-, $(C_{1-4}$alkyl$)NH$—$C_{1-4}$alkylene-, $(C_{1-4}$alkyl$)_2N$—$C_{1-4}$alkylene-, piperidinyl, N—$(C_{1-4}$alkyl$)$-piperidinyl, pyrrolidinyl, N—$(C_{1-4}$alkyl$)$-pyrrolidinyl, phenyl-$C_{1-4}$alkylene-, tetrahydropyranyl and tetrahydrofuryl, wherein the above-mentioned $C_{4-6}$cycloalkyl may optionally be substituted by a substituent selected from among —$NH_2$, —$NH(C_{1-4}$alkyl$)$ or —$N(C_{1-4}$alkyl$)_2$.

In another aspect (F5) the invention relates to compounds (1), wherein
$R^5$ is selected from among hydrogen, methyl, ethyl, isopropyl, hydroxyethyl, hydroxypropyl, cyclobutyl, N,N-dimethylaminoethyl, N,N-dimethylaminopropyl, N-methylpiperidinyl, N-isopropylpiperidinyl, N-ethylpiperidinyl, N-methylpyrrolidinyl, piperidinyl, pyrrolidinyl, N,N-dimethylaminocyclohexyl, phenylethyl, tetrahydropyranyl and tetrahydrofuryl.

In another aspect (F6) the invention relates to compounds (1), wherein
$R^5$ is selected from among

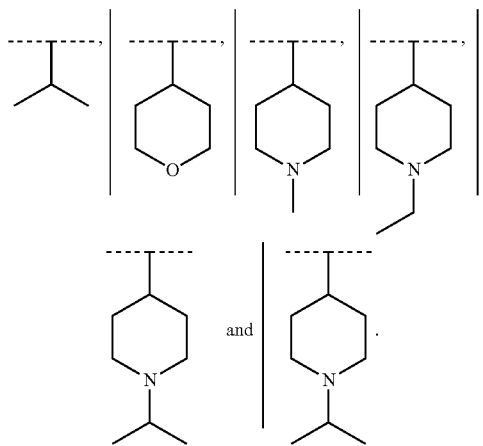

In another aspect (G1) the invention relates to compounds (1), wherein
$R^6$ is selected from among hydrogen, $C_{1-6}$alkyl, HO—$C_{1-4}$alkylene-, $C_{1-4}$alkyl-O—$C_{1-4}$alkylene-, $C_{1-6}$alkyl-O, phenyl, $C_{1-6}$haloalkyl, $H_2N$—$C_{1-4}$alkylene-, $(C_{1-4}$alkyl$)NH$—$C_{1-4}$alkylene- and $(C_{1-4}$alkyl$)_2N$—$C_{1-4}$alkylene-.

In another aspect (G2) the invention relates to compounds (1), wherein
$R^6$ is selected from among hydrogen and $C_{1-6}$alkyl.

In another aspect (G3) the invention relates to compounds (1), wherein
$R^6$ is selected from among hydrogen and methyl.

In another aspect (H1) the invention relates to compounds (1), wherein
m has the value 0.

All the above-mentioned structural aspects A1 to A6, B1 to B6, C1 to C4, D1 and D2, E1, F1 to F6, G1 to G3 and H1 are preferred embodiments of the aspects A0, B0, C0, D0, E0, F0, G0 and H0, respectively. The structural aspects A0 to A6, B0 to B6, C0 to C4, D0 to D2, E0 and E1, F0 to F6, G0 to G3 and H0 and H1 relating to different molecular parts of the compounds (1) according to the invention may be permutated with one another as desired in combinations ABCDEFGH so as to obtain preferred compounds (1). Each combination ABCDEFGH represents and defines individual embodiments or generic amounts of compounds A0B0C0D0E0F0G0H0 according to the invention. Each individual embodiment or partial quantity defined by this combination is expressly also included and is a subject of the invention.

In a preferred embodiment of the present invention the compounds (1) are selected from 1-[(3,4-difluorophenyl)methyl]-N-[3-(2-methyl-1-propan-2-ylimidazo[4,5-c]quinolin-8-yl)prop-2-ynyl]-6-oxopyrimidine-5-carboxamide;

1-[(1R)-1-(3,4-difluorophenyl)ethyl]-N-[3-[2-methyl-1-(1-methylpiperidin-4-yl)imidazo[4,5-c]quinolin-8-yl]prop-2-ynyl]-2-oxopyridine-3-carboxamide;

1-[(1S)-1-(3,4-difluorophenyl)ethyl]-N-[3-(2-methyl-1-propan-2-ylimidazo[4,5-c]quinolin-8-yl)prop-2-ynyl]-2-oxopyridine-3-carboxamide;

1-[(3,4-difluorophenyl)methyl]-2,3-dimethyl-N-[3-(2-methyl-1-propan-2-ylimidazo[4,5-c]quinolin-8-yl)prop-2-ynyl]-5-oxopyrazole-4-carboxamide;

1-[(3,4-difluorophenyl)methyl]-N-[3-[2-methyl-1-(1-methylpiperidin-4-yl)imidazo[4,5-c]quinolin-8-yl]prop-2-ynyl]-2-oxopyridine-3-carboxamide;

1-[(1R)-1-(3,4-difluorophenyl)ethyl]-N-[3-[1-[4-(dimethylamino)cyclohexyl]-2-methylimidazo[4,5-c]quinolin-8-yl]prop-2-ynyl]-2-oxopyridine-3-carboxamide;

1-[(1R)-2-amino-1-(3,4-difluorophenyl)ethyl]-N-[3-(2-methyl-1-propan-2-ylimidazo[4,5-c]quinolin-8-yl)prop-2-ynyl]-2-oxopyridine-3-carboxamide;

1-[(1R)-1-(3,4-difluorophenyl)ethyl]-N-[3-[1-[4-(dimethylamino)cyclohexyl]-2-methylimidazo[4,5-c]quinolin-8-yl]prop-2-ynyl]-2-oxopyridine-3-carboxamide;

2-[(3,4-difluorophenyl)methyl]-6-methoxy-N-[3-(2-methyl-1-propan-2-ylimidazo[4,5-c]quinolin-8-yl)prop-2-ynyl]-3-oxopyridazine-4-carboxamide;

6-chloro-2-[(3,4-difluorophenyl)methyl]-N-[3-[1-(1-methylpiperidin-4-yl)imidazo[4,5-c]quinolin-8-yl]prop-2-ynyl]-3-oxopyridazine-4-carboxamide;

1-[[(1S,4R)-3-bicyclo[2.2.1]heptanyl]methyl]-N-[3-(2-methyl-1-propan-2-ylimidazo[4,5-c]quinolin-8-yl)prop-2-ynyl]-2-oxopyridine-3-carboxamide;

1-[(1R)-1-(3-fluorophenyl)-2-hydroxyethyl]-N-[3-(2-methyl-1-propan-2-ylimidazo[4,5-c]quinolin-8-yl)prop-2-ynyl]-2-oxopyridine-3-carboxamide;

2-[(3,4-difluorophenyl)methyl]-N-[3-[1-[4-(dimethylamino)cyclohexyl]imidazo[4,5-c]quinolin-8-yl]prop-2-ynyl]-6-methyl-3-oxopyridazine-4-carboxamide;

1-[(3,4-difluorophenyl)methyl]-N-[3-[1-(1-ethylpiperidin-4-yl)imidazo[4,5-c]quinolin-8-yl]prop-2-ynyl]-2,3-dimethyl-5-oxopyrazole-4-carboxamide;

1-[(3,4-difluorophenyl)methyl]-2-oxo-N-[3-[1-(1-propan-2-ylpiperidin-4-yl)imidazo[4,5-c]quinolin-8-yl]prop-2-ynyl]pyridine-3-carboxamide;

1-[(3,4-difluorophenyl)methyl]-N-[3-[1-[(3S)-1-methylpyrrolidin-3-yl]imidazo[4,5-c]quinolin-8-yl]prop-2-ynyl]-2-oxopyridine-3-carboxamide;

1-[(3,4-difluorophenyl)methyl]-N-[3-[2-methyl-1-(1-propan-2-ylpiperidin-4-yl)imidazo[4,5-c]quinolin-8-yl]prop-2-ynyl]-2-oxopyridine-3-carboxamide;

N-[3-[1-[4-(dimethylamino)cyclohexyl]imidazo[4,5-c]quinolin-8-yl]prop-2-ynyl]-1-[(1R)-1-(3-fluorophenyl)-2-hydroxyethyl]-2-oxopyridine-3-carboxamide;

N-[3-[1-[4-(dimethylamino)cyclohexyl]-2-methylimidazo[4,5-c]quinolin-8-yl]prop-2-ynyl]-1-[(1R)-1-(3-fluorophenyl)-2-hydroxyethyl]-2-oxopyridine-3-carboxamide;

2-[(1S)-1-(3,4-difluorophenyl)ethyl]-6-methyl-N-[3-(2-methyl-1-propan-2-ylimidazo[4,5-c]quinolin-8-yl)prop-2-ynyl]-3-oxopyridazine-4-carboxamide;

2-[(1S)-1-(3,4-difluorophenyl)ethyl]-6-methyl-N-[3-(2-methyl-1-propan-2-ylimidazo[4,5-c]quinolin-8-yl)prop-2-ynyl]-3-oxopyridazine-4-carboxamide.

The present invention further relates to hydrates, solvates, polymorphs, metabolites, derivatives and prodrugs of compounds of general formula (1).

In another aspect the invention relates to compounds of general formula (1)—or the pharmaceutically acceptable salts thereof—as medicaments.

In another aspect the invention relates to compounds of general formula (1)—or the pharmaceutically acceptable salts thereof—for use in the treatment and/or prevention of cancer, infections, inflammations and autoimmune diseases.

In another aspect the invention relates to compounds of general formula (1)—or the pharmaceutically acceptable salts thereof—for use in the treatment and/or prevention of cancer.

In another aspect the invention relates to compounds of general formula (1)—or the pharmaceutically acceptable salts thereof—for use in the treatment and/or prevention of carcinomas of the breast, prostate or ovary, non-small-cell bronchial carcinomas (NSCLC), melanomas and chronic lymphatic leukaemias (CLL).

In another aspect the invention relates to a process for the treatment and/or prevention of cancer comprising administering a therapeutically effective amount of a compound of general formula (1)—or one of the pharmaceutically acceptable salts thereof—to a human being.

In another aspect the invention relates to a pharmaceutical preparation containing as active substance one or more compounds of general formula (1)—or the pharmaceutically acceptable salts thereof—optionally in combination with conventional excipients and/or carriers.

In another aspect the invention relates to a pharmaceutical preparation comprising a compound of general formula (1)—or one of the pharmaceutically acceptable salts thereof—and at least one other cytostatic or cytotoxic active substance, different from formula (1).

DEFINITIONS

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number (x<y), indicates that the chains or ring structure or combination of chains and ring structure as a whole, specified and mentioned in direct association, may consist of a maximum of y and a minimum of x carbon atoms.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$-alkyl" includes for example $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

Further examples of alkyl are methyl (Me; $-CH_3C$), ethyl (Et; $-CH_2CH_3$), 1-propyl (n-propyl; n-Pr; $-CH_2CH_2CH_3$), 2-propyl (i-Pr; iso-propyl; $-CH(CH_3)_2$), 1-butyl (n-butyl; n-Bu; $-CH_2CH_2CH_2CH_3$), 2-methyl-1-propyl (iso-butyl; i-Bu; $-CH_2CH(CH_3)_2$), 2-butyl (sec-butyl; sec-Bu; $-CH(CH_3)CH_2CH_3$), 2-methyl-2-propyl (tert-butyl; t-Bu; $-C(CH_3)_3$), 1-pentyl (n-pentyl; $-CH_2CH_2CH_2CH_2CH_3$), 2-pentyl ($-CH(CH_3)CH_2CH_2CH_3$), 3-pentyl ($-CH(CH_2CH_3)_2$), 3-methyl-1-butyl (iso-pentyl; $-CH_2CH_2CH(CH_3)_2$), 2-methyl-2-butyl ($-C(CH_3)_2CH_2CH_3$), 3-methyl-2-butyl ($-CH(CH_3)CH(CH_3)_2$), 2,2-dimethyl-1-propyl (neo-pentyl; $-CH_2C(CH_3)_3$), 2-methyl-1-butyl ($-CH_2CH(CH_3)CH_2CH_3$), 1-hexyl (n-hexyl; $-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 2,3-dimethyl-1-butyl($-CH_2CH(CH_3)CH(CH_3)CH_3$), 2,2-dimethyl-1-butyl ($-CH_2C(CH_3)_2CH_2CH_3$), 3,3-dimethyl-1-butyl ($-CH_2CH_2C(CH_3)_3$), 2-methyl-1-pentyl ($-CH_2CH(CH_3)CH_2CH_2CH_3$), 3-methyl-1-pentyl ($-CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example $-CH_3$ and $-CH_2-$, $-CH_2CH_3$ and $-CH_2CH_2-$ or >$CHCH_3$ etc.

The term "$C_{1-4}$-alkylene" includes for example $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_3))-$, $-(CHCH(CH_3)_2)-$ and $-C(CH_3)(CH_2CH_3)-$.

Other examples of alkylene are methylene, ethylene, propylene, 1-methylethylene, butylene, 1-methylpropylene, 1,1- dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or $H_2N$—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or $H_2N$—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —CF$_2$CH$_2$CH$_3$, —CF=CF$_2$, —CCl=CH$_2$, —CBr=CH$_2$, —Cl=CH$_2$, —C≡C—CF$_3$, —CHFCH$_2$CH$_3$, —CHFCH$_2$CF$_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —CH$_2$F and —CHF—, —CHFCH$_2$F and —CHFCHF— or >CFCH$_2$F etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms.

Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl(octahydroindenyl), bicyclo[4.4.0]decyl (decahydronaphthalene), bicyclo[2.2.1]heptyl(norbornyl), bicyclo[4.1.0]heptyl(norcaranyl), bicyclo-[3.1.1]heptyl(pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

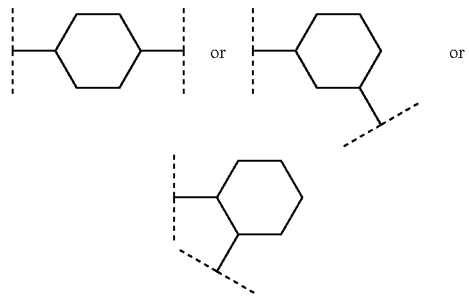

(cyclohexylene).

The above definition for cycloalkylene also applies if cycloalkylene is part of another group as in HO—$C_{x-y}$-cycloalkyleneamino or H$_2$N—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl(norborna-2,5-dienyl), bicyclo[2.2.1]hept-2-enyl(norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

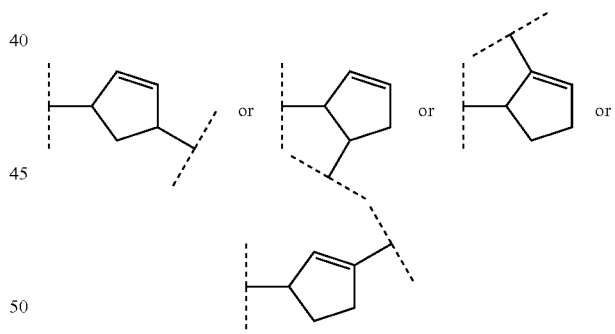

(cyclopentenylene) etc.

The above definition for cycloalkenylene also applies when cycloalkenylene is part of another group as in HO—$C_{x-y}$-cycloalkenyleneamino or H$_2$N—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g.
phenyl and

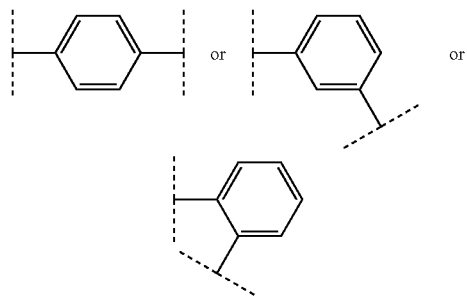

(o, m, p-phenylene), naphthyl and

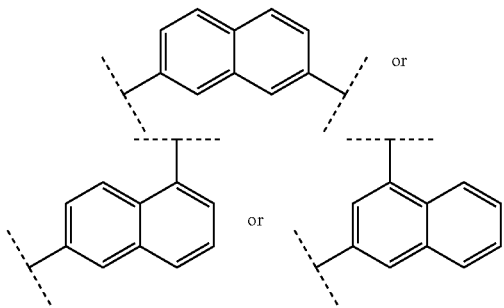

etc.

The above definition for arylene also applies when arylene is part of another group as in HO-aryleneamino or H$_2$N-aryleneoxy for example.

Heterocyclyl denotes ring systems, which are derived from the previously defined cycloalkyl, cycloalkenyl and aryl by replacing one or more of the groups —CH$_2$-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-5-oxide, tetrahydrothienyl-S, S-dioxide, homothiomorpholinyl-5-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4.5]decyl etc.

Further examples are the structures illustrated below, which may be attached via each hydrogen-carrying atom (exchanged for hydrogen):

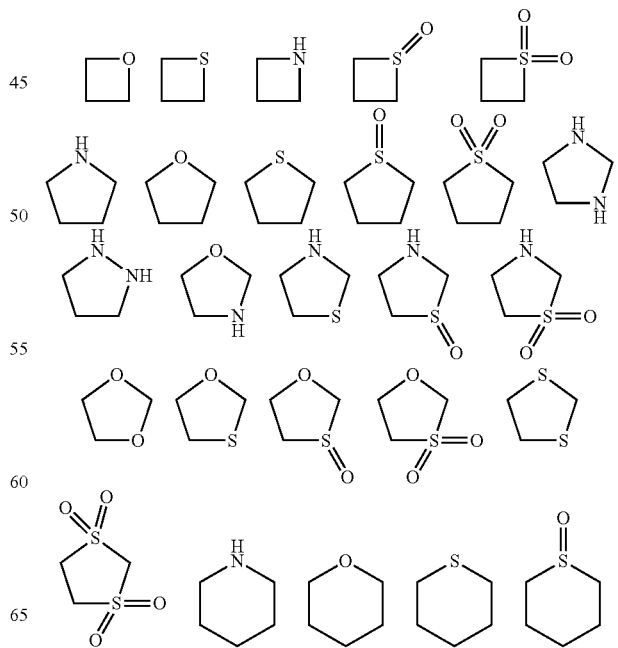

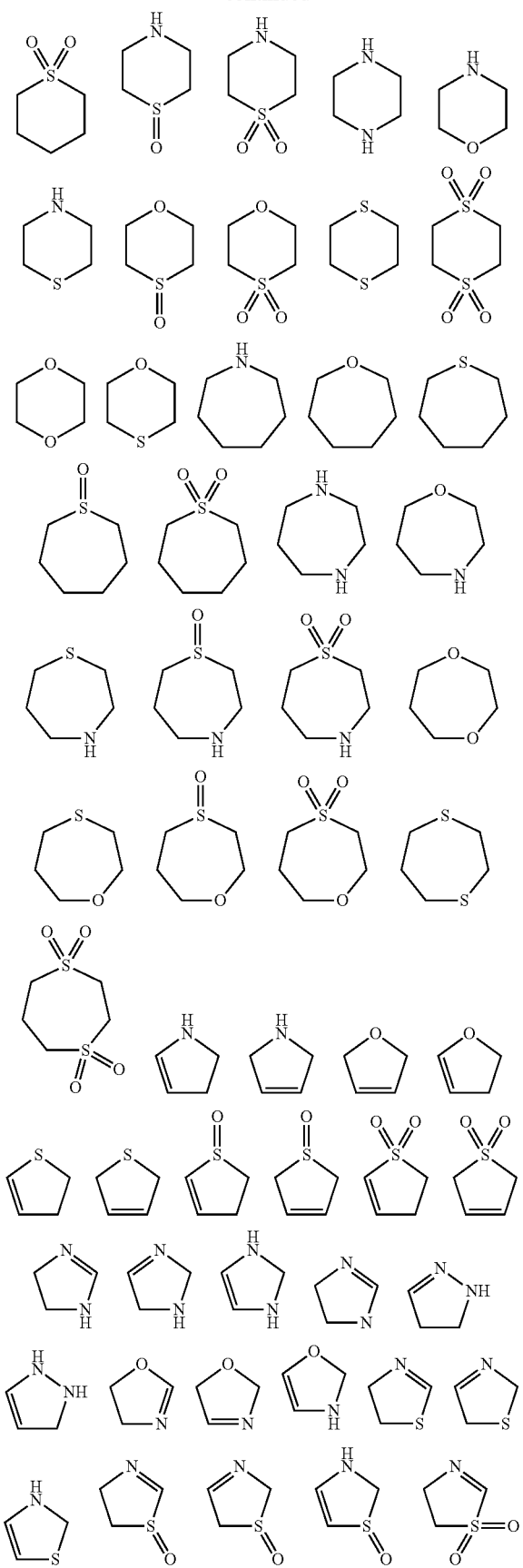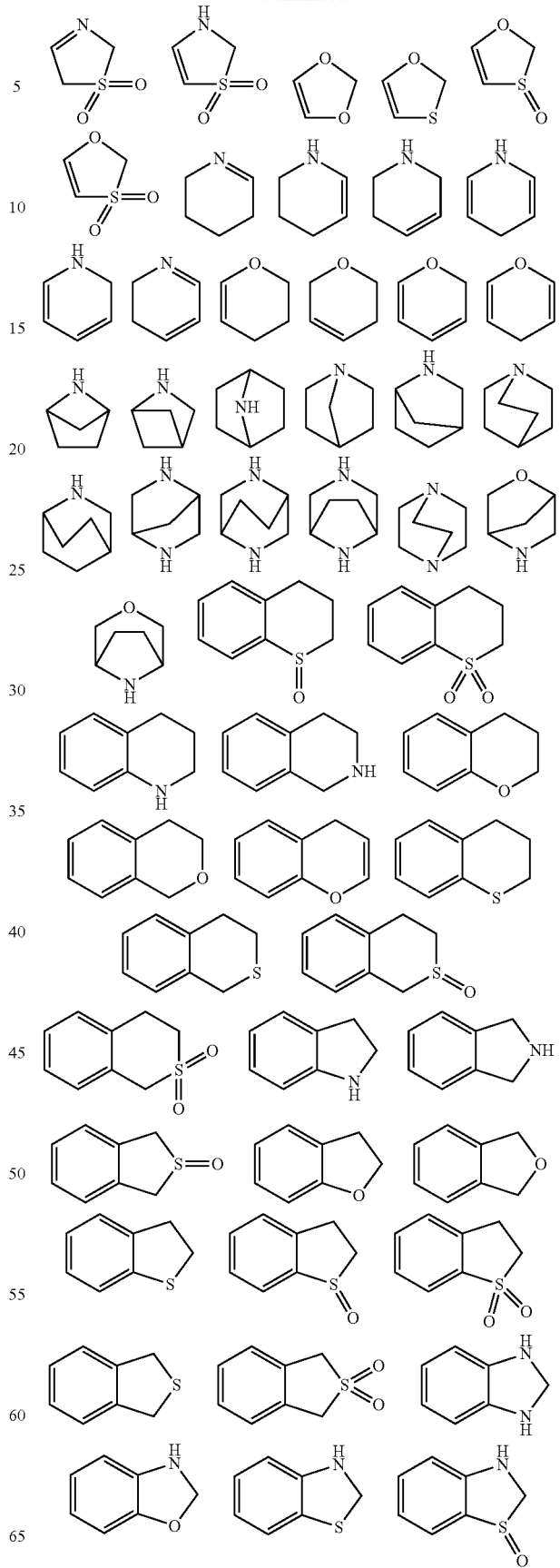

2,3-dihydro-1H-pyrrolyl and

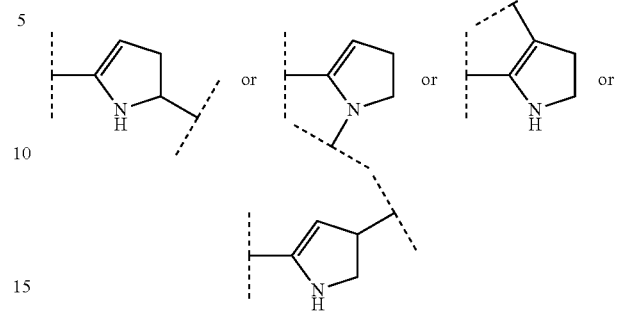

etc.

The above definition of heterocyclylene also applies if heterocyclylene is part of another group as in HO-heterocyclyleneamino or H$_2$N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

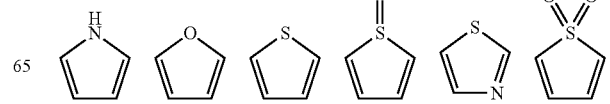

-continued

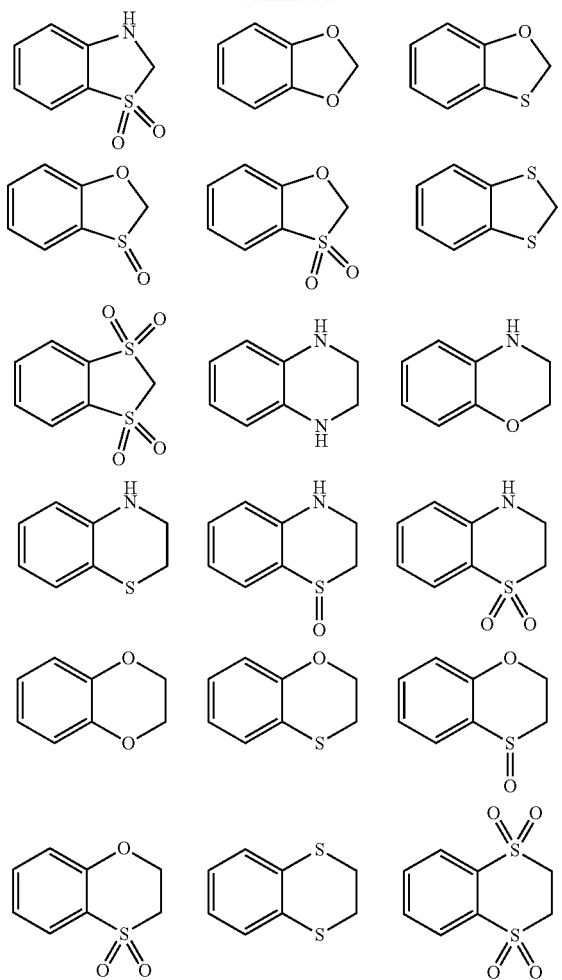

The above definition of heterocyclyl also applies if heterocyclyl is part of another group as in heterocyclylamino or heterocyclyloxy for example.

If the free valency of a heteroyclyl is saturated, then a heterocyclic group is obtained.

The term heterocyclylene is also derived from the previously defined heterocyclyl. Heterocyclylene, unlike heterocyclyl, is bivalent and requires two binding partners.

Formally, the second valency is obtained by removing a hydrogen atom from a heterocyclyl. Corresponding groups are for example piperidinyl and

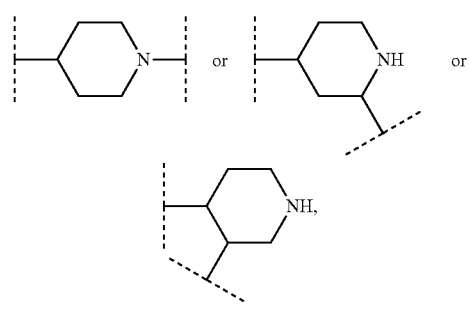

-continued

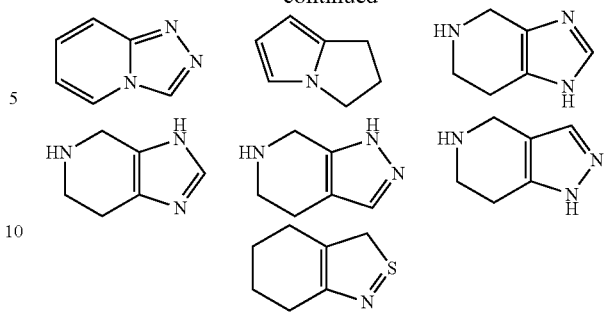

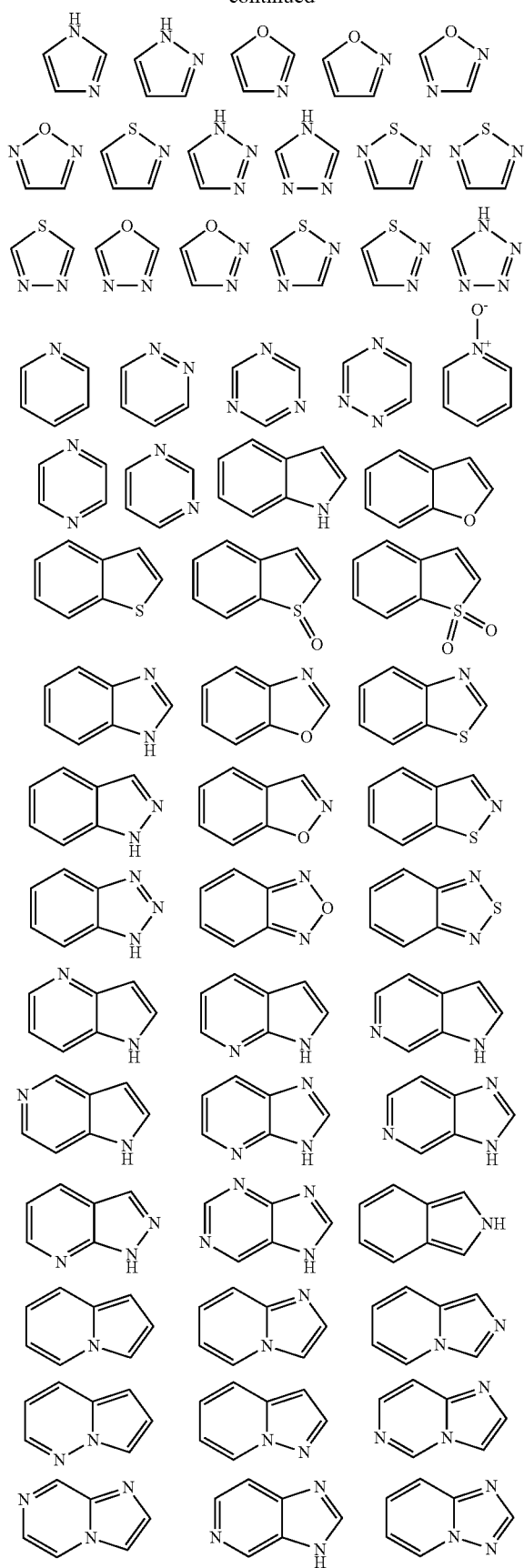

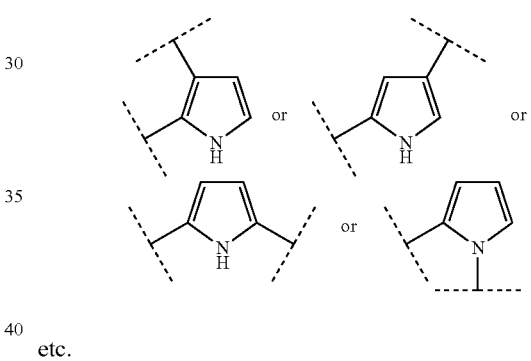

etc.

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N-C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituents at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH₂, or sulphur atoms of a ring system.

Stereochemistry/Solvates/Hydrates:

Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts:

The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof). Salts of acids other than those mentioned above, which are useful for example for purifying or isolating the compounds from the reaction mixtures (e.g. trifluoroacetates), are also to be regarded as part of the invention.

In a representation such as for example

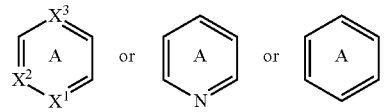

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

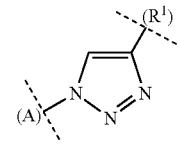

or (R²)—C(O)NH— or (R²)—NHC(O)—;

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| | |
|---|---|
| aa | amino acid |
| Ac | acetyl |
| ATP | adenosine triphosphate |
| Boc | tert.-butyloxycarbonyl |
| BSA | bovine serum albumin |
| Bu | butyl |
| d | day(s) |
| TLC | thin layer chromatography |
| DCC | dicyclohexylcarbodiimide |
| DCM | dichloromethane |
| DEA | diethylamine |
| DIC | diisopropylcarbodiimide |
| DIPEA | N-ethyl-N,N-diisopropylamine (HÜNIG base) |
| DMF | N,N-dimethylformamide |
| DMSO | dimethylsulphoxide |
| EDC | N-(3-dimethylaminopropyl)-N4-ethylcarbodiimide hydrochloride |
| ESI | electron spray ionization |
| Et | ethyl |
| EtOH | ethanol |
| h | hour |
| HATU | O-(7-azabenzotriazol-1-yl)-N,N,N',N'-tetramethyl-uronium hexafluorophosphate |

-continued

| | |
|---|---|
| HPLC | high performance liquid chromatography |
| Hünig base | N-ethyl-N,N-diisopropylamine |
| i | iso |
| cat. | catalyst, catalytic |
| conc. | concentrated |
| LC | liquid chromatography |
| sln. | solution |
| Me | methyl |
| MeOH | methanol |
| min | minutes |
| MPLC | medium pressure liquid chromatography |
| MS | mass spectrometry |
| MW | microwave |
| NMP | N-methylpyrrolidone |
| PBS | phosphate-buffered saline solution |
| Pd-DPPF | 1,1'-bis(diphenylphosphino)ferrocene-palladium(II)-dichloride dichloromethane |
| PDK1 | phosphoinositide-dependent kinase 1 |
| Ph | phenyl |
| PI3K | phosphatidylinositol-3-kinase |
| PKT | protein kinase B |
| Pr | propyl |
| $R_f$ (Rf) | retention factor |
| RP | reversed phase |
| RT | ambient temperature |
| s | second |
| TBTU | O-(benzotriazol-1-yl)-N,N,N',N'-tetramethyl-uronium tetrafluoroborate |
| TEA | triethylamine |
| tert. | tertiary |
| Tf | triflate |
| TFA | trifluoroacetic acid |
| THF | tetrahydrofuran |
| TMS | trimethylsilyl |
| Tos | tosyl |
| $t_{Ret.}$ | retention time (HPLC) |
| TRIS | tris(hydroxymethyl)-aminomethane |
| UV | ultraviolet |

Features and advantage of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Microwave reactions are carried out in an initiator/reactor made by Biotage or in an Explorer made by CEM in sealed containers (preferably 2, 5 or 20 mL), preferably with stirring.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18, 5 µm, 30×100 mm Part. No. 186002572; X-Bridge C18, 5 µm, 30×100 mm Part. No. 186002982).

The compounds are eluted using either different gradients of $H_2O$/acetonitrile or $H_2O$/MeOH, wherein 0.1% HCOOH is added to the water (acid conditions). For chromatography under basic conditions $H_2O$/acetonitrile gradients are also used, and the water is made basic according to the following recipe: 5 mL of an ammonium hydrogen carbonate solution (158 g to 1 L $H_2O$) and 2 mL ammonia (7M in MeOH) are made up to 1 L with $H_2O$.

The normal-phase preparative high pressure chromatography (HPLC) of the example compounds according to the invention is carried out with columns made by Macherey & Nagel (name: Nucleosil, 50-7, 40×250 mm) and VDSoptilab (name: Kromasil 100 $NH_2$, 10 µM, 50×250 mm). The compounds are eluted using different gradients of DCM/MeOH, with 0.1% $NH_3$ added to the MeOH.

The analytical HPLC (reaction monitoring) of intermediate compounds is carried out with columns made by Agilent, Waters and Phenomenex. The analytical equipment is also provided with a mass detector in each case.

HPLC Mass Spectroscopy/UV Spectrometry

The retention times/MS-ESI$^+$ for characterising the example compounds according to the invention are produced using an HPLC-MS apparatus (high performance liquid chromatography with mass detector) made by Agilent. Compounds that elute at the injection peak are given the retention time $t_{Ret.}$=0.00.

| HPLC-methods |
|---|
| Preparative |

| prep. HPLC1 | |
|---|---|
| HPLC: | 333 and 334 Pumps |
| Column: | Waters X-Bridge C18, 5 µm, 30 × 100 mm, Part. No. 186002982 |
| Eluant: | A: 10 mM $NH_4HCO_3$ in $H_2O$; B: acetonitrile (HPLC grade) |
| Detection: | UV/Vis-155 |
| Flow: | 50 mL/min |
| Gradient: | 0.00 min: 5% B |
| | 3.00-15.00 min: variable (see individual methods) |
| | 15.00-17.00 min: 100% B |
| prep. HPLC2 | |
| HPLC: | 333 and 334 Pumps |
| Column: | Waters Sunfire C18, 5 µm, 30 × 100 mm, Part. No. 186002572 |
| Eluant: | A: $H_2O$ + 0.2% HCOOH; B: acetonitrile (HPLC grade) + 0.2% HCOOH |
| Detection: | UV/Vis-155 |
| Flow: | 50 mL/min |
| Gradient: | 0.00 min: 5% B |
| | 3.00-15.00 min: variable (see individual methods) |
| | 15.00-17.00 min: 100% B |

-continued

| HPLC-methods |
|---|
| analytical |

LCMSBAS1

| | |
|---|---|
| HPLC: | Agilent 1100 Series |
| MS: | Agilent LC/MSD SL |
| Column: | Phenomenex Mercury Gemini C18, 3 µm, 2 × 20 mm, Part. No. 00M-4439-B0-CE |
| Eluant: | A: 5 mM $NH_4HCO_3$/20 mM $NH_3$ in $H_2O$; B: acetonitrile (HPLC grade) |
| Detection: | MS: Positive and negative mode |
| Mass range: | 120-900 m/z |
| Flow: | 1.00 mL/min |
| Column temp.: | 40° C. |
| Gradient: | 0.00 min: 5% B |
| | 0.00-2.50 min: 5% → 95% B |
| | 2.50-2.80 min: 95% B |
| | 2.81-3.10 min: 95% → 5% B |

FECB4/FECBM2

| | |
|---|---|
| HPLC: | Agilent 1100 Series |
| MS: | Agilent LC/MSD SL |
| Column: | Agilent Zorbax Extend C18, 3.5 µm, 2.1 × 50 mm, Part. No. 735700-902 |
| Eluant: | A: 5 mM $NH_4HCO_3$/20 mM $NH_3$ in $H_2O$; B: acetonitrile (HPLC grade) |
| Detection: | MS: Positive and negative mode |
| Mass range: | 105-1200 m/z |
| Flow: | 1.20 mL/min |
| Column temp.: | 35° C. |
| Gradient: | 0.01 min: 5% B |
| | 0.01-1.25 min: 5% → 95% B |
| | 1.25-2.00 min: 95% B |
| | 2.00-2.01 min: 95% → 5% B |

FECS

| | |
|---|---|
| HPLC: | Agilent 1100 Series |
| MS: | Agilent LC/MSD SL |
| Column: | Agilent Zorbax SB C8, 3.5 µm, 2.1 × 50 mm, Part. No. 871700-906 |
| Eluant: | A: $H_2O$ + 0.2% HCOOH; B: acetonitrile (HPLC grade) + 0.2 % HCOOH |
| Detection: | MS: Positive and negative mode |
| Mass range: | 105-1200 m/z |
| Flow: | 1.20 mL/min |
| Column temp.: | 35° C. |
| Gradient: | 0.01 min: 5% B |
| | 0.01-1.25 min: 5% → 95% B |
| | 1.25-2.00 min: 95% B |
| | 2.00-2.01 min: 95% → 5% B |

1_FEC

| | |
|---|---|
| HPLC: | Agilent 1100 Series |
| MS: | 1200 Series LC/MSD (API – ES + 3000 V, Quadrupol, G6140A) |
| Column: | Agilent Zorbax SB C8, 3.5 µm, 80 Å, 2.1 × 50 mm, Part. No.: 871700-906 |
| Eluant: | A: water + 0.1% HCOOH; B: acetonitrile (HPLC grade) + 0.1% HCOOH |
| Detection: | MS: Positive mode |
| Mass range: | 120-750 m/z |
| Flow: | 1.10 mL/min |
| Column temp.: | 45° C. |
| Gradient: | 0.0-1.75 min 15% → 95% B |
| | 1.75-1.9 min 95% B |
| | 1.9-1.92 min 95% → 15% B |
| | 1.92-2.1 min 15% B |

1_BAS_MeOH_POS

| | |
|---|---|
| HPLC: | Agilent 1100 Series |
| MS: | 1100 Series LC/MSD SL (MM – ES + APCI, + 3000 V, Quadrupol, G1956B) |
| Column: | Waters X-Bridge C18, 3.5 µm, 135 Å, 2.1 × 30 mm, Part. No.: 186003020 |
| Eluant: | A: 5 mM $NH_4HCO_3$/20 mM $NH_3$ (pH = 9.5); B: MeOH (HPLC grade) |
| Detection: | MS: Positive |
| Mass range: | 120-750 m/z |
| Flow: | 1.00 mL/min |
| Column temp.: | 40° C. |

| HPLC-methods | | |
|---|---|---|
| Gradient: | 0.0-1.0 min | 20% → 95% B |
| | 1.0-2.0 min | 95% B |
| | 2.0-2.1 min | 95% → 20% B |
| | 2.1-2.3 min | 20% B |

AFEC

| | |
|---|---|
| HPLC: | Agilent 1100/1200 Series |
| MS: | Agilent 1100 LC/MSD SL |
| Column: | Waters Sunfire C18, 5 µm, 2.1 × 50 mm |
| Eluant: | A: $H_2O$ + 0.1% HCOOH; B: acetonitrile |
| Detection: | MS: Positive and negative mode |
| Mass range: | 100-1200 m/z |
| Flow: | 1.00 mL/min |
| Column temp.: | 35° C. |
| Gradient: | 0.01 min: 5% B |
| | 0.01-1.50 min: 5% → 100% B |
| | 1.50-2.10 min: 100% B |
| | 2.10-2.20 min: 100% → 5% B |

FECS2

| | |
|---|---|
| HPLC: | Agilent 1100/1200 Series |
| MS: | Agilent 1100 LC/MSD SL |
| Column: | Sunfire C18, 5 µm, 2.1 × 50 mm |
| Eluant: | A: $H_2O$ + 0.2% HCOOH; B: MeOH |
| Detection: | ESI |
| Mass range: | 100-1200 m/z |
| Flow: | 1.20 mL/min |
| Column temp.: | 35° C. |
| Gradient: | 0.01 min: 5% B |
| | 0.01-1.50 min: 5% → 100% B |
| | 1.50-2.00 min: 100% B |

FECB6

| | |
|---|---|
| HPLC: | Agilent 1100/1200 Series |
| MS: | Agilent 1100 LC/MSD SL |
| Column: | Waters X-Bridge C18, 5 µm, 2.1 × 50 mm |
| Eluant: | A: $H_2O$ + 5 mM $NH_4HCO_3$, 19 mM $NH_3$; B: MeOH |
| Detection: | ESI |
| Mass range: | 100-1200 m/z |
| Flow: | 1.20 mL/min |
| Column temp.: | 35° C. |
| Gradient: | 0.01 min: 5% B |
| | 0.01-1.24 min: 5% → 100% B |
| | 1.24-2.10 min: 100% B |

FSUN

| | |
|---|---|
| HPLC: | Agilent 1100/1200 Series |
| MS: | Agilent 1100 LC/MSD SL |
| Column: | Waters Sunfire, 3.5 µm, 2.1 × 50 mm |
| Eluant: | A: $H_2O$ + 0.2% HCOOH; B: $CH_3CN$ |
| Detection: | ESI |
| Mass range: | 100-1200 m/z |
| Flow: | 1.20 mL/min |
| Column temp.: | 35° C. |
| Gradient: | 0.01 min: 5% B |
| | 0.01-1.50 min: 5% → 95% B |
| | 1.50-2.00 min: 100% B |

FSUN2

| | |
|---|---|
| HPLC: | Agilent 1100/1200 Series |
| MS: | Agilent 1100 LC/MSD SL |
| Column: | Waters Sunfire, 5.0 µm, 2.1 × 50 mm |
| Eluant: | A: $H_2O$ + 0.2% HCOOH; B: $CH_3CN$ |
| Detection: | ESI |
| Mass range: | 100-1200 m/z |
| Flow: | 1.20 mL/min |
| Column temp.: | 35° C. |
| Gradient: | 0.01 min: 5% B |
| | 0.01-1.50 min: 5% → 95% B |
| | 1.50-2.00 min: 100% B |

The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

a) Synthesis of Free Cyclic Carboxylic Acids A

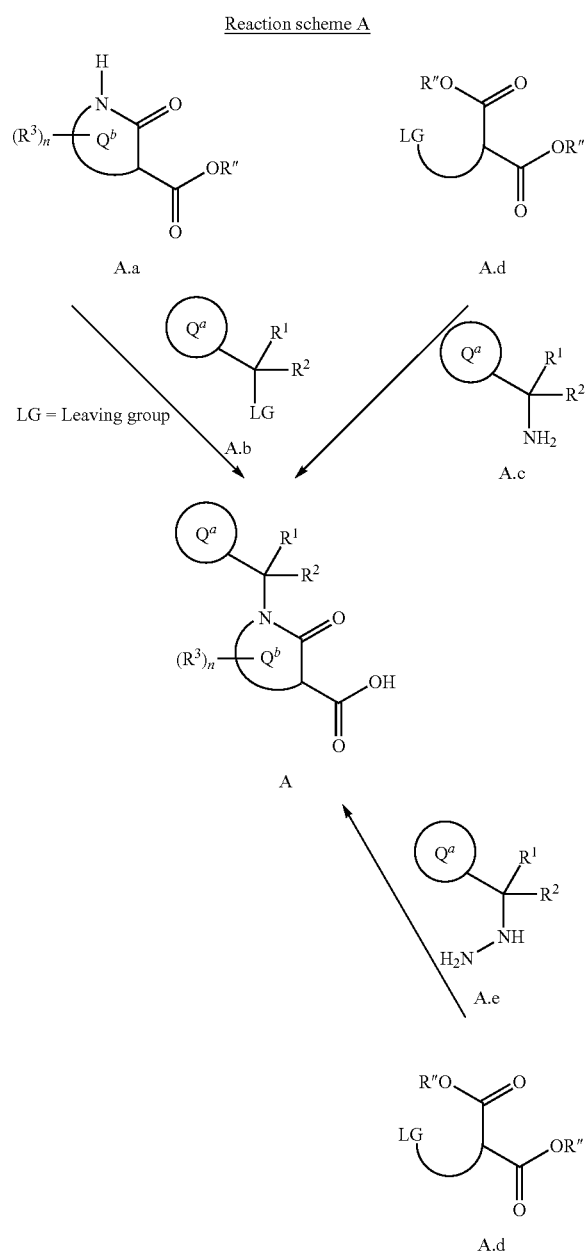

The method of synthesising the nitrogen-containing heterocyclic carboxylic acids A depends on the number and position of the cyclic nitrogens in the ring $Q^b$.

Starting from the esters A.a the grouping $Q^a$-$CR^1R^2$— may be incorporated by nucleophilic substitution at the component A.b, which is activated by an electron-withdrawing leaving group LG, e.g. a halogen, triflate or mesylate. A.a is optionally deprotonated for this purpose by the addition of a base.

A pyridazinone ring system ($Q^b$=pyridazinone) is synthesised starting from pyruvic acid derivatives which are cyclised with cyanoacetohydrazides. Subsequent saponification of the nitrile yields the corresponding carboxylic acid (*Helv. Chim. Acta*, 1954, 37, 1467), which after esterification yields the desired pyridazinonecarboxylic acid ester A.a. This is reacted in a nucleophilic substitution with A.b and subsequently saponified to form the desired carboxylic acid A.

A pyrimidinone ring system ($Q^b$=pyrimidinone) is synthesised by cyclisation of malonic acid diester derivatives with amidines. The pyrimidinonecarboxylic acid ester A.a obtained is reacted in a nucleophilic substitution with A.b and subsequently saponified to form the desired carboxylic acid A (WO 2010/007114, WO 2010/007116).

A pyridinone ring system ($Q^b$=pyridinone) is synthesised starting from malonic acid diester derivatives A.d. The derivatives used are di- and trielectrophiles, which cyclise when reacted with amines A.c (WO 2010/007114, WO 2010/007116).

A pyrazinone ring system ($Q^b$=pyrazinone) is synthesised starting from glyoxal derivatives and aminomalonamide amidines. First of all the corresponding amino-pyrazinecarboxamides are obtained, which are saponified to form the carboxylic acid. After hydrolysis of the amine by diazotisation and esterification of the carboxylic acid the desired pyrazinone ring system A.a is obtained (*J. Am. Chem. Soc.*, 1959, 81, 2472-4). This is reacted in a nucleophilic substitution with A.b and then saponified to form the desired carboxylic acid A.

A pyrazolone ring system ($Q^b$=pyrazolone) is obtained starting from malonic acid diester derivatives A.d, which cyclise with hydrazines A.e. The group LG is not a leaving group in the true sense but an electrophilic group, particularly a carbonyl, to which the hydrazine is added.

Using the methods of synthesis described above, starting from the cyclic carboxylic acid esters A.a or their precursors A.d after reaction with A.b or A.c, first of all carboxylic acid esters A* are obtained. These are each saponified to form the free acid A. In the grouping —COOR", it is possible to have groups R" which make this saponification easy and gentle. Such groups include in particular methyl, ethyl, tert-butyl and benzyl esters, wherein others are known to the skilled man from their general specialist knowledge.

The required educts A.b, A.c and A.e, as well as A.a and A.d, are commercially obtainable, already described in the literature or may be prepared analogously to published methods.

Method for Synthesising A.1

Method for Synthesising A.25

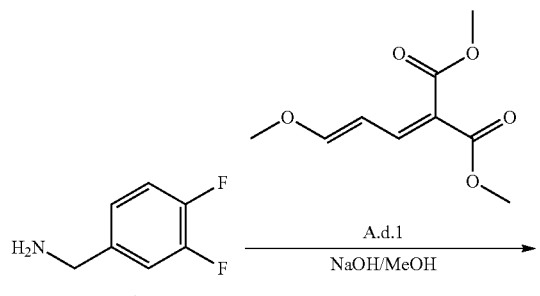

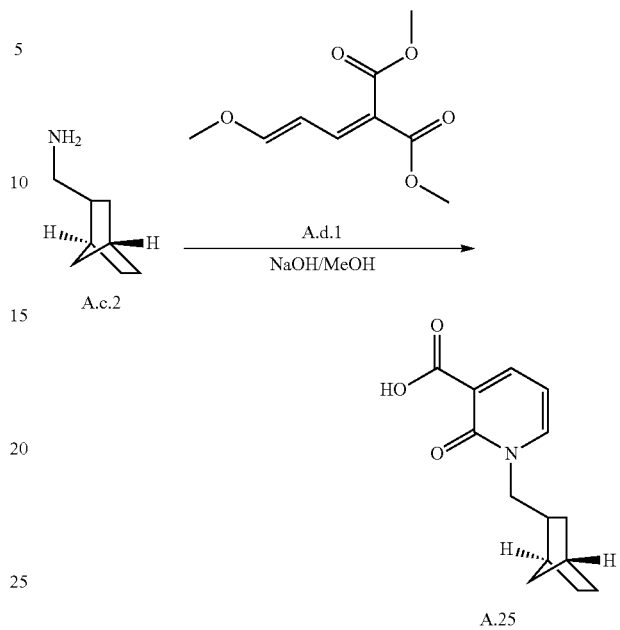

Malonic acid diester derivative A.d.1 (5.00 g, 25.0 mmol) is taken up in 40 mL 2-butanol, cooled to 5° C. and mixed with amine A.c.1 (3.00 mL, 25.1 mmol), which has been taken up in 10 mL 2-butanol. The reaction mixture is stirred for 1 h at 20° C., diluted with a further 150 mL of 2-butanol and heated to 100° C. for 48 h. Then the reaction mixture is combined with 50 mL 2 N aqueous sodium hydroxide solution and 50 mL 2 N methanolic sodium hydroxide solution and stirred for 2 h at 20° C. The reaction mixture is acidified with HCl (50 mL, 1 N) and extracted with DCM (3×50 mL), dried on MgSO$_4$, filtered, the solvent is eliminated in vacuo and A.1 (6.08 g, 90%; MS (M+H)$^+$=266; $t_{Ret.}$=0.00 min; method LCMSBAS1) is obtained.

Malonic acid diester derivative A.d.1 (115 mg, 0.55 mmol) is taken up in MeOH (1 mL), combined with amine A.c.2 (69 mg, 0.55 mmol) and DIPEA (0.3 mL) and stirred for 2 h at 130° C. Then the reaction mixture is combined with 5 mL of 2 N aqueous sodium hydroxide solution and 5 mL 2 N methanolic sodium hydroxide solution and stirred for 24 h at 20° C. The reaction mixture is acidified with HCl (5 mL, 1 N), extracted with DCM (3×50 mL), dried on MgSO$_4$, filtered, the solvent is eliminated in vacuo and A.25 (119 mg, 87%; (MS (M+H)$^+$=248; $t_{Ret.}$=1.051 min; method 1_FEC) is obtained.

Compounds A.2-A.31 are prepared analogously to A.1 or A.25 (Table 1):

| # | Structure | MS (M ± H)$^+$; $t_{Ret.}$ HPLC [min] | HPLC method |
|---|---|---|---|
| A.1 | 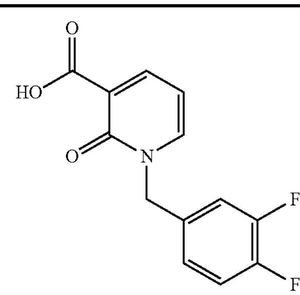 | M + H = 266; $t_{Ret.}$ = 0.00 | LCMSBAS1 |
| A.2 | 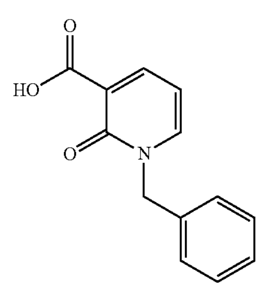 [SMILES: O=C(O)c1cccn(Cc2ccccc2)c1=O] | M – H = 228; $t_{Ret.}$ = 0.00 | LCMSBAS1 |

-continued

| # | Structure | MS (M ± H)+; t$_{Ret.}$ HPLC [min] | HPLC method |
|---|---|---|---|
| A.3 | 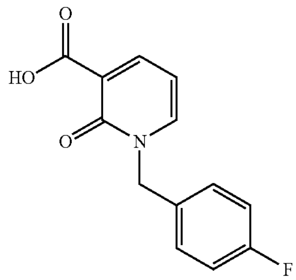 [SMILES: O=C(O)c1cccn(Cc2ccc(F)cc2)c1=O] | M − H = 246; t$_{Ret.}$ = 0.00 | LCMSBAS1 |
| A.4 | 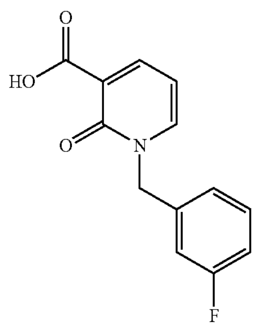 [SMILES: O=C(O)c1cccn(Cc2cccc(F)c2)c1=O] | M − H = 246; t$_{Ret.}$ = 0.00 | LCMSBAS1 |
| A.5 | 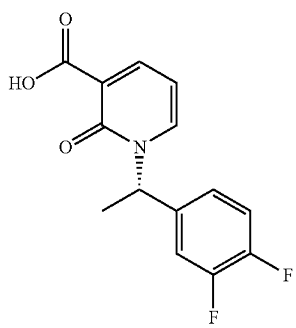 [SMILES: C[C@@H](c1ccc(F)c(F)c1)n1cccc(C(=O)O)c1=O] | M − H = 278; t$_{Ret.}$ = 0.50 | LCMSBAS1 |
| A.6 | 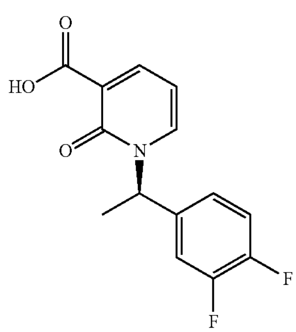 [SMILES: C[C@H](c1ccc(F)c(F)c1)n1cccc(C(=O)O)c1=O] | M + H = 280; t$_{Ret.}$ = 0.43 | 1_BAS_MeOH_POS |
| A.7 | 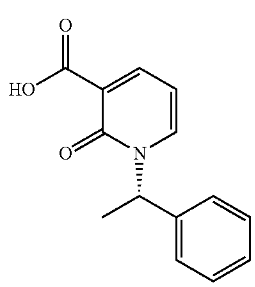 [SMILES: C[C@@H](c1ccccc1)n1cccc(C(=O)O)c1=O] | M + H = 244; t$_{Ret.}$ = 0.42 | 1_BAS_MeOH_POS |

-continued

| # | Structure | MS (M ± H)+; t_Ret. HPLC [min] | HPLC method |
|---|---|---|---|
| A.8 | 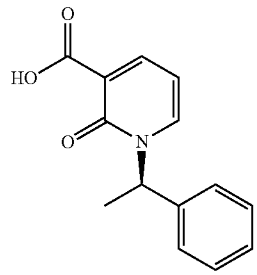 [SMILES: C[C@H](c1ccccc1)n1cccc(C(=O)O)c1=O] | M + H = 244; t_Ret. = 0.40 | 1_BAS_MeOH_POS |
| A.9 | 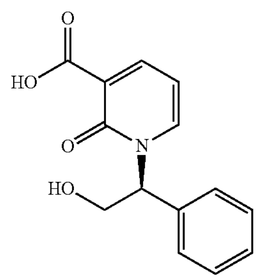 [SMILES: O=C(O)c1cccn([C@H](CO)c2ccccc2)c1=O] | M + H = 260; t_Ret. = 0.20 | 1_BAS_MeOH_POS |
| A.10 | 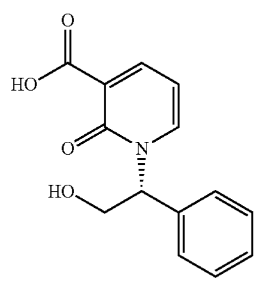 [SMILES: O=C(O)c1cccn([C@@H](CO)c2ccccc2)c1=O] | M + H = 260; t_Ret. = 0.20 | 1_BAS_MeOH_POS |
| A.11 | 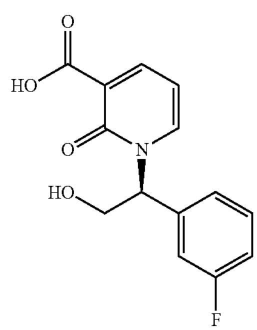 [SMILES: O=C(O)c1cccn([C@H](CO)c2cccc(F)c2)c1=O] | M + H = 278; t_Ret. = 0.00 | LCMSBAS1 |
| A.12 | 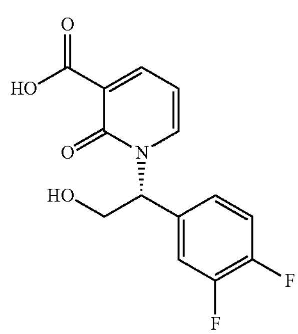 [SMILES: O=C(O)c1cccn([C@@H](CO)c2ccc(F)c(F)c2)c1=O] | M + H = 296; t_Ret. = 0.00 | LCMSBAS1 |

-continued

| # | Structure | MS (M ± H)+; t_Ret. HPLC [min] | HPLC method |
|---|---|---|---|
| A.13 | 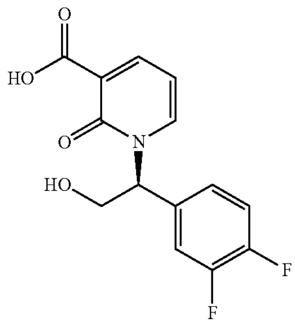 [SMILES: O=C(O)c1cccn([C@H](CO)c2ccc(F)c(F)c2)c1=O] | M + H = 296; t_Ret. = 0.00 | LCMSBAS1 |
| A.14 | 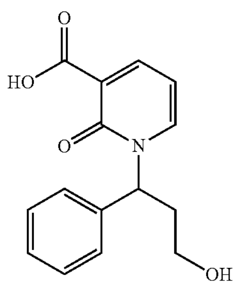 [SMILES: O=C(O)c1cccn(C(CCO)c2ccccc2)c1=O] | M + H = 274; t_Ret. = 0.27 | 1_BAS_MeOH_POS |
| A.15 | 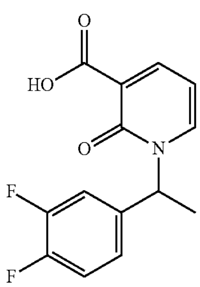 [SMILES: CC(c1ccc(F)c(F)c1)n1cccc(C(=O)O)c1=O] | M + H = 280; t_Ret. = 0.48 | 1_BAS_MeOH_POS |
| A.16 | 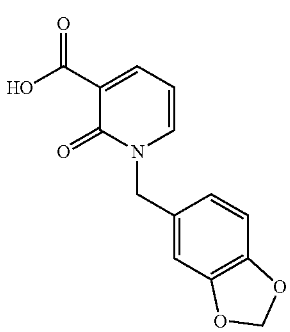 [SMILES: O=C(O)c1cccn(Cc2ccc3c(c2)OCO3)c1=O] | M + H = 274; t_Ret. = 0.24 | 1_BAS_MeOH_POS |
| A.17 | 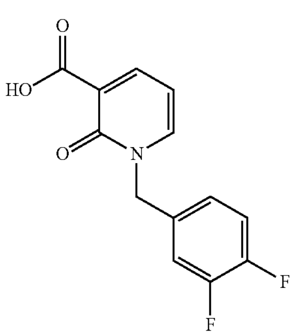 [SMILES: O=C(O)c1cccn(Cc2ccc(F)c(F)c2)c1=O] | M + H = 266; t_Ret. = 0.00 | LCMSBAS1 |

-continued

| # | Structure | MS (M ± H)±; t_Ret. HPLC [min] | HPLC method |
|---|---|---|---|
| A.18 | 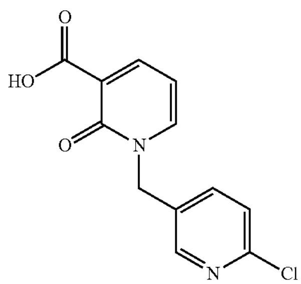 [SMILES: O=C(O)c1cccn(Cc2ccc(Cl)nc2)c1=O] | M + H = 265; t_Ret. = 1.66 | FECS |
| A.19 | 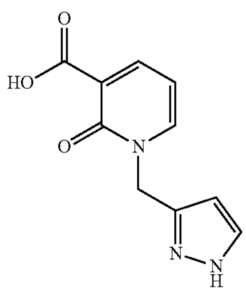 [SMILES: O=C(O)c1cccn(Cc2cc[nH]n2)c1=O] | M + H = 220; t_Ret. = 0.10 | 1_BAS_MeOH_POS |
| A.20 | 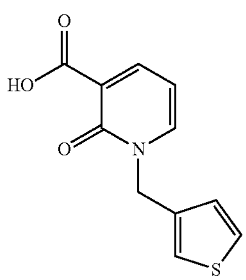 [SMILES: O=C(O)c1cccn(Cc2ccsc2)c1=O] | M − H = 234; t_Ret. = 0.00 | LCMSBAS1 |
| A.21 | 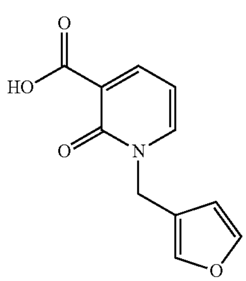 [SMILES: O=C(O)c1cccn(Cc2ccoc2)c1=O] | M − H = 218; t_Ret. = 0.00 | LCMSBAS1 |
| A.22 | 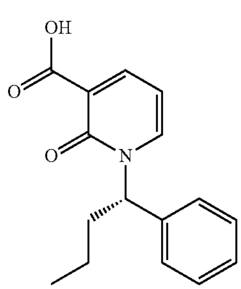 [SMILES: CCC[C@@H](c1ccccc1)n1cccc(C(=O)O)c1=O] | M − H = 272; t_Ret. = 0.71 | 1_BAS_MeOH_POS |

-continued

| # | Structure | MS (M ± H)⁺; $t_{Ret.}$ HPLC [min] | HPLC method |
|---|---|---|---|
| A.23 | [structure: 1-[(1S)-1-(3,4-difluorophenyl)ethyl]-2-oxo-1,2-dihydropyridine-3-carboxylic acid] | M − H = 278; $t_{Ret.}$ = 0.50 | LCMSBAS1 |
| A.24 | [structure: 2-oxo-1-[(1R)-1-phenylethyl]-1,2-dihydropyridine-3-carboxylic acid] | M + H = 244; $t_{Ret.}$ = 0.42 | 1_BAS_MeOH_POS |
| A.25 | [structure: 1-(bicyclo[2.2.1]heptan-2-ylmethyl)-2-oxo-1,2-dihydropyridine-3-carboxylic acid] | M + H = 248; $t_{Ret.}$ = 1.051 | 1_FEC |
| A.26 | [structure: 2-oxo-1-[(tetrahydro-2H-pyran-4-yl)methyl]-1,2-dihydropyridine-3-carboxylic acid] | M + H = 238; $t_{Ret.}$ = 0.495 | 1_FEC |
| A.27 | [structure: 2-oxo-1-[(tetrahydro-2H-pyran-2-yl)methyl]-1,2-dihydropyridine-3-carboxylic acid] | M + H = 238; $t_{Ret.}$ = 0.50 | 1_FEC |

-continued
| # | Structure | MS (M ± H)+; $t_{Ret.}$ HPLC [min] | HPLC method |
|---|---|---|---|
| A.28 | 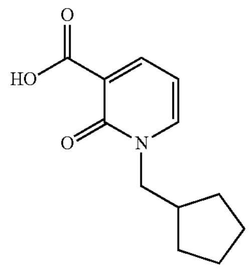 [SMILES: O=C(O)c1cccn(CC2CCCC2)c1=O] | M + H = 222; $t_{Ret.}$ = 0.91 | 1_FEC |
| A.29 | 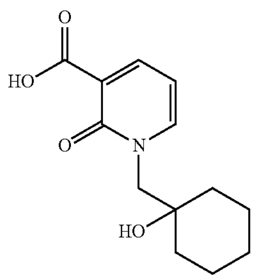 [SMILES: O=C(O)c1cccn(CC2(O)CCCCC2)c1=O] | M + H = 252; $t_{Ret.}$ = 0.692 | 1_FEC |
| A.30 | 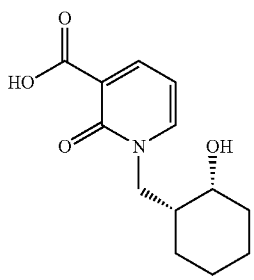 [SMILES: O=C(O)c1cccn(C[C@H]2CCCC[C@H]2O)c1=O] | M + H = 252; $t_{Ret.}$ = 0.657 | 1_FEC |
| A.31 | 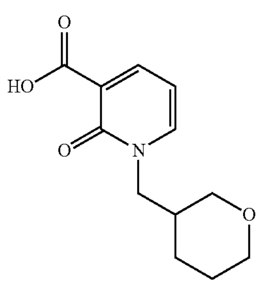 [SMILES: O=C(O)c1cccn(CC2CCCOC2)c1=O] | M + H = 238; $t_{Ret.}$ = 0.544 | 1_FEC |
Method for Synthesising A.32
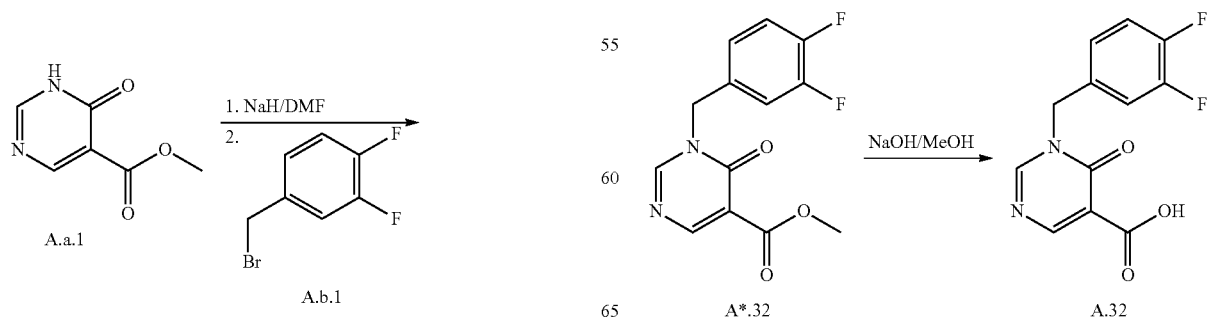

Sodium hydride (60%; 1.40 g, 36.0 mmol) is placed in DMF (70 mL), carboxylic acid ester A.a.1 (5.00 g, 32.0 mmol) is added and the mixture is stirred for 45 min at 20° C. Then benzylbromide A.b.1 (4.10 mL, 32.0 mmol) is metered in and the mixture is stirred for a further 3 h at 20° C. The reaction mixture is combined with HCl (50 mL, 1 N) and DCM (50 mL), the organic phase is separated off and extracted again with HCl (2×30 mL). Then the organic phase is dried, the solvent is eliminated in vacuo and carboxylic acid ester A*.32 (10.0 g, 89%; HPLC-MS: MS (M+H)$^+$=281; $t_{Ret.}$=1.57 min; method FEC3) is obtained.

Carboxylic acid ester A*.32 (1.9 g, 5.6 mmol) is taken up in MeOH (7.3 mL) and combined with NaOH (6.2 mL, 1 M). After 16 h at 20° C. the mixture is diluted with water and extracted with DCM. The organic phase is discarded, the aqueous phase is acidified and extracted with DCM. The organic phase is dried on Na$_2$SO$_4$, filtered, the solvent is eliminated in vacuo and the free carboxylic acid A.32 (694 mg, 47%; HPLC-MS: MS (M+H)$^+$=267; $t_{Ret.}$=0.29 min; method FECB4) is obtained.

Method for Synthesising A.33

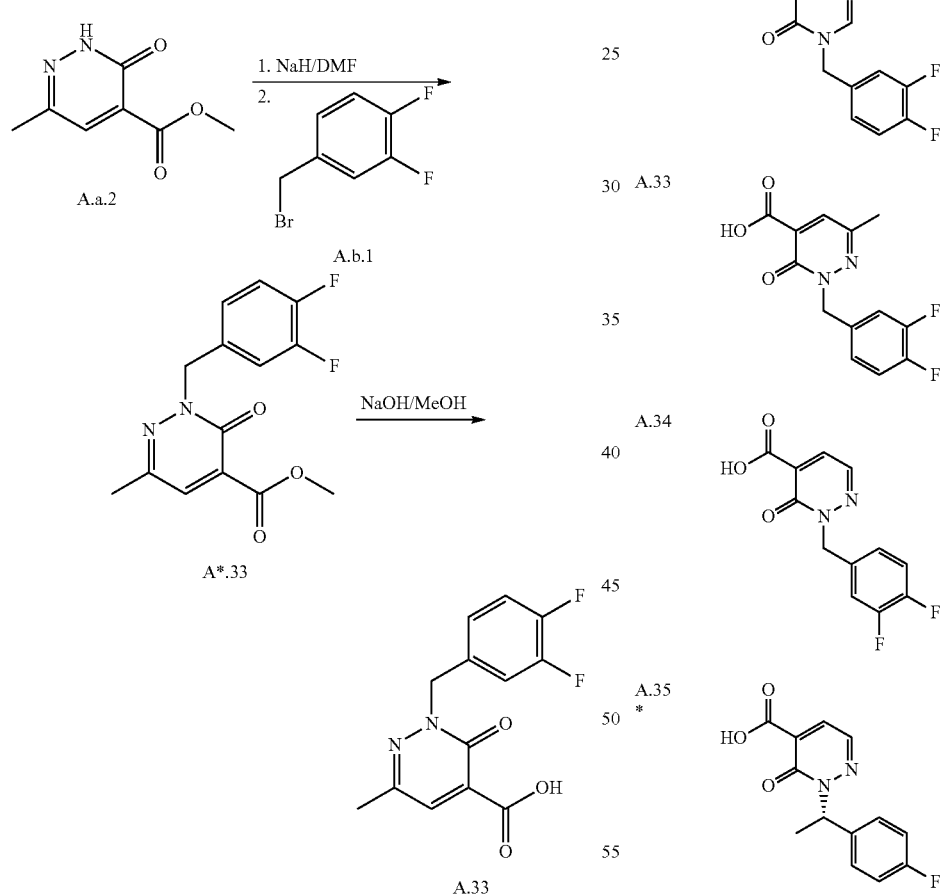

Sodium hydride (60%; 105 mg, 2.60 mmol) is placed in DMF (1.50 mL), combined with carboxylic acid ester A.a.2 (400 mg, 2.40 mmol) and stirred for 45 min at 20° C.

Then benzylbromide A.b.1 (0.31 mL, 2.4 mmol) is metered in and the mixture is stirred for a further 48 h at 20° C. The reaction mixture is combined with HCl (50 mL, 1 N) and DCM (50 mL), the organic phase is separated off and extracted again with HCl (2×30 mL). Then the organic phase is dried, the solvent is eliminated in vacuo and carboxylic acid ester A*.33 (487 mg, 69%; HPLC-MS: MS (M+H)$^+$=295; $t_{Ret.}$=2.09 min; method AFEC) is obtained.

Carboxylic acid ester A*.33 (487 mg, 1.71 mmol) is taken up in MeOH (4.0 mL) and combined with NaOH (2.0 mL, 1 N). After 2 h at 20° C. the mixture is diluted with water and extracted with DCM. The organic phase is discarded, the aqueous phase is acidified and extracted with DCM. The organic phase is dried on Na$_2$SO$_4$, the solvent is eliminated in vacuo and the free carboxylic acid A.33 (HPLC-MS: MS (M–H)$^-$=279; $t_{Ret.}$=0.00 min; method LCMSBAS1) is obtained.

Compounds A.34-A.40 are prepared analogously to compound A.32 or A.33 and if necessary subjected to chiral chromatography before the saponification (Table 2):

| # | Structure | MS (M ± H)$^+$; $t_{Ret.}$ HPLC [min] | HPLC method |
|---|---|---|---|
| A.32 | 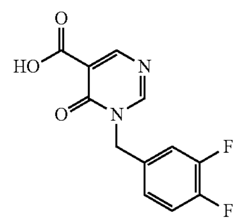 [SMILES: O=C(O)c1cncn(Cc2ccc(F)c(F)c2)c1=O] | M + H = 267; $t_{Ret.}$ = 0.29 | FECB4 |
| A.33 | 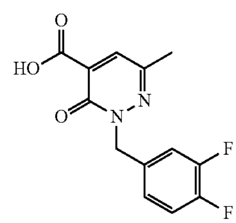 [SMILES: Cc1cc(C(=O)O)c(=O)n(Cc2ccc(F)c(F)c2)n1] | M – H = 279; $t_{Ret.}$ = 0.00 | LCMSBAS1 |
| A.34 | 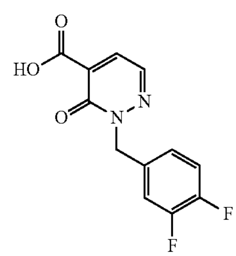 [SMILES: O=C(O)c1ccnn(Cc2ccc(F)c(F)c2)c1=O] | M + H = 265; $t_{Ret.}$ = 0.40 | LCMSBAS1 |
| A.35 * | 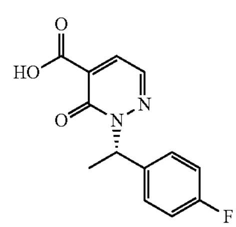 [SMILES: C[C@@H](c1ccc(F)cc1)n1nccc(C(=O)O)c1=O] | M + H = 263; $t_{Ret.}$ = 0.42 | LCMSBAS1 |
| A.36 * | 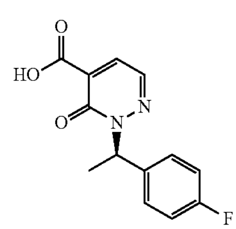 [SMILES: C[C@H](c1ccc(F)cc1)n1nccc(C(=O)O)c1=O] | M + H = 263; $t_{Ret.}$ = 0.42 | LCMSBAS1 |

-continued

| # | Structure | MS (M ± H)+; $t_{Ret.}$ HPLC [min] | HPLC method |
|---|---|---|---|
| A.37 | 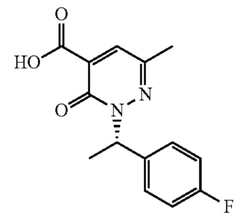 [SMILES: Cc1cc(C(=O)O)c(=O)n([C@@H](C)c2ccc(F)cc2)n1] | M + H = 277; $t_{Ret.}$ = 0.50 | LCMSBAS1 |
| A.38 * | 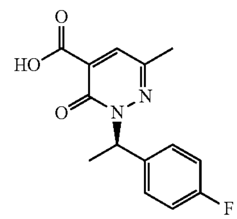 [SMILES: Cc1cc(C(=O)O)c(=O)n([C@H](C)c2ccc(F)cc2)n1] | M + H = 277; tRet. = 0.50 | LCMSBAS1 |
| A.39 * | 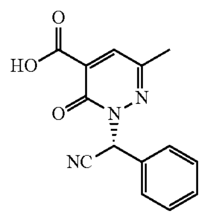 [SMILES: Cc1cc(C(=O)O)c(=O)n([C@@H](C#N)c2ccccc2)n1] | M + H = 270; $t_{Ret.}$ = 0.48 | LCMSBAS1 |
| A.40 * | 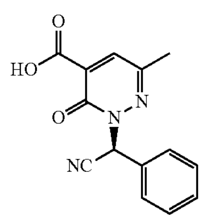 [SMILES: Cc1cc(C(=O)O)c(=O)n([C@H](C#N)c2ccccc2)n1] | M + H = 270; $t_{Ret.}$ = 0.48 | LCMSBAS1 |

* Gilson HPLC apparatus, chiral column (Daicel Chiralpack IC, 250 × 20 mm). Eluant: 35% n-heptane, 65% DCM/EtOH/diethylamine (2000:100:2.6)

Method for Synthesising A.41

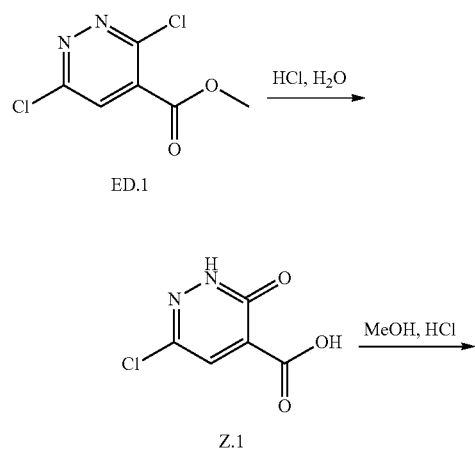

Carboxylic acid ester ED.1 (2.00 g, 10.4 mmol) is placed in dioxane (9.0 mL), combined with HCl (10.4 mL, 1 M) and stirred for 20 h at 90° C. Then the reaction mixture is cooled to 0° C., the precipitate is filtered off, washed with water and pyridazinonic acid Z.1 (955 mg, 53%; HPLC-MS: MS (M−H)−=173; $t_{Ret.}$=0.00 min; method LCMSBAS1) is obtained.

Pyridazinonic acid Z.1 (955 mg, 5.4 mmol) is placed in MeOH (6.0 mL), combined with HCl (6.0 mL, 4M in dioxane) and stirred for 20 h at 50° C. The reaction mixture is combined with H₂O and DCM, the organic phase is separated off and extracted with H₂O (2×10 mL). Then the organic phase is dried on MgSO₄, filtered off, the solvent is eliminated in vacuo and carboxylic acid ester A.a.3 (890 mg, 86%; HPLC-MS: MS (M+H)+=189; $t_{Ret.}$=1.47 min; method AFEC) is obtained.

Sodium hydride (60%; 93 mg, 2.3 mmol) is placed in DMF (1.5 mL), combined with carboxylic acid ester A.a.3 (397 mg, 2.10 mmol) and stirred for 45 min at 20° C. Then benzyl bromide A.b.1 (0.27 mL, 2.1 mmol) is metered in and the mixture is stirred for a further 2 h at 20° C. The reaction mixture is combined with HCl (5 mL, 1 N) and DCM (5 mL), the organic phase is separated off and extracted again with HCl (2×5 mL). Then the organic phase is dried on MgSO₄, filtered off, the solvent is eliminated in vacuo and carboxylic acid ester A*.41 (922 mg, 98%; HPLC-MS: MS (M+H)+=315; $t_{Ret.}$=2.2 min; method AFEC) is obtained.

Carboxylic acid ester A*.41 (470 mg, 1.00 mmol) is taken up in MeOH (3.0 mL) and combined with 1 N NaOH (1.3 mL). After 5 h at 20° C. the mixture is diluted with water and extracted with DCM. The organic phase is discarded, the aqueous phase is acidified with HCl (5 mL, 1 M) and extracted with DCM (3×5 mL). The organic phase is dried, the solvent is eliminated in vacuo and the free carboxylic acid A.41 (149 mg, 48%; HPLC-MS: MS (M−H)⁻=299; $t_{Ret.}$=0.76 min; method LCMSBAS1) is obtained.

Method for Synthesising A.42

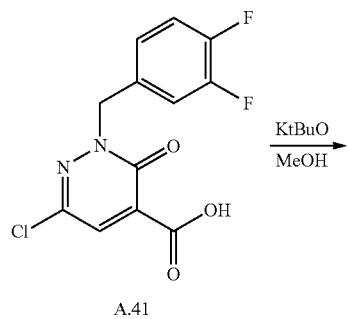

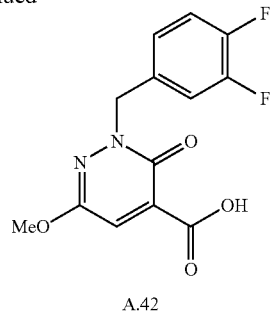

Carboxylic acid A.41 (4.00 g, 13.0 mmol) is placed in MeOH (40 mL), combined with KtBuO (30%, 3.80 g, 32.0 mmol) and heated to 160° C. for 12 min. The reaction mixture is combined with HCl (20 mL, 1 N) and DCM (30 mL), the organic phase is separated off and extracted with HCl (2×20 mL, 1 N). Then the organic phase is dried on Na₂SO₄, filtered off, the solvent is eliminated in vacuo and carboxylic acid A.42 (3.62 g, 94%; HPLC-MS: MS (M−H)⁻=295; $t_{Ret.}$=1.00 min; method 1_FEC) is obtained.

Compounds A.43 and A.44 are prepared analogously to compound A.42 (Table 3):

| # | Structure | MS (M ± H)±; $t_{Ret.}$ HPLC [min] | HPLC method |
|---|---|---|---|
| A.41 | 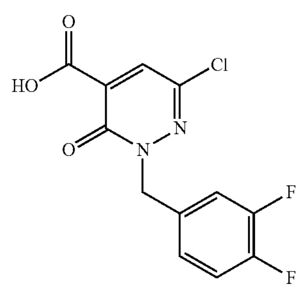 [SMILES: O=C(O)c1cc(Cl)nn(Cc2ccc(F)c(F)c2)c1=O] | M − H = 299; $t_{Ret.}$ = 0.76 | LCMSBAS1 |
| A.42 | 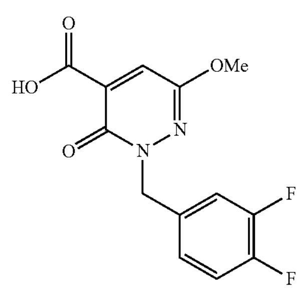 [SMILES: COc1cc(C(=O)O)c(=O)n(Cc2ccc(F)c(F)c2)n1] | M − H = 295; $t_{Ret.}$ = 1.00 | 1_FEC |
| A.43 | 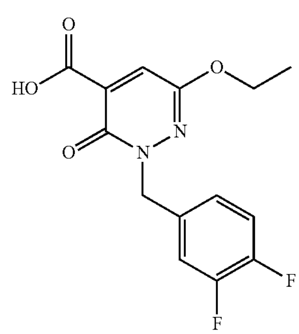 [SMILES: CCOc1cc(C(=O)O)c(=O)n(Cc2ccc(F)c(F)c2)n1] | M + H = 311; $t_{Ret.}$ = 1.14 | LCMSBAS1 |

| # | Structure | MS (M ± H)+; $t_{Ret.}$ HPLC [min] | HPLC method |
|---|---|---|---|
| A.44 | 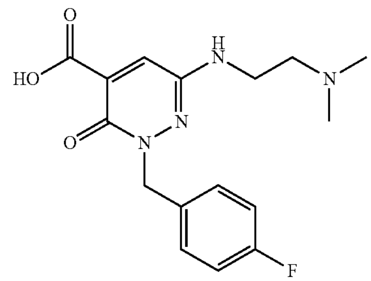 [SMILES: CN(C)CCNc1cc(C(=O)O)c(=O)n(Cc2ccc(F)cc2)n1] | M + H = 335; $t_{Ret.}$ = 1.32 | LCMSBAS1 |

Method for Synthesising A.45

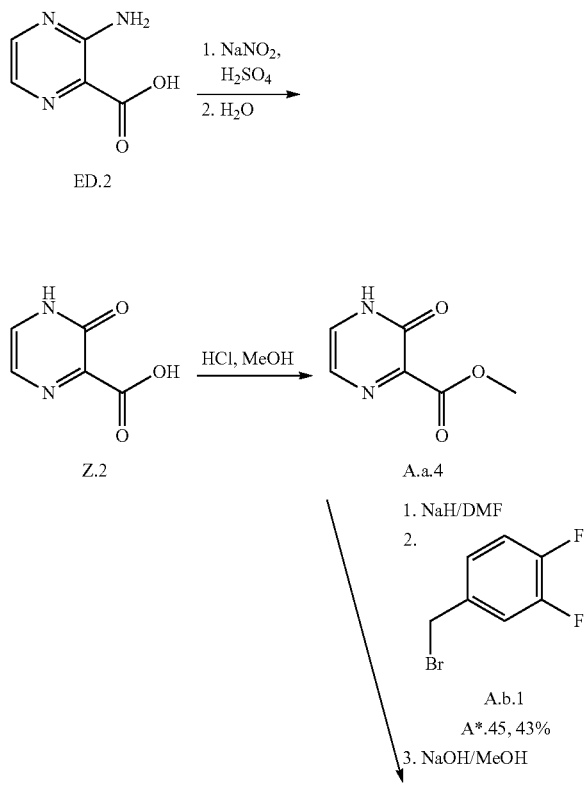

Carboxylic acid ED.2 (300 mg, 2.20 mmol) is placed in conc. $H_2SO_4$ (1.3 mL), cooled to 0° C., a mixture of $NaNO_2$ (149 mg, 2.20 mmol) in conc. $H_2SO_4$ (1.6 mL) is added dropwise and the mixture is stirred for 1 h. Then the reaction mixture is added dropwise to an ice-water mixture with vigorous stirring, the precipitate formed is filtered off and pyrazinonic acid Z.2 (200 mg, 66%; MS (M–H)$^-$=139; $t_{Ret.}$=0.00 min; method LCMSBAS1) is obtained.

Pyrazinonic acid Z.2 (200 mg, 1.4 mmol) is placed in MeOH (10 mL), combined with HCl (0.1 mL, 4 M in dioxane) and stirred for 12 h at 20° C. Then the solvent is removed and carboxylic acid ester A.a.4 (212 mg, 96%; HPLC-MS: MS (M–H)$^-$=153; $t_{Ret.}$=0.00 min; method LCMSBAS1) is obtained.

Sodium hydride (60%; 61 mg, 1.5 mmol) is placed in DMF (1.2 mL), combined with carboxylic acid ester A.a.4 (212 mg, 1.4 mmol) and stirred for 45 min at 20° C. Then benzyl bromide A.b.1 (0.18 mL, 1.4 mmol) is metered in and the mixture is stirred for a further 24 h at 20° C. The reaction mixture is combined with HCl (5 mL, 1 M) and DCM (5 mL), the organic phase is separated off and extracted with HCl (2×5 mL, 1 N). Then the organic phase is dried on $Na_2SO_4$, filtered off, the solvent is eliminated in vacuo and carboxylic acid ester A*.45 (166 mg, 43%; HPLC-MS: MS (M+H)$^+$=281; $t_{Ret.}$=1.63 min; method FECS) is obtained.

Carboxylic acid ester A*.45 (166 mg, 0.60 mmol) is taken up in MeOH (4.0 mL) and combined with NaOH (0.71 mL, 1 M). After 5 h at 20° C. the mixture is diluted with water and extracted with DCM. The organic phase is discarded, the aqueous phase is acidified with HCl (5 mL, 1 M) and extracted with DCM. The organic phase is dried on $Na_2SO_4$, filtered off, the solvent is eliminated in vacuo and the free carboxylic acid A.45 (150 mg, 95%; HPLC-MS: MS (M+H)$^+$=267; $t_{Ret.}$=1.59 min; method FECS) is obtained.

Method for Synthesising A.46 and A.47

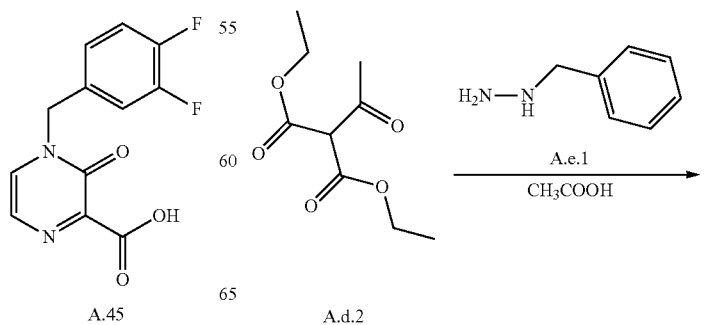

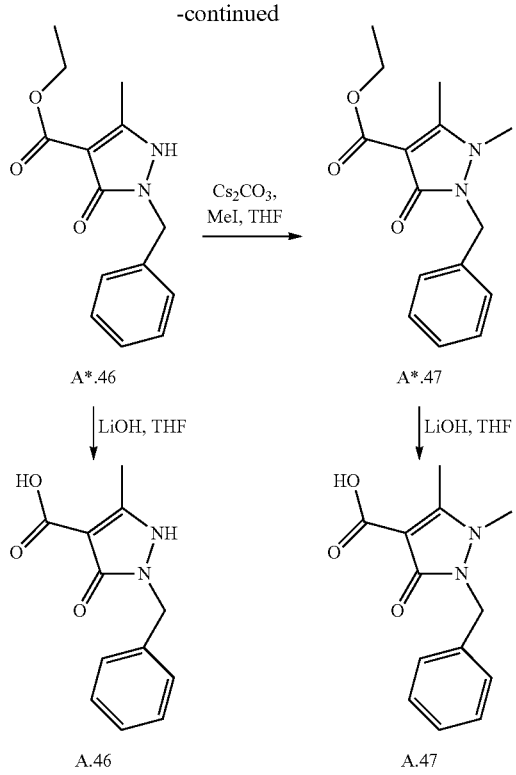

Acetyldiethyl malonate A.d.2 (100 mg 0.49 mmol) is placed in conc. acetic acid (0.5 mL) and combined with benzylhydrazine A.e.1 (97 mg, 0.49 mmol). The mixture is stirred for 3 h at 95° C. Then the solvent is removed and carboxylic acid ester A*.46 (45 mg, 35%; HPLC-MS: MS $(M+H)^+=261$; $t_{Ret.}=0.39$ min; method LCMSBAS1) is obtained.

Carboxylic acid ester A*.46 (22 mg, 0.09 mmol) is placed in THF (0.3 mL) and combined with $Cs_2CO_3$ (30 mg, 0.09 mmol). After 15 min at 20° C. MeI (5 μL, 0.09 mmol) is added and the mixture is stirred for a further 16 h at 20° C. After elimination of the solvent carboxylic acid ester A*.47 (15 mg, 65%; HPLC-MS: MS $(M+H)^*=275$; $t_{Ret.}=1.24$ min; method LCMSBAS1) is obtained.

Carboxylic acid ester A*.47 (35 mg, 0.13 mmol) is placed in THF (0.6 mL), combined with NaOH (0.5 mL, 1 N) and stirred for 4 h at 50° C. The reaction mixture is combined with HCl (3 mL, 1 N) and DCM, the organic phase is separated off, extracted with HCl (2×5 mL, 1 N), dried, the solvent is eliminated in vacuo and carboxylic acid A.47 (31 mg, 99%; HPLC-MS: MS $(M+H)^+=247$; $t_{Ret}=1.59$ min; method FSUN) is obtained.

Compounds A.48-A.53 are prepared analogously to compound A.47 and if necessary subjected to chiral chromatography before the saponification (Table 4):

| # | Structure | MS $(M + H)^+$; $t_{Ret.}$ HPLC [min] | HPLC method |
|---|---|---|---|
| A.46 | 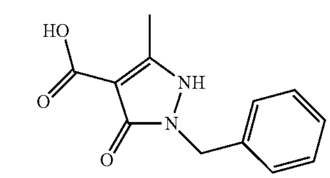 [SMILES: Cc1[nH]n(Cc2ccccc2)c(=O)c1C(=O)O] | n.a. | — |
| A.47 | 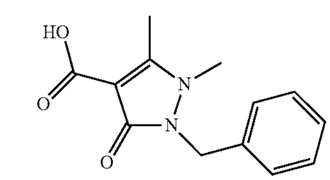 [SMILES: Cc1c(C(=O)O)c(=O)n(Cc2ccccc2)n1C] | M + H = 247; $t_{Ret.}$ = 1.59 | FSUN |
| A.48 | 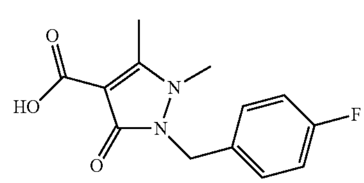 [SMILES: Cc1c(C(=O)O)c(=O)n(Cc2ccc(F)cc2)n1C] | M + H = 265; $t_{Ret.}$ = 1.77 | FECS2 |
| A.49 | 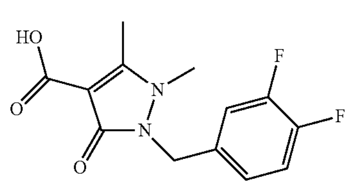 [SMILES: Cc1c(C(=O)O)c(=O)n(Cc2ccc(F)c(F)c2)n1C] | M + H = 283; $t_{Ret.}$ = 0.39 | LCMSBAS1 |

-continued

| # | Structure | MS (M + H)+; $t_{Ref.}$ HPLC [min] | HPLC method |
|---|---|---|---|
| A.50 | 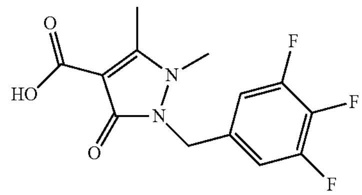 [SMILES: Cc1c(C(=O)O)c(=O)n(Cc2cc(F)c(F)c(F)c2)n1C] | M + H = 301; $t_{Ref.}$ = 0.39 | LCMSBAS1 |
| A.51* | 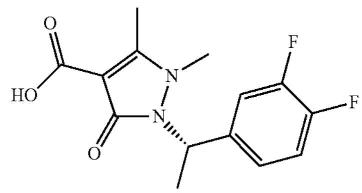 [SMILES: Cc1c(C(=O)O)c(=O)n([C@@H](C)c2ccc(F)c(F)c2)n1C] | M + H = 297; $t_{Ref.}$ = 0.40 | LCMSBAS1 |
| A.52* | 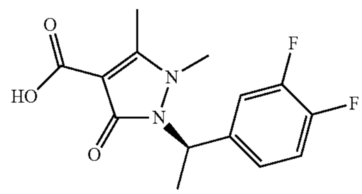 [SMILES: Cc1c(C(=O)O)c(=O)n([C@H](C)c2ccc(F)c(F)c2)n1C] | M + H = 297; $t_{Ref.}$ = 0.40 | LCMSBAS1 |
| A.53 | 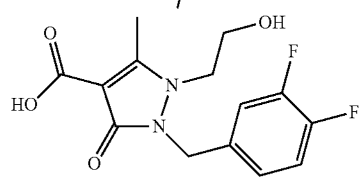 | M + H = 313; $t_{Ref.}$ = 0.56 | 1_FEC |

*Gilson HPLC apparatus, chiral column (Daicel Chiralpack IC, 250 × 20 mm). Eluant: 35% n-heptane, 65% DCM/EtOH/diethylamine (2000:100:2.6)

b) Synthesis of Propargylamides C

Reaction scheme B

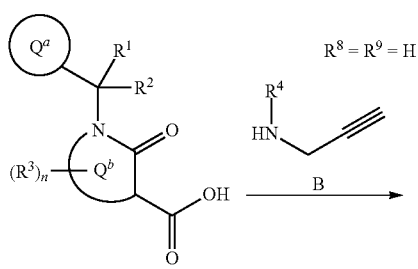

The amides C required are synthesised by coupling a propargylamine B with the carboxylic acid A. The amide coupling is assisted by coupling reagents such as for example DCC, DIC, TBTU, HATU, EDC or the like, or the formation of the corresponding acid chloride.

The synthesis components which are to be used in the above reaction schemes are optionally provided with common protective groups when used. Therefore, additional intermediate steps may be needed to eliminate these protective groups.

With regard to the feasibility of the reaction methods illustrated and described in the above reaction schemes reference is made to WO 2008/005457. In the cited specification, pyridinonecarboxylic acids A are amidated in a variety of ways.

Method for Synthesising C.1

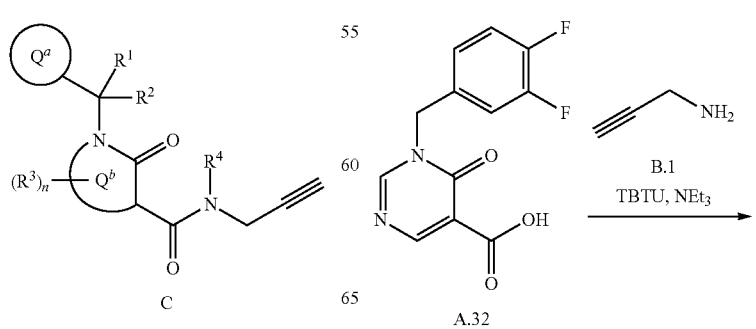

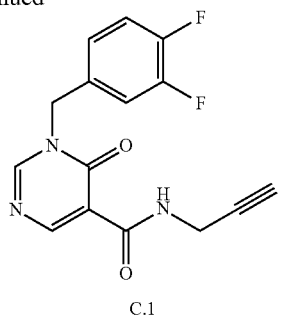

C.1

Carboxylic acid A.32 (1.00 g, 3.75 mmol) is placed in DCM (10 mL), combined with TBTU (1.73 g, 5.36 mmol), propargylamine B.1 (0.29 mL, 4.10 mmol) and NEt$_3$ (1.3 mL, 9.5 mmol) and stirred for 12 h at 20° C. The reaction mixture is combined with water and DCM, the organic phase is separated off and extracted 2× with water. Then the organic phase is dried on Na$_2$SO$_4$, the solvent is eliminated in vacuo, the crude product is purified by chromatography (90:10 to 60:40 in 12 min H$_2$O/CH$_3$CN) and carboxylic acid amide C.1 (940 mg, 83%; HPLC-MS: MS (M+H)$^+$=304; t$_{Ret.}$=1.45 min; method LCMSBAS1) is obtained.

Propargylamides C.2-C.40 are prepared analogously to propargylamide C.1 (Table 5).

| # | Structure | MS (M + H)$^+$; t$_{Ret.}$ HPLC [min] | HPLC method |
|---|---|---|---|
| C.1 | 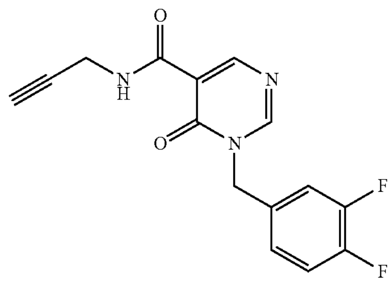 [SMILES: C#CCNC(=O)c1cncn(Cc2ccc(F)c(F)c2)c1=O] | M + H = 304; t$_{Ret.}$ = 1.45 | LCMSBAS1 |
| C.2 | 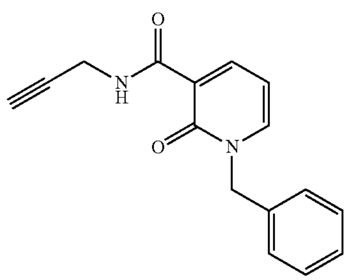 [SMILES: C#CCNC(=O)c1cccn(Cc2ccccc2)c1=O] | M + H = 267; t$_{Ret.}$ = 1.43 | LCMSBAS1 |
| C.3 | 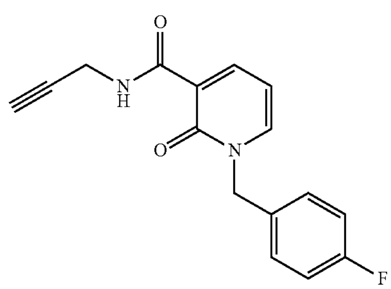 [SMILES: C#CCNC(=O)c1cccn(Cc2ccc(F)cc2)c1=O] | M + H = 285; t$_{Ret.}$ = 1.42 | LCMSBAS1 |
| C.4 | 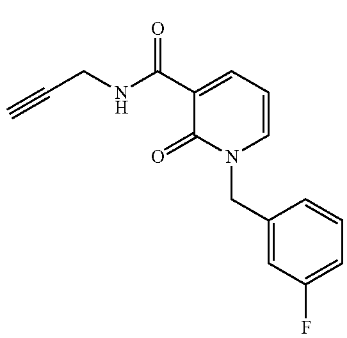 [SMILES: C#CCNC(=O)c1cccn(Cc2cccc(F)c2)c1=O] | M + H = 285; t$_{Ret.}$ = 1.45 | LCMSBAS1 |

-continued

| # | Structure | MS (M + H)+; $t_{Ret.}$ HPLC [min] | HPLC method |
|---|---|---|---|
| C.5 | 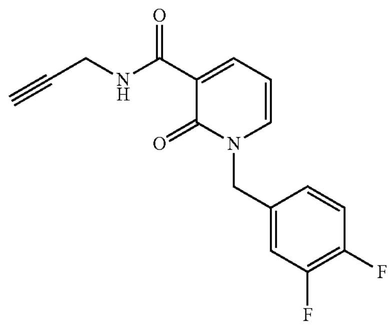 [SMILES: C#CCNC(=O)c1cccn(Cc2ccc(F)c(F)c2)c1=O] | M + H = 303; $t_{Ret.}$ = 1.53 | LCMSBAS1 |
| C.6 | 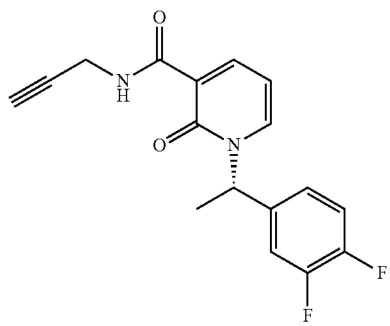 [SMILES: C#CCNC(=O)c1cccn([C@@H](C)c2ccc(F)c(F)c2)c1=O] | M + H = 317; $t_{Ret.}$ = 1.66 | LCMSBAS1 |
| C.7 | 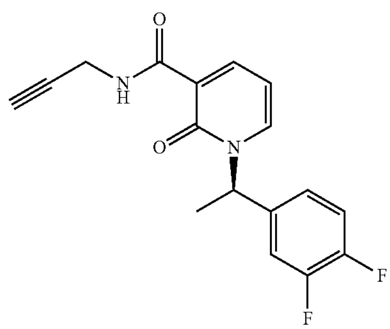 [SMILES: C#CCNC(=O)c1cccn([C@H](C)c2ccc(F)c(F)c2)c1=O] | M + H = 317; $t_{Ret.}$ = 1.66 | LCMSBAS1 |
| C.8 | 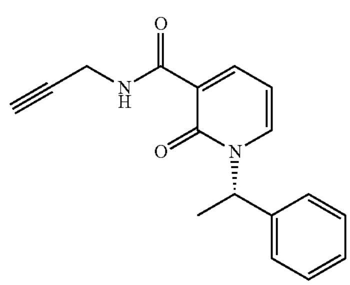 [SMILES: C#CCNC(=O)c1cccn([C@@H](C)c2ccccc2)c1=O] | M + H = 281; $t_{Ret.}$ = 1.53 | LCMSBAS1 |
| C.9 | 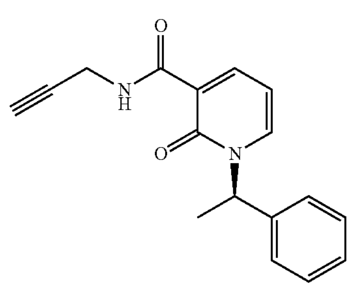 [SMILES: C#CCNC(=O)c1cccn([C@H](C)c2ccccc2)c1=O] | M + H = 281; $t_{Ret.}$ = 1.53 | LCMSBAS1 |

-continued

| # | Structure | MS (M + H)+; $t_{Ret.}$ HPLC [min] | HPLC method |
|---|---|---|---|
| C.10 | 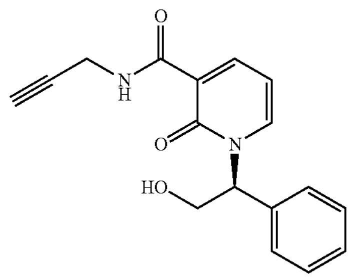 [SMILES: C#CCNC(=O)c1cccn([C@H](CO)c2ccccc2)c1=O] | M + H = 297; $t_{Ret.}$ = 1.31 | 1_FEC |
| C.11 | 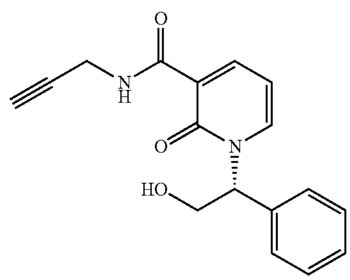 [SMILES: C#CCNC(=O)c1cccn([C@@H](CO)c2ccccc2)c1=O] | M + H = 297; $t_{Ret.}$ = 1.31 | 1_FEC |
| C.12 | 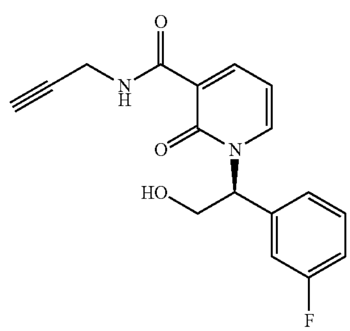 [SMILES: C#CCNC(=O)c1cccn([C@H](CO)c2cccc(F)c2)c1=O] | M + H = 315; $t_{Ret.}$ = 1.33 | LCMSBAS1 |
| C.13 | 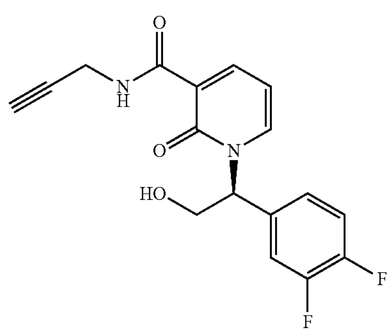 [SMILES: C#CCNC(=O)c1cccn([C@H](CO)c2ccc(F)c(F)c2)c1=O] | M + H = 333; $t_{Ret.}$ = 1.42 | LCMSBAS1 |
| C.14 | 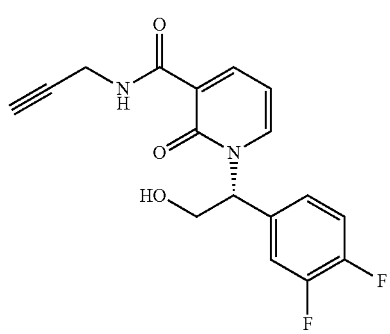 [SMILES: C#CCNC(=O)c1cccn([C@@H](CO)c2ccc(F)c(F)c2)c1=O] | M + H = 333; $t_{Ret.}$ = 1.42 | LCMSBAS1 |

-continued

| # | Structure | MS (M + H)+; $t_{Ret.}$ HPLC [min] | HPLC method |
|---|---|---|---|
| C.15 | 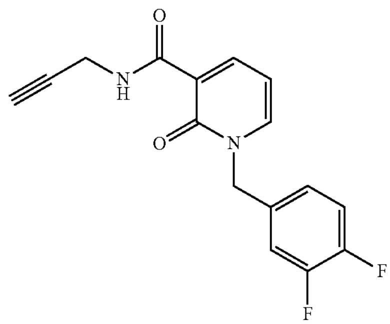 [SMILES: C#CCNC(=O)c1cccn(Cc2ccc(F)c(F)c2)c1=O] | M + H = 303; $t_{Ret.}$ = 1.52 | LCMSBAS1 |
| C.16 | 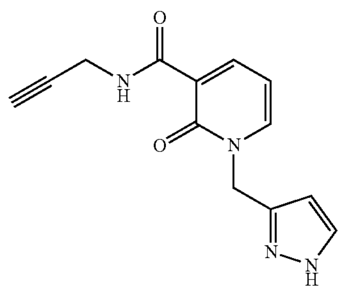 [SMILES: C#CCNC(=O)c1cccn(Cc2cc[nH]n2)c1=O] | M − H = 255; $t_{Ret.}$ = 0.86 | LCMSBAS1 |
| C.17 | 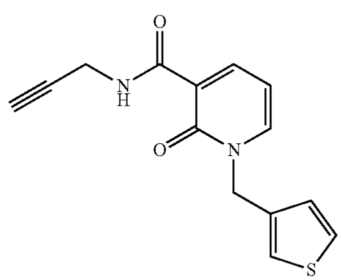 [SMILES: C#CCNC(=O)c1cccn(Cc2ccsc2)c1=O] | M + H = 273; $t_{Ret.}$ = 1.35 | LCMSBAS1 |
| C.18 | 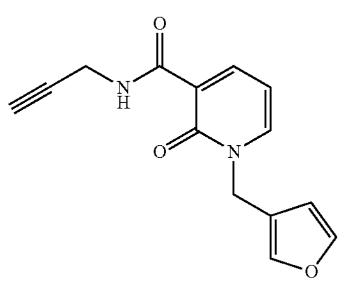 [SMILES: C#CCNC(=O)c1cccn(Cc2ccoc2)c1=O] | M + H = 257; $t_{Ret.}$ = 0.72 | 1_FEC |
| C.19 | 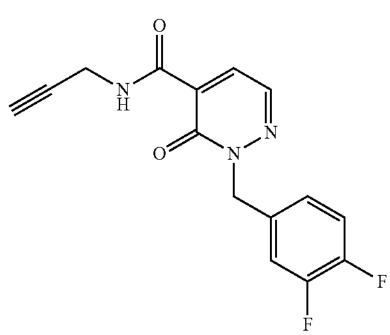 [SMILES: C#CCNC(=O)c1ccnn(Cc2ccc(F)c(F)c2)c1=O] | M + H = 304; $t_{Ret.}$ = 1.66 | LCMSBAS1 |

-continued

| # | Structure | MS (M + H)+; t_Ret. HPLC [min] | HPLC method |
|---|---|---|---|
| C.20 | 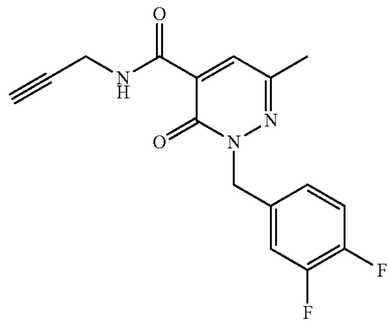 [SMILES: C#CCNC(=O)c1cc(C)nn(Cc2ccc(F)c(F)c2)c1=O] | M + H = 318; $t_{Ret.}$ = 1.73 | LCMSBAS1 |
| C.21 | 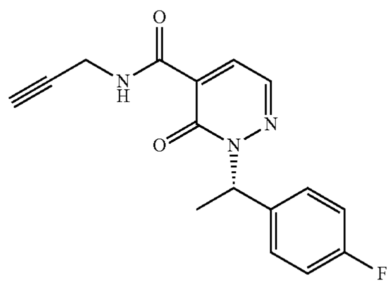 [SMILES: C#CCNC(=O)c1ccnn([C@@H](C)c2ccc(F)cc2)c1=O] | M + H = 300; $t_{Ret.}$ = 1.68 | LCMSBAS1 |
| C.22 | 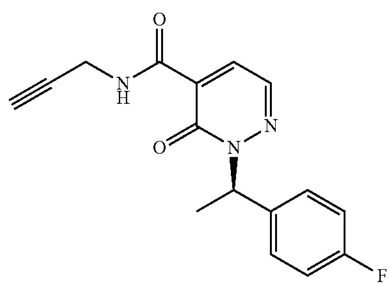 [SMILES: C#CCNC(=O)c1ccnn([C@H](C)c2ccc(F)cc2)c1=O] | M + H = 300; $t_{Ret.}$ = 1.68 | LCMSBAS1 |
| C.23 | 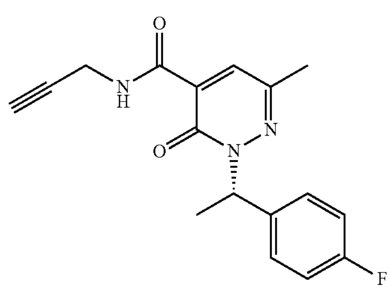 [SMILES: C#CCNC(=O)c1cc(C)nn([C@@H](C)c2ccc(F)cc2)c1=O] | M + H = 314; $t_{Ret.}$ = 1.75 | LCMSBAS1 |
| C.24 | 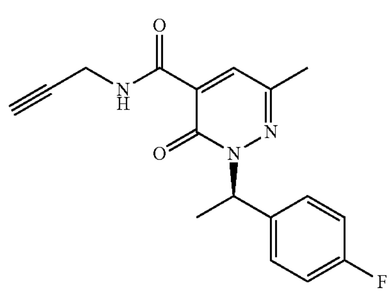 [SMILES: C#CCNC(=O)c1cc(C)nn([C@H](C)c2ccc(F)cc2)c1=O] | M + H = 314; $t_{Ret.}$ = 1.75 | LCMSBAS1 |

-continued

| # | Structure | MS (M + H)+; $t_{Ret.}$ HPLC [min] | HPLC method |
|---|---|---|---|
| C.25 | 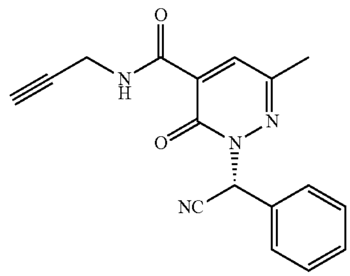 [SMILES: C#CCNC(=O)c1cc(C)nn([C@@H](C#N)c2ccccc2)c1=O] | M + H = 307; $t_{Ret.}$ = 1.62 | LCMSBAS1 |
| C.26 | 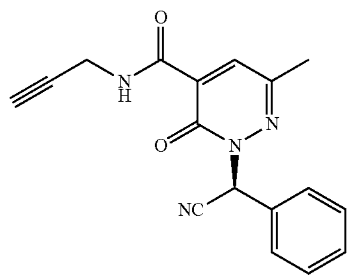 [SMILES: C#CCNC(=O)c1cc(C)nn([C@H](C#N)c2ccccc2)c1=O] | M + H = 307; $t_{Ret.}$ = 1.62 | LCMSBAS1 |
| C.27 | 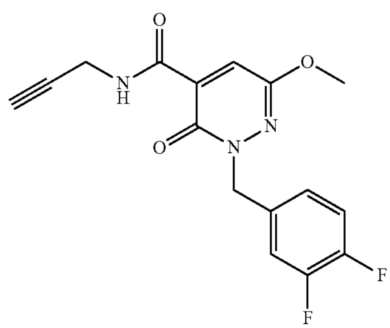 [SMILES: C#CCNC(=O)c1cc(OC)nn(Cc2ccc(F)c(F)c2)c1=O] | M + H = 334; $t_{Ret.}$ = 1.62 | LCMSBAS1 |
| C.28 | 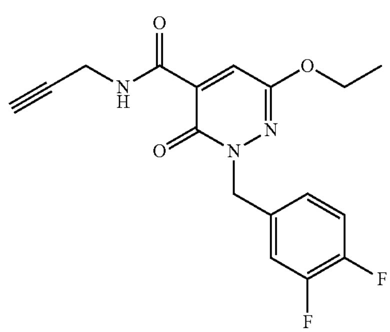 [SMILES: C#CCNC(=O)c1cc(OCC)nn(Cc2ccc(F)c(F)c2)c1=O] | M + H = 348; $t_{Ret.}$ = 1.93 | LCMSBAS1 |
| C.29 | 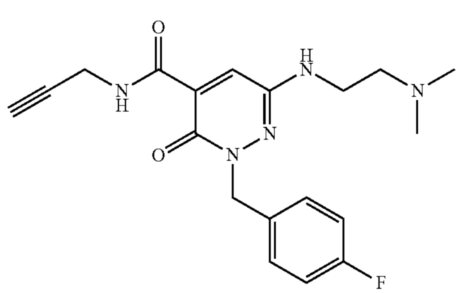 | M + H = 372; $t_{Ret.}$ = 1.80 | LCMSBAS1 |

-continued

| # | Structure | MS (M + H)+; t_Ret. HPLC [min] | HPLC method |
|---|---|---|---|
| C.30 | (structure) | M + H = 334; t_Ret. = 1.88 | LCMSBAS1 |
| C.31 | (structure) | M + H = 390; t_Ret. = 1.86 | 1_FEC |
| C.32 | (structure) | M + H = 338; t_Ret. = 1.15 | 1_FEC |
| C.33 | (structure) | M + H = 284; t_Ret. = 1.75 | FECB6 |
| C.34 | (structure) | M + H = 302; t_Ret. = 1.79 | FECB6 |
| C.35 | (structure) | M + H = 320; t_Ret. = 1.37 | LCMSBAS1 |

-continued
| # | Structure | MS (M + H)⁺; $t_{Ret.}$ HPLC [min] | HPLC method |
|---|---|---|---|
| C.36 | 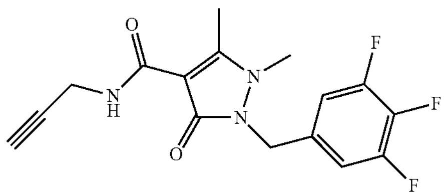 [SMILES: C#CCNC(=O)c1c(C)n(C)n(Cc2cc(F)c(F)c(F)c2)c1=O] | M + H = 338; $t_{Ret.}$ = 1.41 | LCMSBAS1 |
| C.37 | 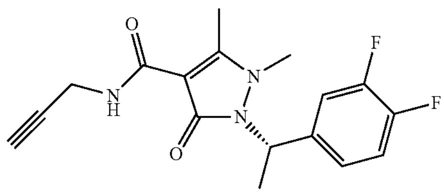 [SMILES: C#CCNC(=O)c1c(C)n(C)n([C@@H](C)c2ccc(F)c(F)c2)c1=O] | M + H = 334; $t_{Ret.}$ = 1.42 | LCMSBAS1 |
| C.38 | 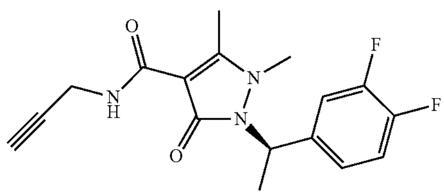 [SMILES: C#CCNC(=O)c1c(C)n(C)n([C@H](C)c2ccc(F)c(F)c2)c1=O] | M + H = 334; $t_{Ret.}$ = 1.42 | LCMSBAS1 |
| C.39 | 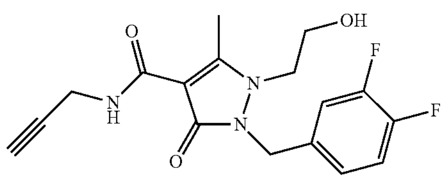 [SMILES: C#CCNC(=O)c1c(C)n(CCO)n(Cc2ccc(F)c(F)c2)c1=O] | M + H = 350; $t_{Ret.}$ = 1.53 | 1_FEC |
| C.40 | 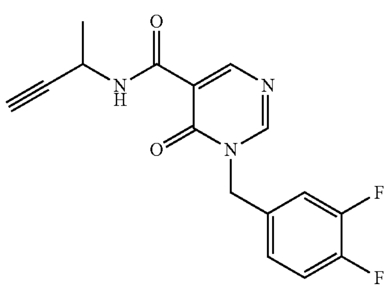 [SMILES: C#CC(C)NC(=O)c1cncn(Cc2ccc(F)c(F)c2)c1=O] | M + H = 318; $t_{Ret.}$ = 0.98 | 1_FEC |
Method for Synthesising C.41
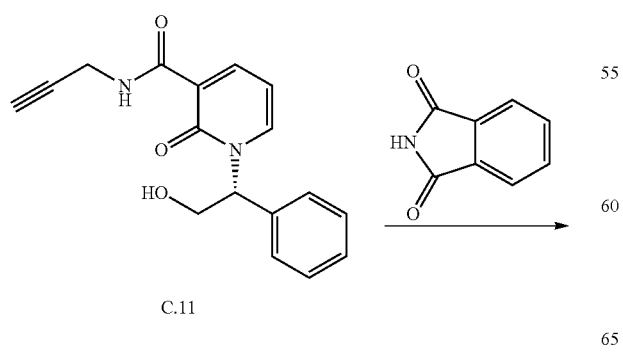
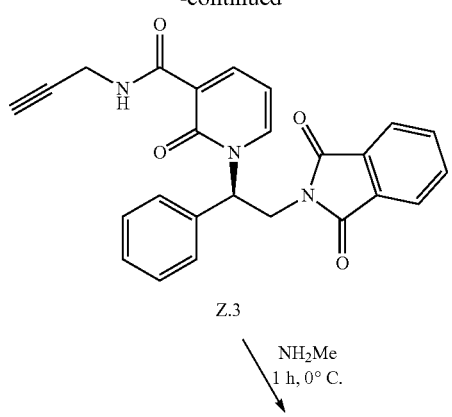
NH₂Me
1 h, 0° C.

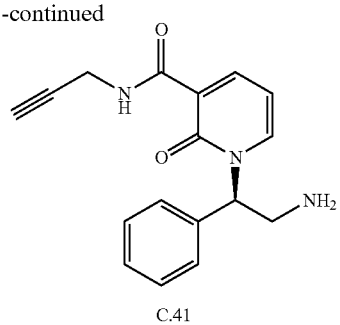

C.41

Propargylamide C.11 (400 mg, 1.4 mmol), phthalimide (260 mg, 1.8 mmol) and triphenylphosphine (498 mg, 1.9 mmol) are placed in THF (5 mL) and cooled to 0° C. Then diisopropylazodicarboxylate (406 mg, 1.9 mmol) in THF (10 mL) is added dropwise over 1 h, the reaction mixture is stirred for 15 h at 20° C., the solvent is eliminated and the intermediate product Z.3 (574 mg, 100%; HPLC-MS: MS (M+H)$^+$=426; $t_{Ret.}$=1.08 min; method 1_FEC) is reacted in the next step without any further working up.

Z.3 (2.15 g, 5.1 mmol) is placed in EtOH (1 mL), combined with methylamine (in EtOH, 33 wt %, 2.4 g, 25.3 mmol) and stirred for 6 h at 70° C. The solvent is removed, the residue is taken up in DCM (30 mL), cooled to 0° C. for 1 h, the resulting residue is filtered off and washed with DCM (10 mL). The filtrate is diluted with DMSO (3 mL), evaporated down, purified by prep. HPLC (ACN/water, HCOOH as modifier) and product C.41 (745 mg, 50%; HPLC-MS: MS (M+H)$^+$=296; $t_{Ret.}$=0.41 min; method 1_FEC) is obtained.

Method for Synthesising C.42

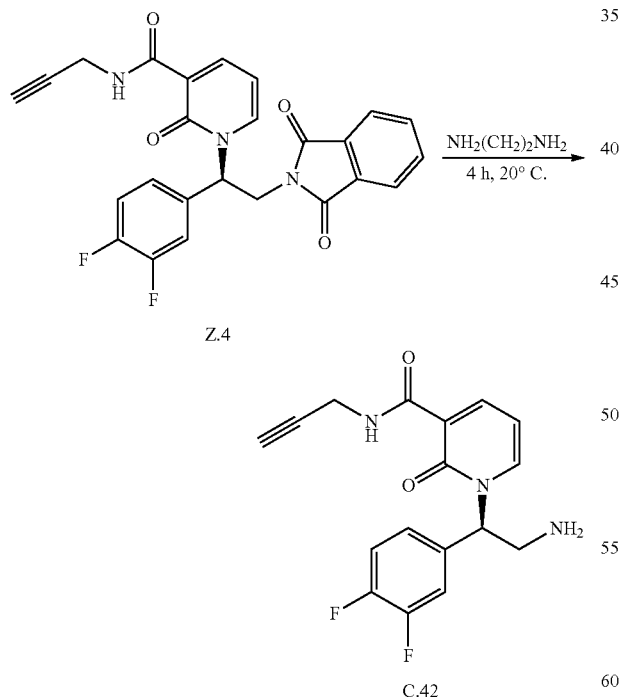

Intermediate compound Z.4 (HPLC-MS: MS (M+H)$^+$=462; $t_{Ret.}$=1.13 min; method 1_FEC) is prepared analogously to Z.3 from C.14 (see above).

Z.4 (1.05 g, 2.23 mmol) is taken up in MeOH (15 mL), combined with ethylenediamine (1 mL) and stirred for 4 h at 20° C. The solvent is removed, the residue is purified by column chromatography (ethyl acetate, then DCM/MeOH=9:1) and product C.42 (565 mg, 76%; HPLC-MS: MS (M+H)$^+$=332; $t_{Ret.}$=1.37 min; method LCMSBAS1) is obtained.

Propargylamides C.41 and C.42 (Table 6)

| # | Structure | MS (M + H)$^+$; $t_{Ret.}$ HPLC [min] | HPLC method |
|---|---|---|---|
| C.41 | 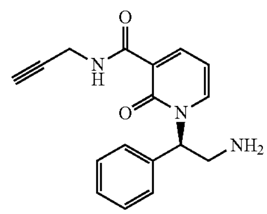 [SMILES: C#CCNC(=O)c1cccn([C@@H](CN)c2ccccc2)c1=O] | M + H = 296; $t_{Ret.}$ = 0.41 | 1_FEC |
| C.42 | | M + H =332; $t_{Ret.}$ = 1.37 | LCMSBAS1 | c) Synthesis of activated imidazo[4,5-c]quinolines G

Reaction scheme C

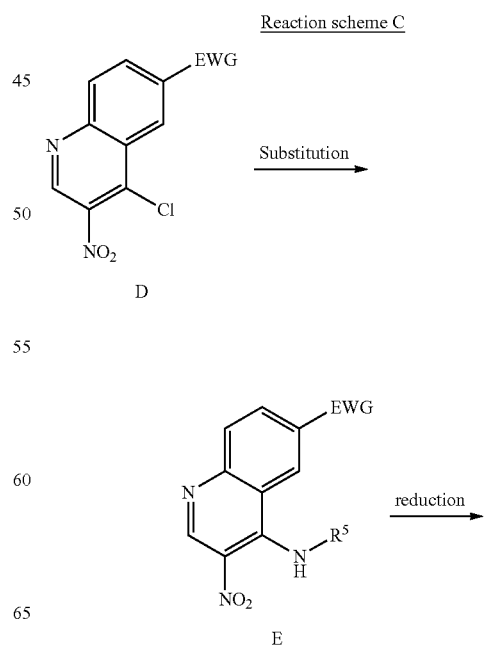

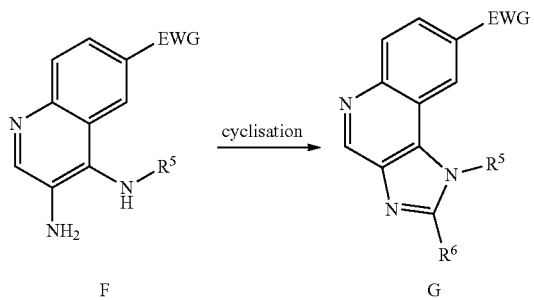

The imidazo[4,5-c]quinoline system is synthesised starting from 4-chloro-3-nitroquinolines D which are activated in the 6-position by a leaving group EWG, for example halogen, triflate or mesylate. Preferably 4-chloro-6-iodo-3-nitro-quinoline (D.1) or 6-bromo-4-chloro-3-nitro-quinoline (D.2) is used.

In a first step the groups $R^5$ are incorporated by nucleophilic substitution via the corresponding amines $R^5$—$NH_2$ and intermediates E are obtained. Then the nitro group is reduced to form diamines F, wherein for example iron, zinc or tin combined with acids, such as for example HCl or acetic acid, are used as reducing agent. Other methods of reducing aromatic nitro compounds are sufficiently well known to the skilled man. In the final step of the synthesis cyclisation is carried out with orthocarbonates, orthocarboxylic acid esters, acid chlorides or aldehydes.

Method for synthesising
4-chloro-6-iodo-3-nitro-quinoline D.1

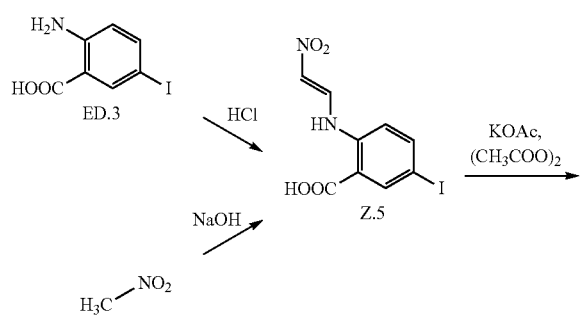

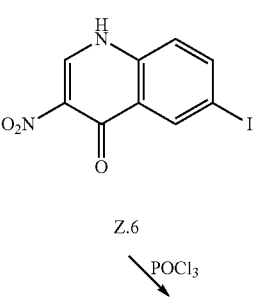

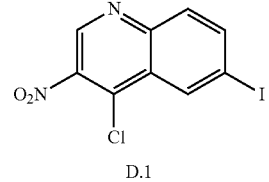

Anthranilic acid ED.3 (5.06 g, 19.2 mmol) is stirred in conc. HCl (7.0 mL) for 12 h at 20° C. In a second round flask, nitromethane (2.56 g, 42.0 mmol) is added dropwise to a mixture of ice (6.0 g, 333 mmol) and NaOH (2.53 g, 63.4 mmol), the mixture is stirred for 1 h at 0° C., then heated to 20° C. over 1 h, then poured onto an ice/HCl mixture (5 g/7 mL) and combined with the aniline-HCl mixture. The reaction mixture is stirred for 12 h at 20° C., the precipitate is filtered off, washed with $H_2O$ and dried.

The precipitate (Z.5) is taken up in acetic anhydride (35 mL), combined with KOAc (2.19 g, 22.3 mmol) and heated to 120° C. for 2 h. The solvent is removed and the residue is washed with glacial acetic acid and $H_2O$ and dried.

The residue (Z.6) is taken up in $POCl_3$ (20 mL, 209 mmol) and heated to 120° C. for 40 min. The reaction mixture is evaporated down to one-third, poured onto ice water, washed with $H_2O$, dried and 4-chloro-6-iodo-3-nitro-quinoline D.1 (4.0 g, 95%) is obtained.

Method for synthesising
6-iodo-3-nitro-quinolin-4-ylamine E.1

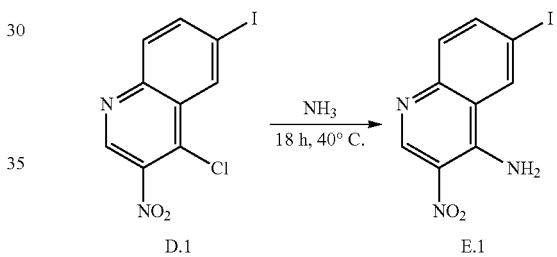

Quinoline D.1 (4.0 g, 12.0 mmol) is placed in DCM (20 mL), cooled to 0° C., combined with ammonia in MeOH (6 mL, 42.0 mmol), the reaction mixture is heated to 20° C. and stirred for 18 h at 40° C. The reaction mixture is evaporated to dryness, suspended in DCM (10 mL), filtered off, the precipitate is washed with water (5 mL), dried in vacuo and product E.1 (3.7 g, 97%; HPLC-MS: MS $(M+H)^+$=316; $t_{Ret.}$=0.695 min; method 1_FEC) is obtained.

Method for synthesising tert-butyl (S)-3-(6-iodo-3-nitro-quinolin-4-ylamino)-piperidine-1-carboxylate—E.24

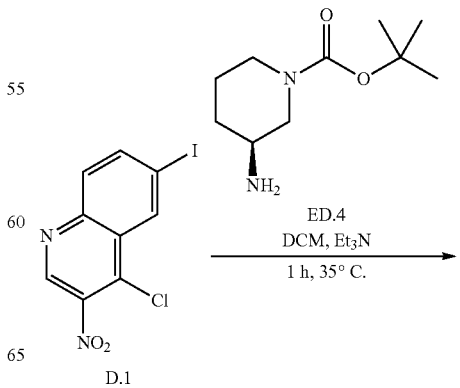

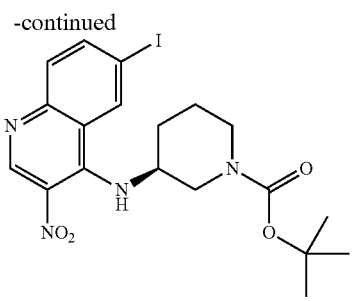

E.24

Quinoline D.1 (1.5 g, 4.5 mmol) and tert-butyl (S)-3-amino-piperidine-1-carboxylate—ED.4 (988 mg, 4.9 mmol) are taken up in DCM (5 mL), combined with $Et_3N$ (620 μL, 4.5 mmol) and stirred for 1 h at 35° C. The solvent is removed, the residue is taken up in MeOH (10 mL), water (10 mL) and sat. $K_2CO_3$ solution (2 mL), the precipitate is filtered off, washed with water (5 mL) and MeOH (5 mL), freeze-dried and product E.24 (2.1 g, 92%; HPLC-MS: MS $(M+H)^+$=499; $t_{Ret.}$=1.212 min; method 1_FEC) is obtained.

The other nitroquinolines E.2-E.30 are prepared analogously to nitroquinoline E.1 or E.24 (Table 7).

| # | Structure | MS (M + H)⁺ | $t_{Ret.}$ HPLC [min] HPLC method |
|---|---|---|---|
| E.1 | 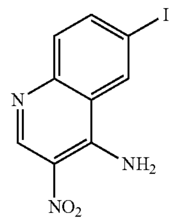 [SMILES: Nc1c([N+](=O)[O-])cnc2ccc(I)cc12] | 316 | 0.695 1_FEC |
| E.2 | 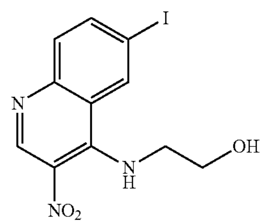 [SMILES: O=[N+]([O-])c1cnc2ccc(I)cc2c1NCCO] | 360 | 0.622 1_FEC |
| E.3 | 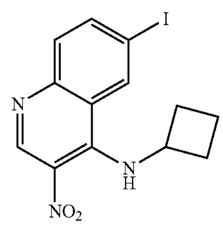 [SMILES: O=[N+]([O-])c1cnc2ccc(I)cc2c1NC1CCC1] | 370 | 1.252 1_FEC |
| E.4 | 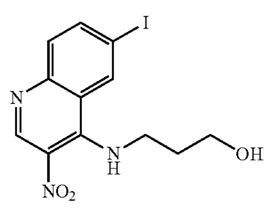 [SMILES: O=[N+]([O-])c1cnc2ccc(I)cc2c1NCCCO] | 374 | 0.649 1_FEC |
| E.5 | 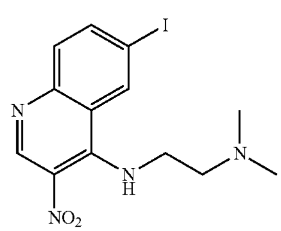 [SMILES: CN(C)CCNc1c([N+](=O)[O-])cnc2ccc(I)cc12] | 387 | 0.399 1_FEC |

| # | Structure | MS (M + H)+ | t_Ret. HPLC [min] HPLC method |
|---|---|---|---|
| E.6 | 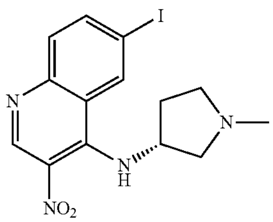 [SMILES: CN1CC[C@@H](Nc2c([N+](=O)[O-])cnc3ccc(I)cc23)C1] | 399 | 0.494<br>1_FEC |
| E.7 | 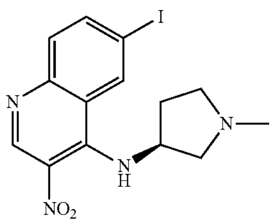 [SMILES: CN1CC[C@H](Nc2c([N+](=O)[O-])cnc3ccc(I)cc23)C1] | 399 | 0.474<br>1_FEC |
| E.8 | 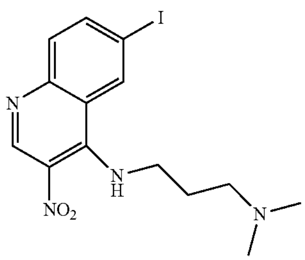 [SMILES: CN(C)CCCNc1c([N+](=O)[O-])cnc2ccc(I)cc12] | 401 | 0.431<br>1_FEC |
| E.9 | 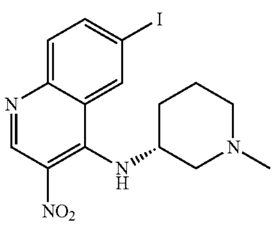 [SMILES: CN1CCC[C@@H](Nc2c([N+](=O)[O-])cnc3ccc(I)cc23)C1] | 413 | 1.062<br>1_BAS_MeOH_POS |
| E.10 | 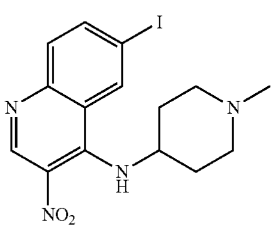 [SMILES: CN1CCC(Nc2c([N+](=O)[O-])cnc3ccc(I)cc23)CC1] | 413 | 0.465<br>1_FEC |
| E.11 | 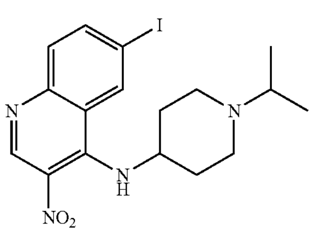 [SMILES: CC(C)N1CCC(Nc2c([N+](=O)[O-])cnc3ccc(I)cc23)CC1] | 441 | 0.592<br>1_FEC |

-continued
| # | Structure | MS (M + H)+ | t_Ret. HPLC [min] HPLC method |
|---|---|---|---|
| E.12 | 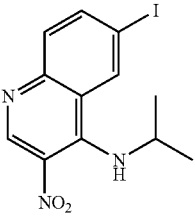 | 358 | 1.171 1_FEC |
| E.13 | 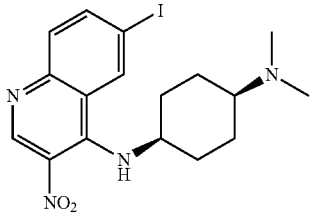 | 441 | 0.695 1_FEC |
| E.14 | 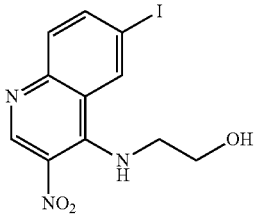 [SMILES: O=[N+]([O-])c1cnc2ccc(I)cc2c1NCCO] | 360 | 0.617 1_FEC |
| E.15 | 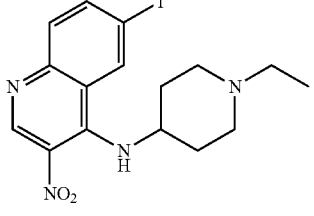 | 427 | 0.793 1_BAS |
| E.16 | 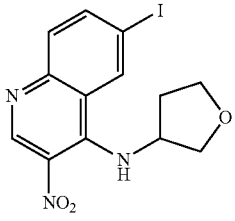 [SMILES: O=[N+]([O-])c1cnc2ccc(I)cc2c1NC1CCOC1] | 386 | 0.989 1_FEC |
| E.17 | 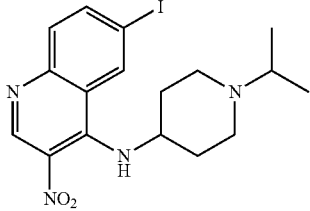 | 441 | 0.695 1_FEC |

-continued

| # | Structure | MS (M + H)+ | t_Ret. HPLC [min] HPLC method |
|---|---|---|---|
| E.18 | 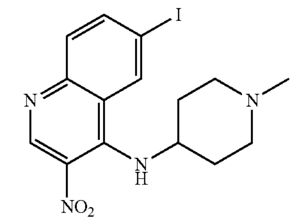 [SMILES: CN1CCC(Nc2c([N+](=O)[O-])cnc3ccc(I)cc23)CC1] | 413 | 0.466<br>1_FEC |
| E.19 | 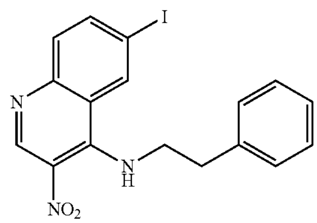 [SMILES: O=[N+]([O-])c1cnc2ccc(I)cc2c1NCCc1ccccc1] | 420 | 1.319<br>1_FEC |
| E.20 | 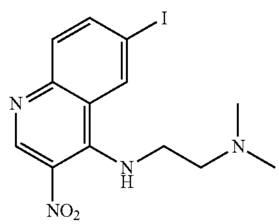 [SMILES: CN(C)CCNc1c([N+](=O)[O-])cnc2ccc(I)cc12] | 387 | 0.442<br>1_FEC |
| E.21 | 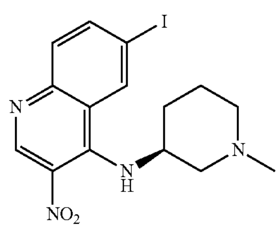 [SMILES: CN1CCC[C@H](Nc2c([N+](=O)[O-])cnc3ccc(I)cc23)C1] | 413 | 1.037<br>1_BAS_MeOH_POS |
| E.22 | 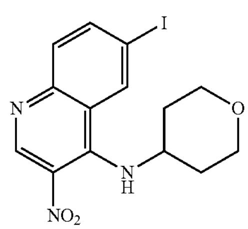 [SMILES: O=[N+]([O-])c1cnc2ccc(I)cc2c1NC1CCOCC1] | 400 | 1.043<br>1_FEC |
| E.23 | 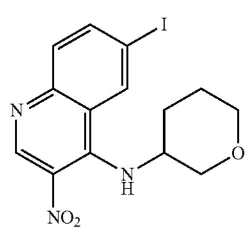 [SMILES: O=[N+]([O-])c1cnc2ccc(I)cc2c1NC1CCCOC1] | 400 | 1.119<br>1_FEC |

-continued
| # | Structure | MS (M + H)+ | t_Ret. HPLC [min] HPLC method |
|---|---|---|---|
| E.24 | 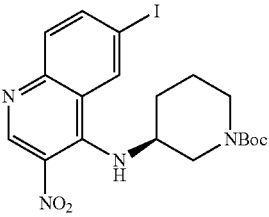 [SMILES: CC(C)(C)OC(=O)N1CCC[C@H](Nc2c([N+](=O)[O-])cnc3ccc(I)cc23)C1] | 499 | 1.212 1_FEC |
| E.25 | 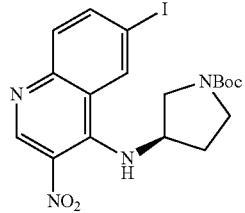 [SMILES: CC(C)(C)OC(=O)N1CC[C@@H](Nc2c([N+](=O)[O-])cnc3ccc(I)cc23)C1] | 485 | 1.328 1_FEC |
| E.26 | 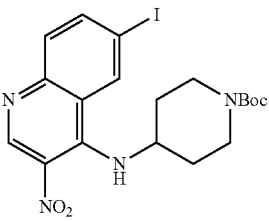 [SMILES: CC(C)(C)OC(=O)N1CCC(Nc2c([N+](=O)[O-])cnc3ccc(I)cc23)CC1] | 379 | 0.307 1_FEC |
| E.27 | 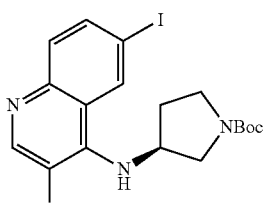 | 485 | 1.301 1_FEC |
| E.28 | 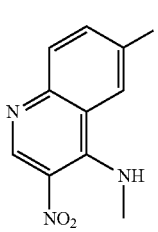 | 330 | 0.737 1_FEC |
| E.29 | 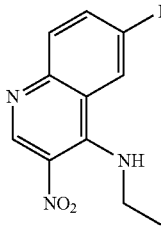 | 344 | 0.891 1_FEC |

-continued

| # | Structure | MS (M + H)+ | $t_{Ret.}$ HPLC [min] HPLC method |
|---|---|---|---|
| E.30 | 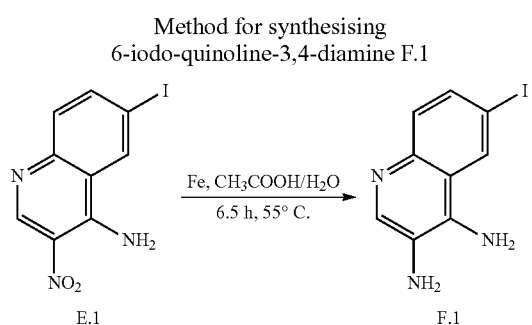 | 441 | 0.695 1_FEC |

Method for synthesising 6-iodo-quinoline-3,4-diamine F.1

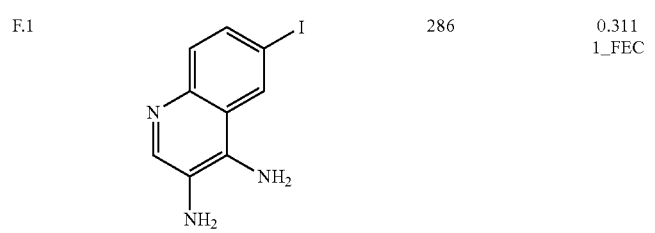

Nitroquinoline E.1 (3.7 g, 11.7 mmol) and iron (3.4 g, 60.1 mmol) are taken up in a mixture of glacial acetic acid (3 mL) and water (15 mL) and stirred for 6.5 h at 55° C. The reaction mixture is made alkaline (pH<12), the precipitate is filtered through Celite, the whole filter cake is suspended in DCM/MeOH 1:1 (600 mL) and filtered off, the organic phase is dried on $MgSO_4$, filtered and evaporated down. The solid is suspended in water (20 mL), filtered off and product F.1 (3.24 g, 97%; HPLC-MS: MS (M+H)+=286; $t_{Ret.}$=0.311 min; method 1_FEC) is obtained.

Diaminoquinolines F.2-F.30 are prepared analogously to compound F.1 (Table 8).

| # | Structure | MS (M + H)+ | $t_{Ret.}$ HPLC [min] HPLC method |
|---|---|---|---|
| F.1 | 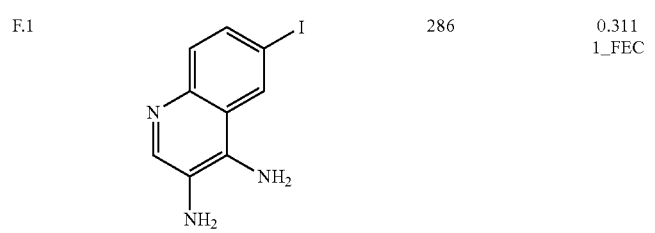 | 286 | 0.311 1_FEC |
| F.2 | 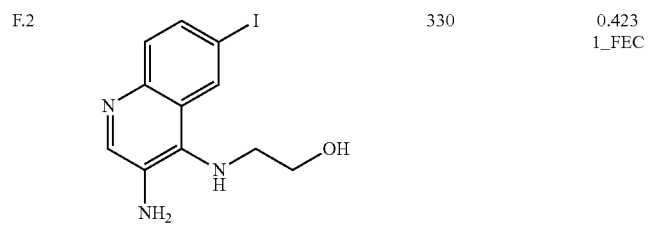 | 330 | 0.423 1_FEC |
| F.3 | 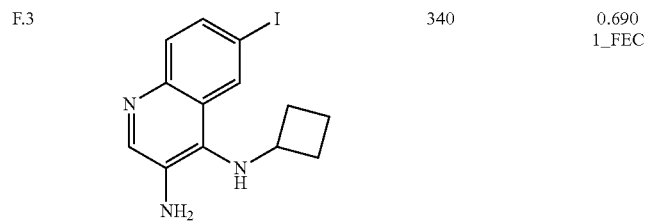 | 340 | 0.690 1_FEC |

-continued

| # | Structure | MS (M + H)⁺ | $t_{Ret.}$ HPLC [min] HPLC method |
|---|---|---|---|
| F.4 | 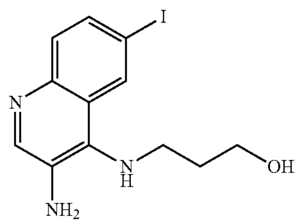 [SMILES: Nc1cnc2ccc(I)cc2c1NCCCO] | 344 | 0.349<br>1_FEC |
| F.5 | 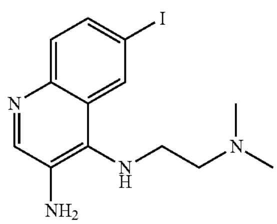 | 357 | 0.126<br>1_FEC |
| F.6 | 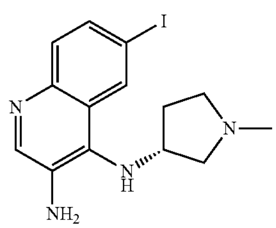 | 369 | 0.129<br>1_FEC |
| F.7 | 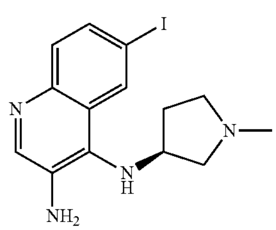 | 369 | 0.897<br>1_BAS_MeOH_POS |
| F.8 | 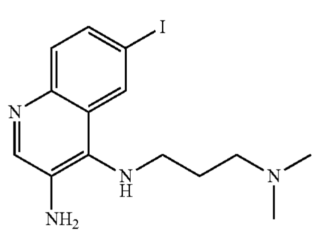 [SMILES: CN(C)CCCNc1c(N)cnc2ccc(I)cc12] | 371 | 0.127<br>1_FEC |
| F.9 | 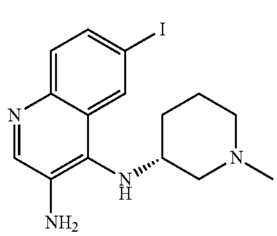 | 383 | 0.982<br>1_BAS_MeOH_POS |

-continued

| # | Structure | MS (M + H)+ | t_Ret. HPLC [min] HPLC method |
|---|---|---|---|
| F.10 | 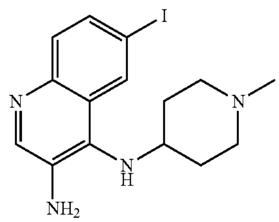 | 383 | 0.126<br>1_FEC |
| F.11 | 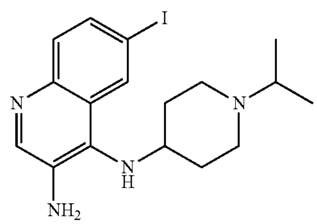 | 411 | 0.968<br>1_BAS_MeOH_POS |
| F.12 | 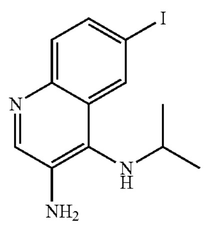 [SMILES: CC(C)Nc1c(N)cnc2ccc(I)cc12] | 328 | 0.970<br>1_BAS_MeOH_POS |
| F.13 | 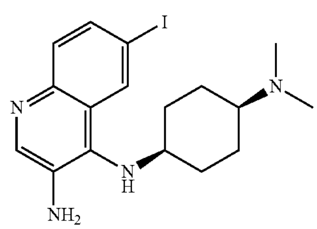 [SMILES: CN(C)[C@H]1CC[C@@H](Nc2c(N)cnc3ccc(I)cc23)CC1] | 411 | 0.626<br>1_BAS |
| F.14 | 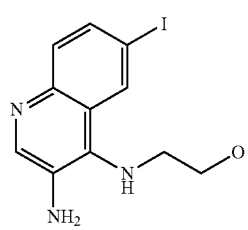 [SMILES: Nc1cnc2ccc(I)cc2c1NCCO] | 330 | 0.337<br>1_FEC |
| F.15 | 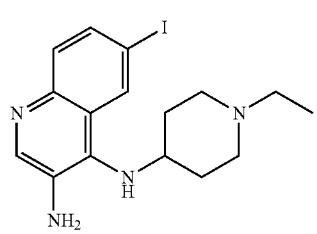 [SMILES: CCN1CCC(Nc2c(N)cnc3ccc(I)cc23)CC1] | 397 | 0.618<br>1_BAS |

-continued
| # | Structure | MS (M + H)+ | $t_{Ret.}$ HPLC [min] HPLC method |
|---|---|---|---|
| F.16 | 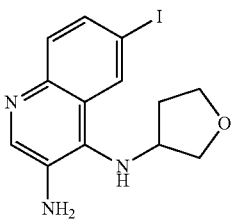 | 356 | 0.583<br>1_BAS |
| F.17 | 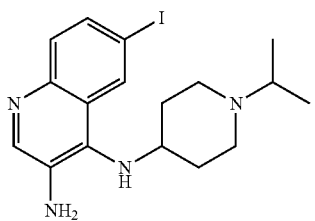 | 411 | 0.626<br>1_BAS |
| F.18 | 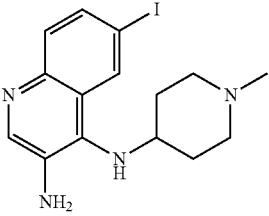 | 383 | 0.125<br>1_FEC |
| F.19 | 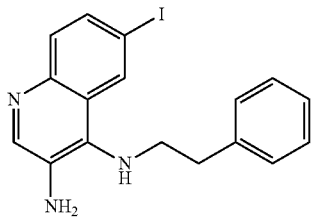 | 390 | 0.901<br>1_FEC |
| F.20 | 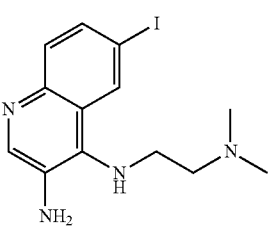 | 357 | 0.127<br>1_FEC |
| F.21 | 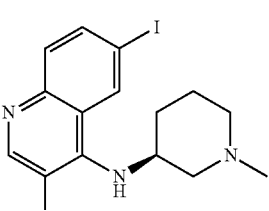 | 383 | 0.939<br>1_BAS_MeOH_POS |

-continued
| # | Structure | MS (M + H)⁺ | t_Ret. HPLC [min] HPLC method |
|---|---|---|---|
| F.22 | 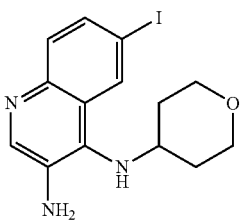 [SMILES: Nc1cnc2ccc(I)cc2c1NC1CCOCC1] | 370 | 0.606 1_BAS |
| F.23 | 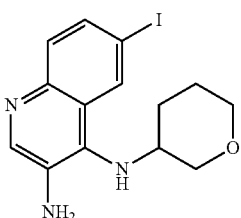 | 370 | 0.656 1_BAS |
| F.24 | 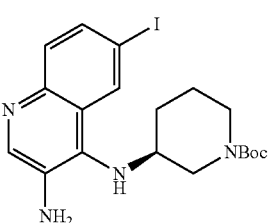 | 469 | 0.896 1_FEC |
| F.25 | 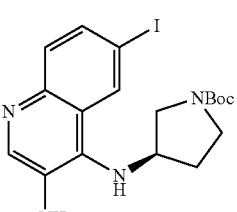 | 455 | 0.198 1_FEC |
| F.26 | 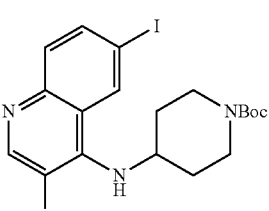 | 479 | 1.430 1_FEC |
| F.27 | 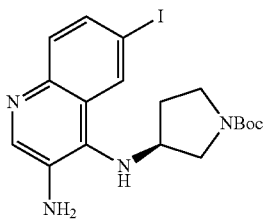 | 455 | 0.800 1_FEC |

| # | Structure | MS (M + H)+ | $t_{Ret.}$ HPLC [min] HPLC method |
|---|---|---|---|
| F.28 | 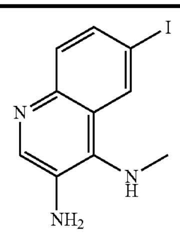 | 330 | 0.701<br>1_FEC |
| F.29 | 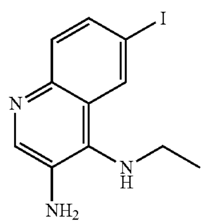 | 344 | 0.958<br>1_FEC |
| F.30 | 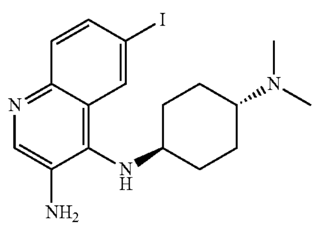 | 411 | 0.626<br>1_BAS |

Method for synthesising
8-iodo-1H-imidazo[4,5-c]quinoline G.1

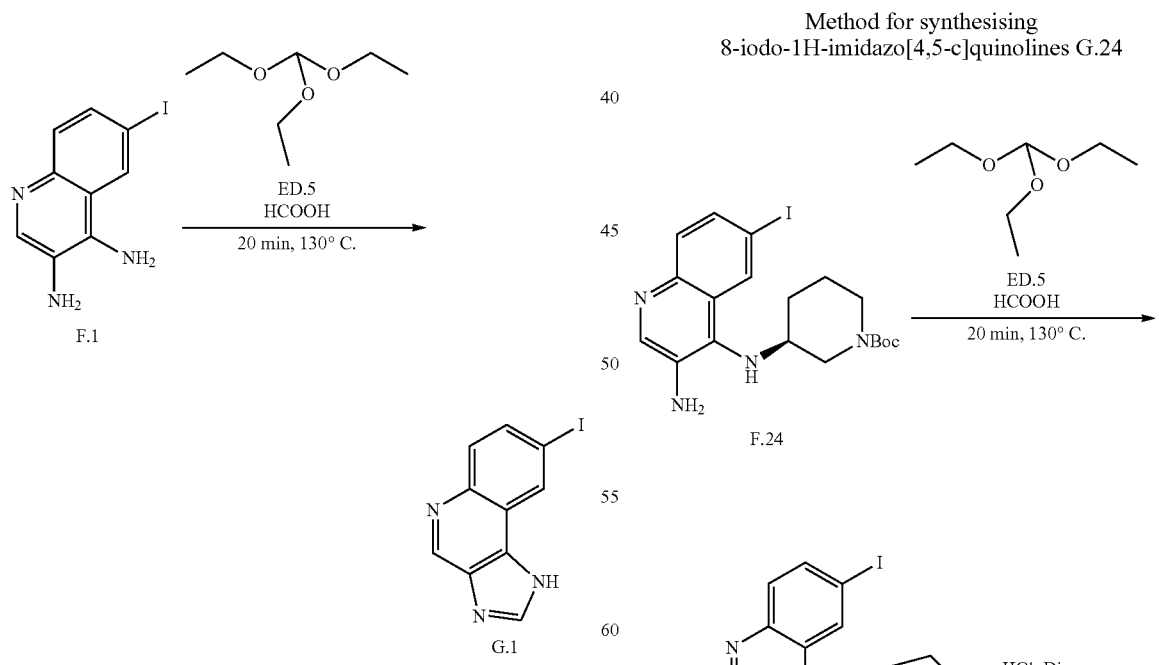

Diaminoquinoline F.1 (800 mg, 2.8 mmol) is taken up in formic acid (500 mg), combined with triethylorthoformate ED.5 (3.0 g, 20.2 mmol) and stirred for 20 min at 130° C. The reaction mixture is evaporated to dryness, the residue is taken up in ammonia (10 mL, 4 M in MeOH), evaporated to dryness again and product G.1 (610 mg, 74%; HPLC-MS: MS (M+H)+=296; $t_{Ret.}$=0.444 min; method 1_FEC) is obtained.

Method for synthesising
8-iodo-1H-imidazo[4,5-c]quinolines G.24

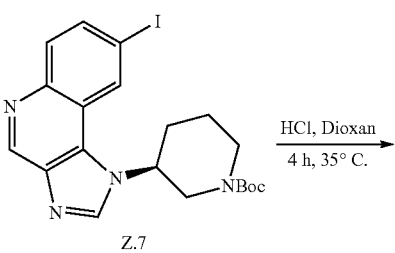

-continued

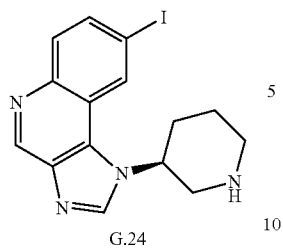
G.24

Diaminoquinoline F.24 (1.0 g, 2.1 mmol) is taken up in formic acid (200 mg), mixed with triethylorthoformate ED.5 (2.0 g, 13.5 mmol) and stirred for 20 min at 130° C. The reaction mixture is evaporated to dryness, the residue is taken up in CH$_3$CN (10 mL), combined with ammonia (2 mL, 30%), freeze-dried and intermediate product Z.7 (1.0 g, 98%) is obtained.

Intermediate product Z.7 (1.0 g, 2.1 mmol) is taken up in dioxane (5 mL), combined with HCl (4.2 mL, 16.8 mmol, 4 M in dioxane) and stirred for 4 h at 35° C. The solvent is eliminated and product G.24 (1.0 g, 100%; HPLC-MS: MS (M+H)$^+$=379; $t_{Ret.}$=0.345 min; method 1_FEC) is obtained.

The other imidazo[4,5-c]quinolines G.2-G.29 are prepared analogously to compound G.1 or G.24 (Table 9).

| # | Structure | MS (M + H)$^+$ | $t_{Ret.}$ HPLC [min] HPLC method |
|---|---|---|---|
| G.1 | | 296 | 0.444 1_FEC |
| G.2 | | 340 | 0.428 1_FEC |
| G.3 | | 350 | 1.167 1_FEC |
| G.4 | 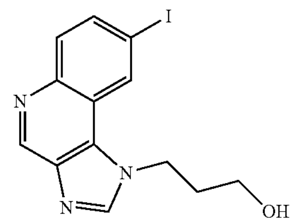 [SMILES: OCCCn1cnc2cnc3ccc(I)cc3c21] | 354 | 0.483 1_FEC |
| G.5 | 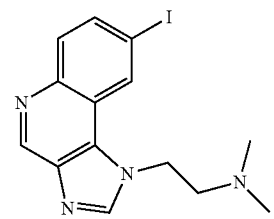 [SMILES: CN(C)CCn1cnc2cnc3ccc(I)cc3c21] | 367 | 0.304 1_FEC |
| G.6 | 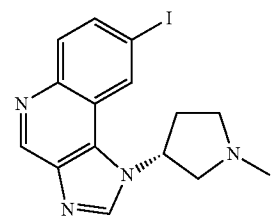 [SMILES: CN1CC[C@@H](n2cnc3cnc4ccc(I)cc4c32)C1] | 379 | 0.273 1_FEC |
| G.7 | 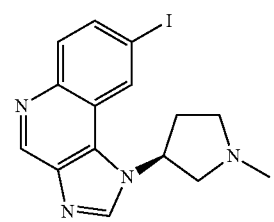 [SMILES: CN1CC[C@H](n2cnc3cnc4ccc(I)cc4c32)C1] | 379 | 0.138 1_FEC |
| G.8 | 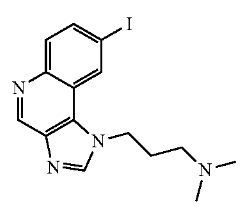 [SMILES: CN(C)CCCn1cnc2cnc3ccc(I)cc3c21] | 381 | 0.136 1_FEC |
| G.9 | 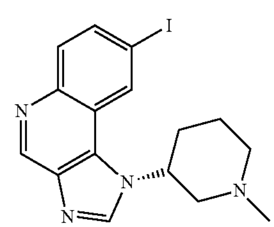 | 393 | 0.901 1_BAS_MeOH_POS |
| G.10 | 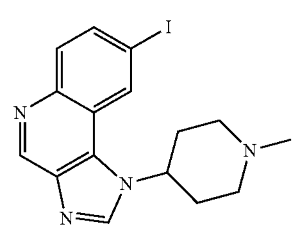 [SMILES: CN1CCC(n2cnc3cnc4ccc(I)cc4c32)CC1] | 393 | 0.317 1_FEC |

-continued

| # | Structure | MS (M+H)+ | t_Ret. HPLC [min] HPLC method |
|---|---|---|---|
| G.11 | 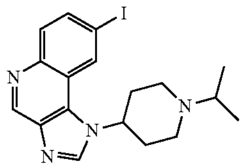 [SMILES: CC(C)N1CCC(n2cnc3cnc4ccc(I)cc4c32)CC1] | 421 | 1.009 1_BAS_MeOH_POS |
| G.12 | 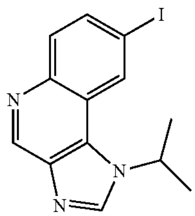 [SMILES: CC(C)n1cnc2cnc3ccc(I)cc3c21] | 338 | 0.886 1_BAS_MeOH_POS |
| G.13 | 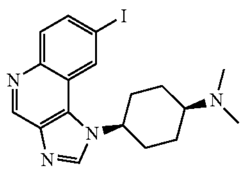 [SMILES: CN(C)[C@H]1CC[C@@H](n2cnc3cnc4ccc(I)cc4c32)CC1] | 421 | 0.426 1_FEC |
| G.14 | 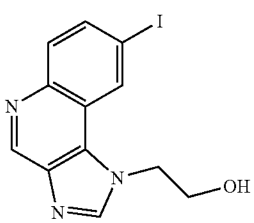 [SMILES: OCCn1cnc2cnc3ccc(I)cc3c21] | 340 | 0.688 1_FEC |
| G.15 | 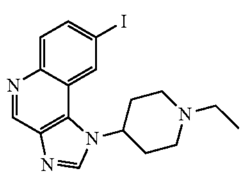 [SMILES: CCN1CCC(n2cnc3cnc4ccc(I)cc4c32)CC1] | 407 | 0.658 1_BAS |
| G.16 | 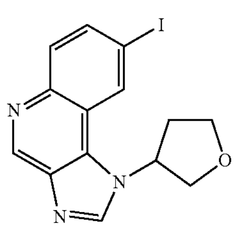 [SMILES: Ic1ccc2ncc3ncn(C4CCOC4)c3c2c1] | 366 | 0.822 1_FEC |

-continued

| # | Structure | MS (M+H)+ | t_Ret. HPLC [min] HPLC method |
|---|---|---|---|
| G.17 | 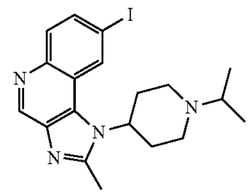 [SMILES: Cc1nc2cnc3ccc(I)cc3c2n1C1CCN(C(C)C)CC1] | 435 | 1.008 1_BAS_MeOH_POS |
| G.18 | 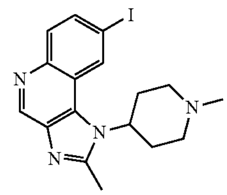 [SMILES: Cc1nc2cnc3ccc(I)cc3c2n1C1CCN(C)CC1] | 407 | 0.357 1_FEC |
| G.19 | 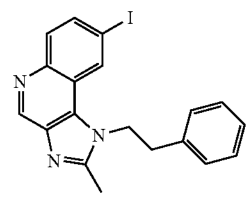 [SMILES: Cc1nc2cnc3ccc(I)cc3c2n1CCc1ccccc1] | 414 | 1.281 1_FEC |
| G.20 | 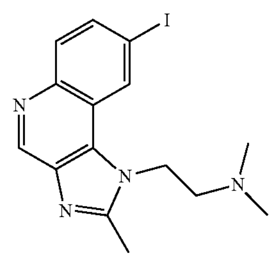 [SMILES: Cc1nc2cnc3ccc(I)cc3c2n1CCN(C)C] | 381 | 0.238 1_FEC |
| G.21 | 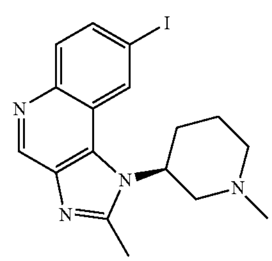 [SMILES: Cc1nc2cnc3ccc(I)cc3c2n1[C@H]1CCCN(C)C1] | 407 | 0.964 1_BAS_MeOH_POS |
| G.22 | 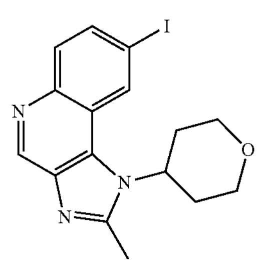 [SMILES: Cc1nc2cnc3ccc(I)cc3c2n1C1CCOCC1] | 394 | 0.976 1_FEC |

-continued
| # | Structure | MS (M+H)+ | t_Ret. HPLC [min] HPLC method |
|---|---|---|---|
| G.23 | 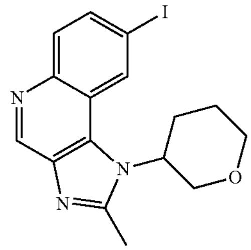 [SMILES: Cc1nc2cnc3ccc(I)cc3c2n1C1CCCOC1] | 394 | 1.095 1_FEC |
| G.24 | 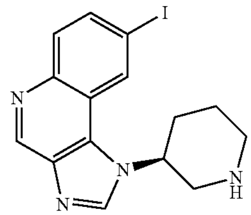 [SMILES: Ic1ccc2ncc3ncn([C@H]4CCCNC4)c3c2c1] | 379 | 0.345 1_FEC |
| G.25 | 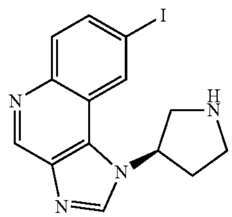 [SMILES: Ic1ccc2ncc3ncn([C@@H]4CCNC4)c3c2c1] | 365 | 0.317 1_FEC |
| G.26 | 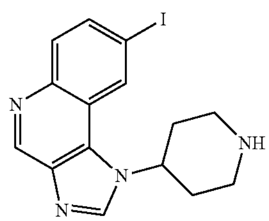 [SMILES: Ic1ccc2ncc3ncn(C4CCNCC4)c3c2c1] | 499 | 1.425 1_FEC |
-continued
| # | Structure | MS (M+H)+ | t_Ret. HPLC [min] HPLC method |
|---|---|---|---|
| G.27 | 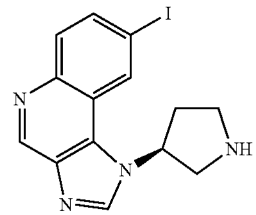 [SMILES: Ic1ccc2ncc3ncn([C@H]4CCNC4)c3c2c1] | 365 | 0.280 1_FEC |
| G.28 | 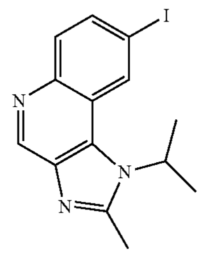 [SMILES: Cc1nc2cnc3ccc(I)cc3c2n1C(C)C] | 352 | 1.78 LCMSBAS1 |
| G.29 | 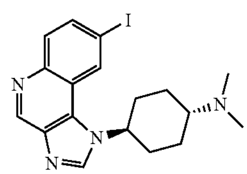 [SMILES: CN(C)[C@H]1CC[C@H](n2cnc3cnc4ccc(I)cc4c32)CC1] | 421 | 0.426 1_FEC |
d) Synthesis of compounds according to the invention (1) via activated imidazo[4,5-c]quinolines G
Reaction scheme D
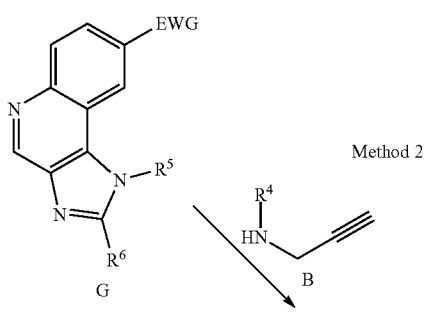
Method 2

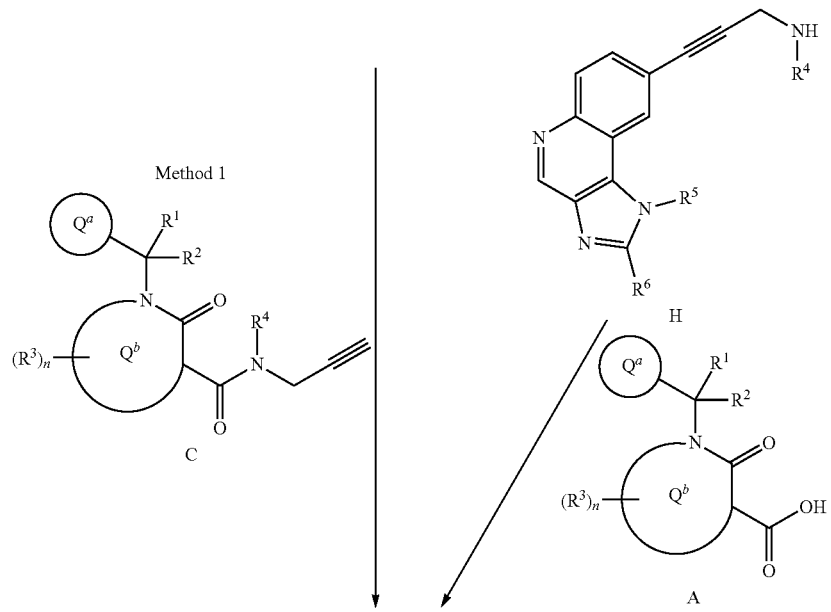

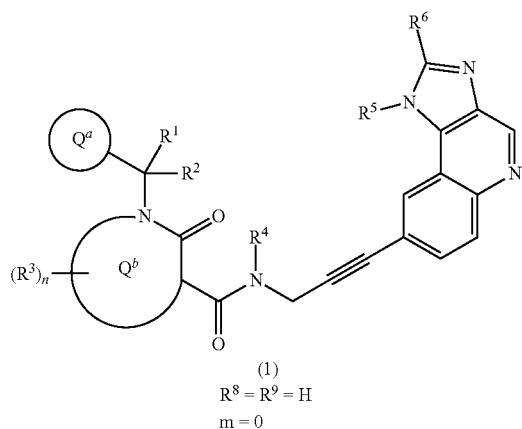

(1)
R⁸ = R⁹ = H
m = 0

Starting from activated imidazo[4,5-c]quinolines G, compounds (1) according to the invention may be obtained by two synthesis routes. According to method 1 imidazo[4,5-c]quinolines G are reacted directly with propargylamides C in a SONOGASHIRA reaction. Alternatively the reaction may be carried out in two steps according to method 2, first of all reacting with a propargylamine B to form compounds H, followed by amide coupling with heterocyclic carboxylic acids A. In the amide coupling, suitable activating reagents such as HATU, TBTU, CDI, DCC, DIC, EDC or the like may be used.

Synthesis of Compounds (1) According to the Invention Using Method 1:

Method for synthesising 1-(3,4-difluoro-benzyl)-6-oxo-1,6-dihydro-pyrimidine-5-carboxylic acid [3-(1H-imidazo[4,5-c]quinolin-8-yl)-prop-2-ynyl]-amide (I-1)

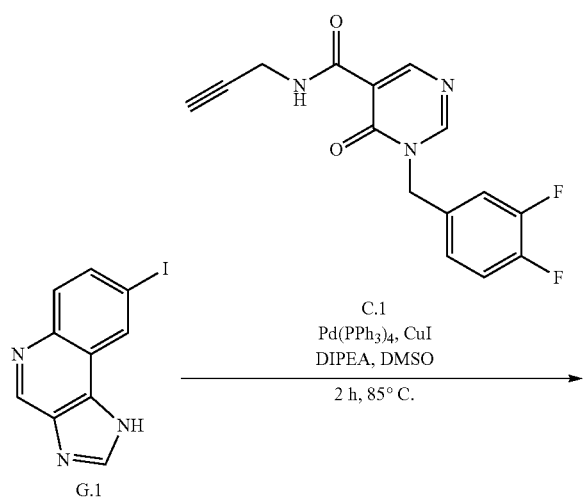

C.1
Pd(PPh₃)₄, CuI
DIPEA, DMSO
2 h, 85° C.

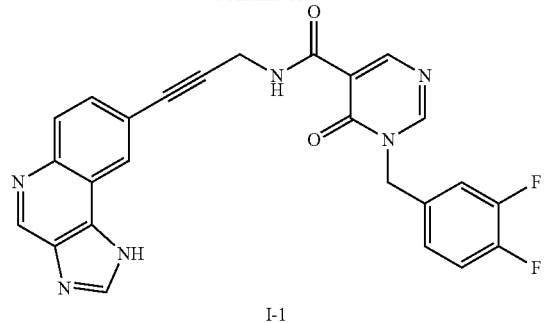

I-1

8-iodo-1H-imidazo[4,5-c]quinoline G.1 (70.0 mg, 0.20 mmol), propargylamide C.1 (63.4 mg, 0.20 mmol), tetrakis(triphenylphosphine)palladium(0) (2.2 mg, 2.0 µmol, 10 mol %), copper(I)iodide (1.0 mg, 10 µmol, 5 mol %) and DIPEA (123 mg, 1.0 mmol) are taken up in DMSO (700 µL) and stirred for 2 h at 85° C. under argon. The reaction mixture is purified by prep. HPLC-MS (acetonitrile/water, HCOOH as modifier) and I-1 (54 mg, 60%; HPLC-MS: MS (M+H)⁺=471; $t_{Ret.}$=1.34 min; method LCMSBAS1) is obtained.

The example compounds I-2-I-15, II-1-II-35 and III-1-III-34 according to the invention are prepared analogously to example compound I-1 (Table 10).

| # | Structure | MS (M + H)⁺ | $t_{Ret.}$ HPLC [min] HPLC method |
|---|---|---|---|
| I-1 | 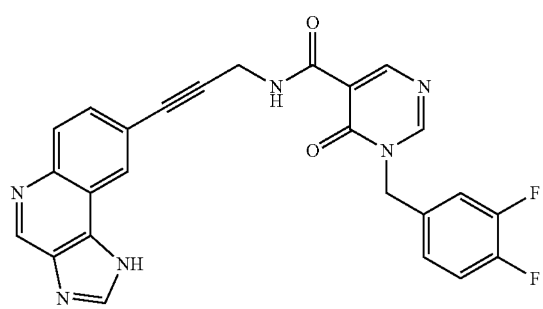 [SMILES: O=C(NCC#Cc1ccc2ncc3nc[nH]c3c2c1)c1cncn(Cc2ccc(F)c(F)c2)c1=O] | 471 | 1.34 LCMSBAS1 |
| I-2 | 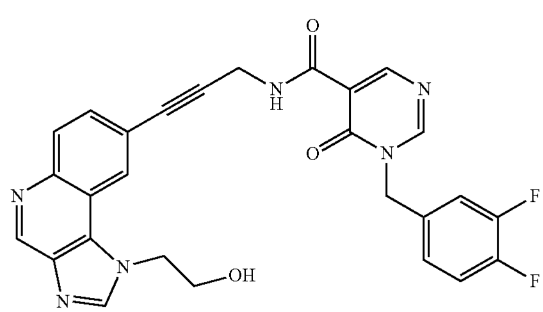 [SMILES: O=C(NCC#Cc1ccc2ncc3ncn(CCO)c3c2c1)c1cncn(Cc2ccc(F)c(F)c2)c1=O] | 515 | 1.48 LCMSBAS1 |

-continued
| # | Structure | MS (M + H)+ | t_Ret. HPLC [min] HPLC method |
|---|---|---|---|
| I-3 | 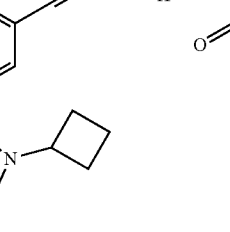 | 525 | 1.75 LCMSBAS1 |
| I-4 | 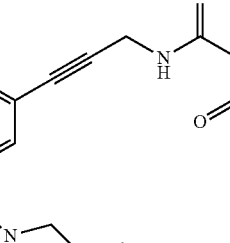 | 529 | 1.50 LCMSBAS1 |
| I-5 | 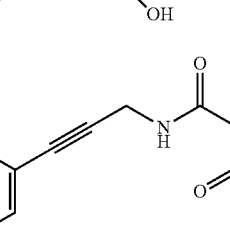 | 542 | 1.62 LCMSBAS1 |
| I-6 | 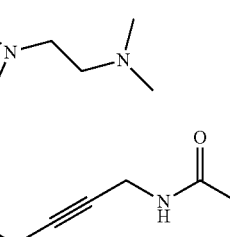 | 554 | 1.66 LCMSBAS1 |
| I-7 | 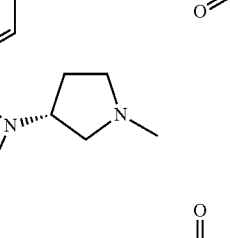 | 554 | 1.66 LCMSBAS1 |

-continued
| # | Structure | MS (M + H)⁺ | t_Ret. HPLC [min] HPLC method |
|---|---|---|---|
| I-8 | 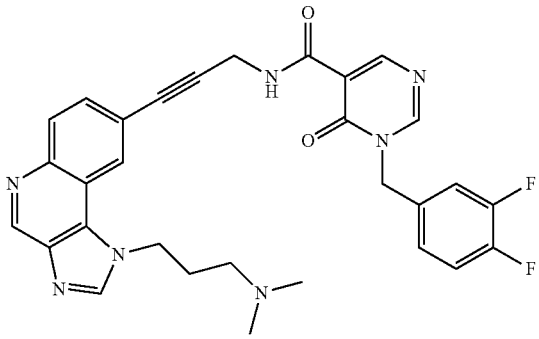 [SMILES: CN(C)CCCn1cnc2cnc3ccc(C#CCNC(=O)c4cncn(Cc5ccc(F)c(F)c5)c4=O)cc3c21] | 556 | 1.66 LCMSBAS1 |
| I-9 | 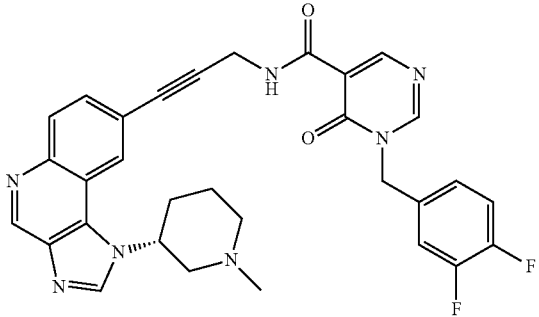 [SMILES: CN1CCC[C@@H](n2cnc3cnc4ccc(C#CCNC(=O)c5cncn(Cc6ccc(F)c(F)c6)c5=O)cc4c32)C1] | 568 | 1.71 LCMSBAS1 |
| I-10 | 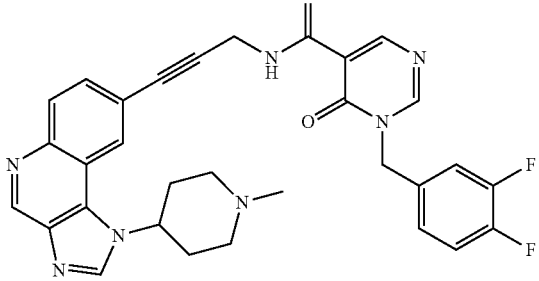 | 568 | 1.62 LCMSBAS1 |
| I-11 | 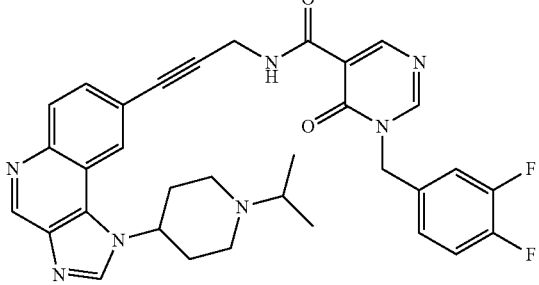 | 596 | 1.76 LCMSBAS1 |
| I-12 | 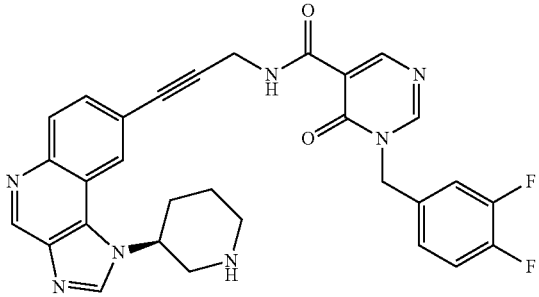 [SMILES: O=C(NCC#Cc1ccc2ncc3ncn([C@H]4CCCNC4)c3c2c1)c1cncn(Cc2ccc(F)c(F)c2)c1=O] | 554 | 1.58 LCMSBAS1 |

| # | Structure | MS (M + H)+ | t_Ret. HPLC [min] HPLC method |
|---|---|---|---|
| I-13 | 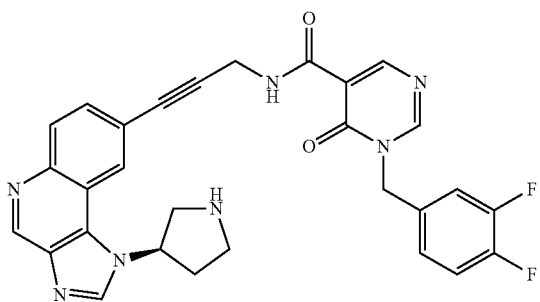 [SMILES: O=C(NCC#Cc1ccc2ncc3ncn([C@@H]4CCNC4)c3c2c1)c1cncn(Cc2ccc(F)c(F)c2)c1=O] | 540 | 1.55 LCMSBAS1 |
| I-14 | 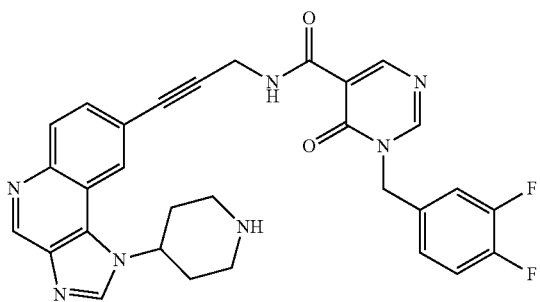 [SMILES: O=C(NCC#Cc1ccc2ncc3ncn(C4CCNCC4)c3c2c1)c1cncn(Cc2ccc(F)c(F)c2)c1=O] | 554 | 1.54 LCMSBAS1 |
| I-15 | 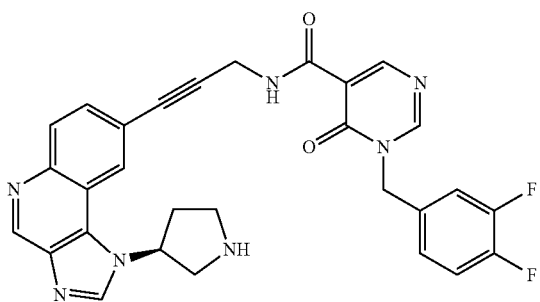 [SMILES: O=C(NCC#Cc1ccc2ncc3ncn([C@H]4CCNC4)c3c2c1)c1cncn(Cc2ccc(F)c(F)c2)c1=O] | 540 | 1.32 LCMSBAS1 |
| II-1 | 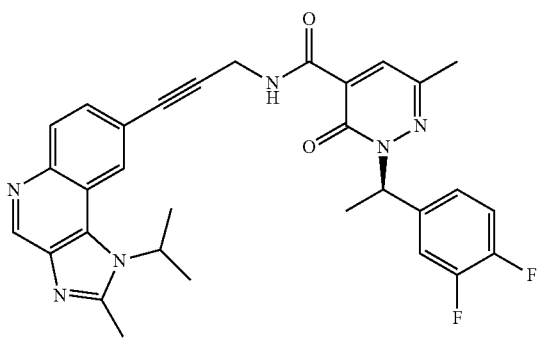 [SMILES: Cc1cc(C(=O)NCC#Cc2ccc3ncc4nc(C)n(C(C)C)c4c3c2)c(=O)n([C@H](C)c2ccc(F)c(F)c2)n1] | 555 | 2.07 LCMSBAS1 |

| # | Structure | MS (M + H)+ | $t_{Ret.}$ HPLC [min] HPLC method |
|---|---|---|---|
| II-2 | 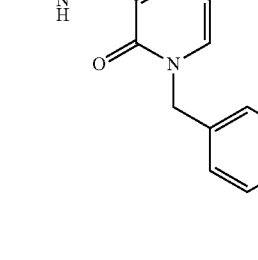 | 490 | 1.76 LCMSBAS1 |
| II-3 | 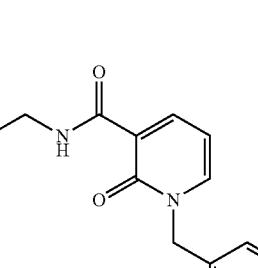 | 526 | 1.80 LCMSBAS1 |
| II-4 | 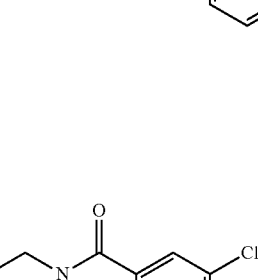 | 561 | 2.04 LCMSBAS1 |
| II-5 | 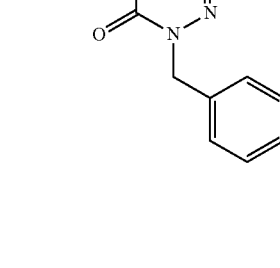 | 571 | 2.11 LCMSBAS1 |

-continued

| # | Structure | MS (M + H)⁺ | $t_{Ret.}$ HPLC [min] HPLC method |
|---|---|---|---|
| II-6 | 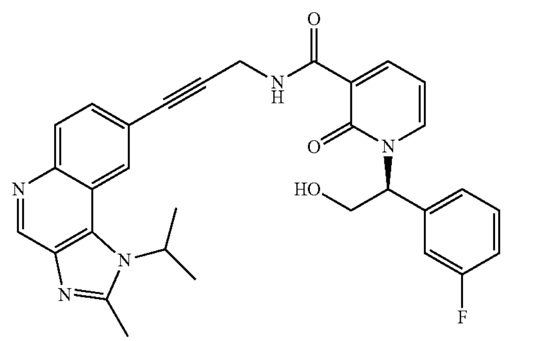 [SMILES: Cc1nc2cnc3ccc(C#CCNC(=O)c4cccn([C@H](CO)c5cccc(F)c5)c4=O)cc3c2n1C(C)C] | 538 | 1.67 LCMSBAS1 |
| II-7 | 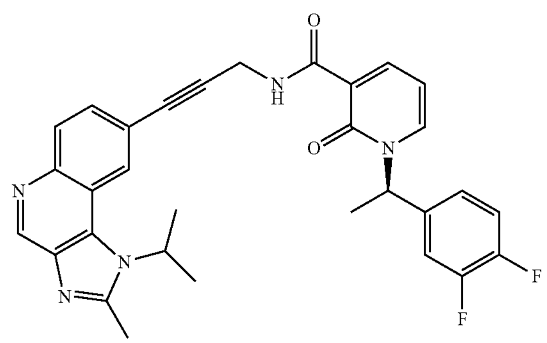 [SMILES: Cc1nc2cnc3ccc(C#CCNC(=O)c4cccn([C@H](C)c5ccc(F)c(F)c5)c4=O)cc3c2n1C(C)C] | 540 | 1.87 LCMSBAS1 |
| II-8 | 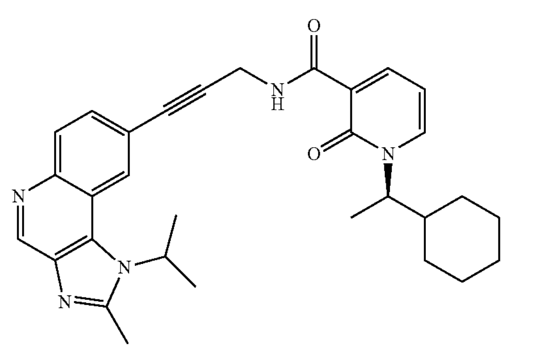 [SMILES: Cc1nc2cnc3ccc(C#CCNC(=O)c4cccn([C@H](C)C5CCCCC5)c4=O)cc3c2n1C(C)C] | 510 | 2.15 LCMSBAS1 |
| II-9 | 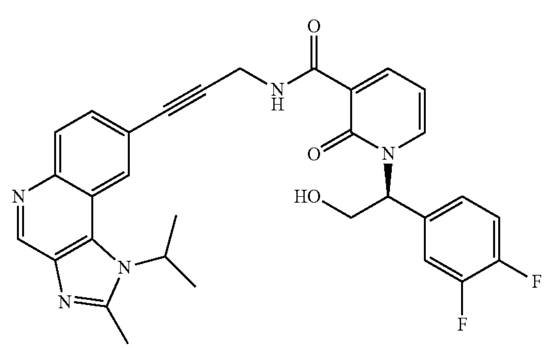 [SMILES: Cc1nc2cnc3ccc(C#CCNC(=O)c4cccn([C@H](CO)c5ccc(F)c(F)c5)c4=O)cc3c2n1C(C)C] | 556 | 1.68 LCMSBAS1 |

-continued

| # | Structure | MS (M + H)+ | t_Ret. HPLC [min] HPLC method |
|---|---|---|---|
| II-10 | 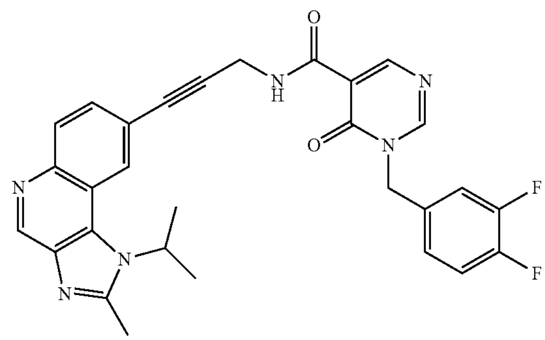 [SMILES: Cc1nc2cnc3ccc(C#CCNC(=O)c4cncn(Cc5ccc(F)c(F)c5)c4=O)cc3c2n1C(C)C] | 527 | 2.72 LCMSBAS1 |
| II-11 | 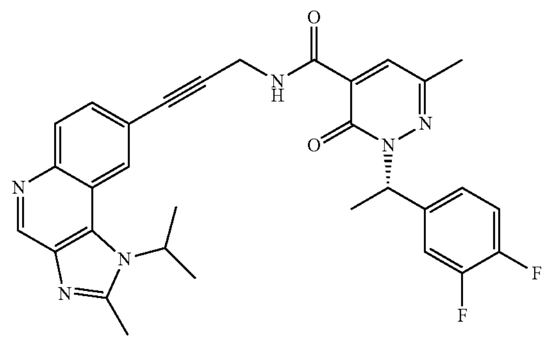 [SMILES: Cc1cc(C(=O)NCC#Cc2ccc3ncc4nc(C)n(C(C)C)c4c3c2)c(=O)n([C@@H](C)c2ccc(F)c(F)c2)n1] | 555 | 2.07 LCMSBAS1 |
| II-12 | 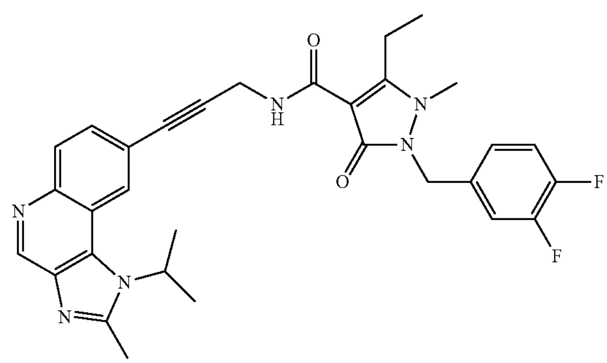 [SMILES: CCc1c(C(=O)NCC#Cc2ccc3ncc4nc(C)n(C(C)C)c4c3c2)c(=O)n(Cc2ccc(F)c(F)c2)n1C] | 557 | 1.76 LCMSBAS1 |
| II-13 | 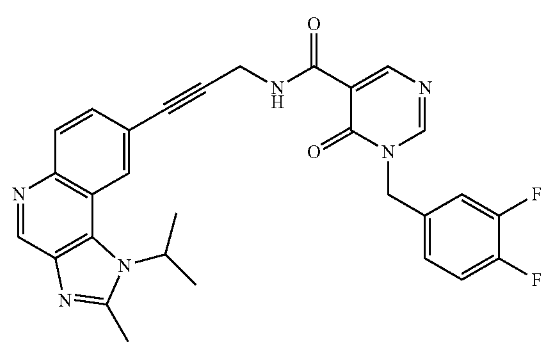 [SMILES: Cc1nc2cnc3ccc(C#CCNC(=O)c4cncn(Cc5ccc(F)c(F)c5)c4=O)cc3c2n1C(C)C] | 527 | 1.78 LCMSBAS1 |

-continued
| # | Structure | MS (M + H)+ | t_Ret. HPLC [min] HPLC method |
|---|---|---|---|
| II-14 | 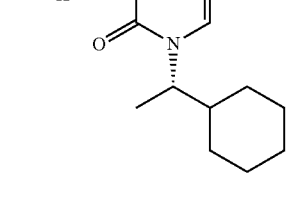 | 510 | 2.03 LCMSBAS1 |
| II-15 | 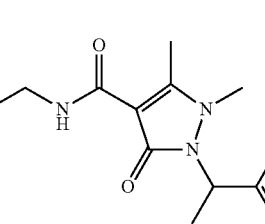 | 557 | 1.75 LCMSBAS1 |
| II-16 | 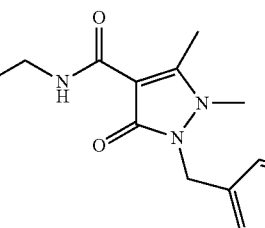 | 543 | 1.38 LCMSBAS1 |
| II-17 | 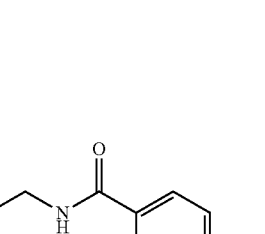 | 540 | 1.87 LCMSBAS1 |

-continued
| # | Structure | MS (M + H)+ | t_Ret. HPLC [min] HPLC method |
|---|---|---|---|
| II-18 | 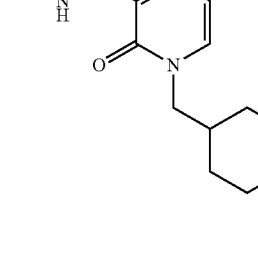 | 496 | 1.95 LCMSBAS1 |
| II-19 | 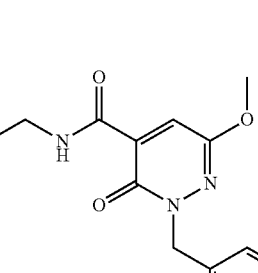 | 557 | 1.99 LCMSBAS1 |
| II-20 | 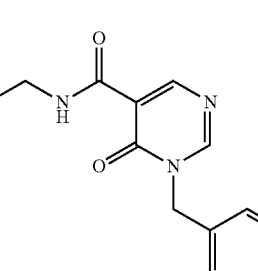 | 527 | 1.72 LCMSBAS1 |
| II-21 | 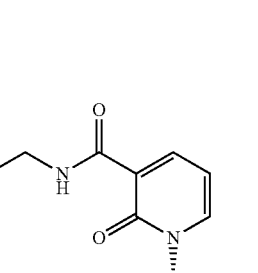 | 520 | 1.67 LCMSBAS1 |

-continued

| # | Structure | MS (M + H)+ | t_Ret. HPLC [min] HPLC method |
|---|---|---|---|
| II-22 | 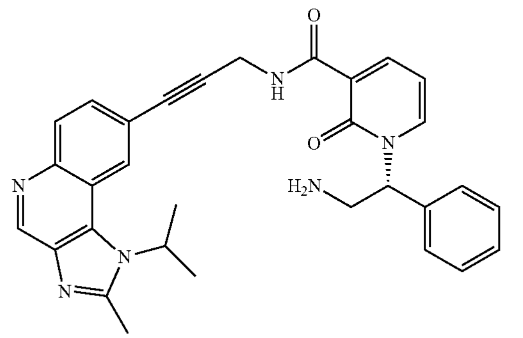 [SMILES: Cc1nc2cnc3ccc(C#CCNC(=O)c4cccn([C@@H](CN)c5ccccc5)c4=O)cc3c2n1C(C)C] | 519 | 1.61 LCMSBAS1 |
| II-23 | 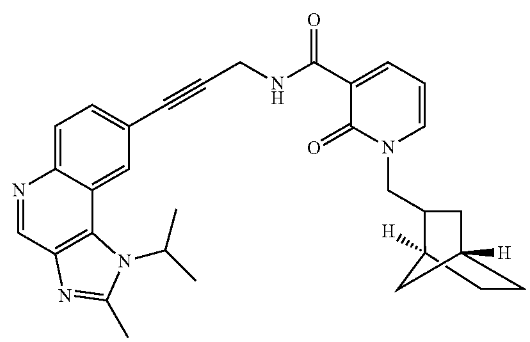 [SMILES: Cc1nc2cnc3ccc(C#CCNC(=O)c4cccn(CC5C[C@@H]6CC[C@H]5C6)c4=O)cc3c2n1C(C)C] | 508 | 2.08 LCMSBAS1 |
| II-24 | 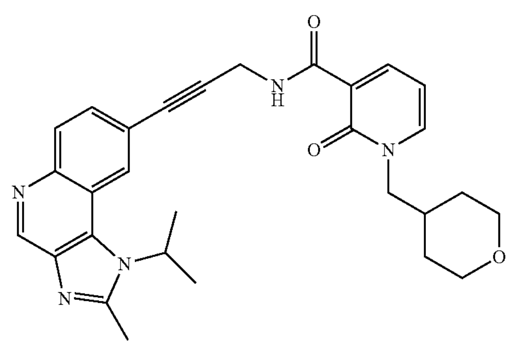 [SMILES: Cc1nc2cnc3ccc(C#CCNC(=O)c4cccn(CC5CCOCC5)c4=O)cc3c2n1C(C)C] | 498 | 1.56 LCMSBAS1 |
| II-25 | 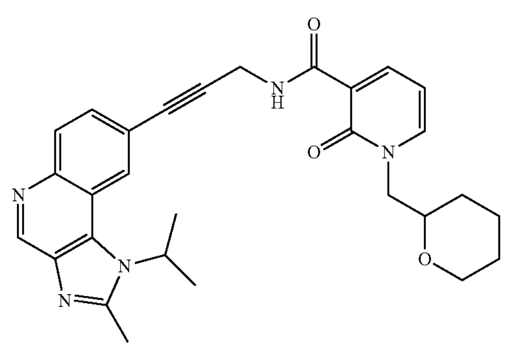 | 498 | 1.56 LCMSBAS1 |

-continued

| # | Structure | MS (M + H)⁺ | t$_{Ret.}$ HPLC [min] HPLC method |
|---|---|---|---|
| II-26 | 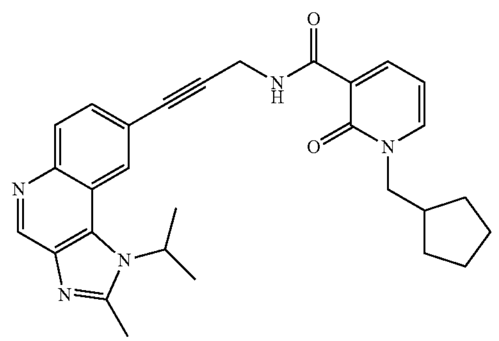 [SMILES: Cc1nc2cnc3ccc(C#CCNC(=O)c4cccn(CC5CCCC5)c4=O)cc3c2n1C(C)C] | 482 | 1.87 LCMSBAS1 |
| II-27 | 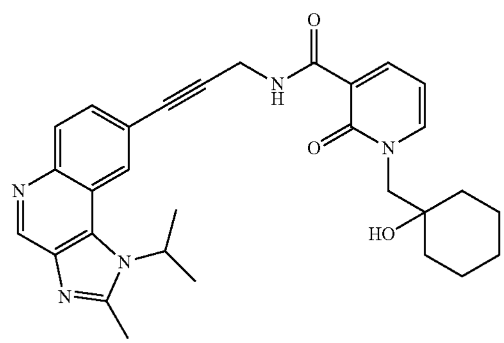 [SMILES: Cc1nc2cnc3ccc(C#CCNC(=O)c4cccn(CC5(O)CCCCC5)c4=O)cc3c2n1C(C)C] | 512 | 1.71 LCMSBAS1 |
| II-28 | 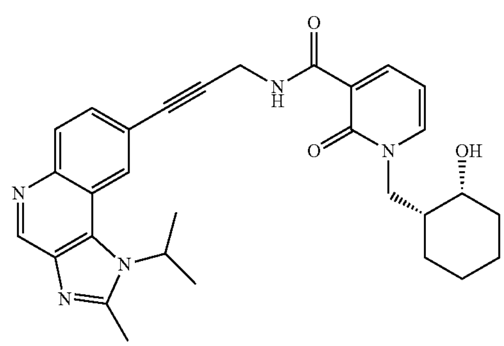 [SMILES: Cc1nc2cnc3ccc(C#CCNC(=O)c4cccn(C[C@H]5CCCC[C@H]5O)c4=O)cc3c2n1C(C)C] | 512 | 1.75 LCMSBAS1 |
| II-29 | 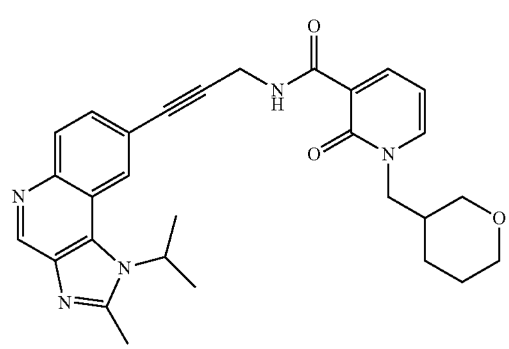 [SMILES: Cc1nc2cnc3ccc(C#CCNC(=O)c4cccn(CC5CCCOC5)c4=O)cc3c2n1C(C)C] | 498 | 1.60 LCMSBAS1 |

-continued

| # | Structure | MS (M + H)+ | t_Ret. HPLC [min] HPLC method |
|---|---|---|---|
| II-30 | 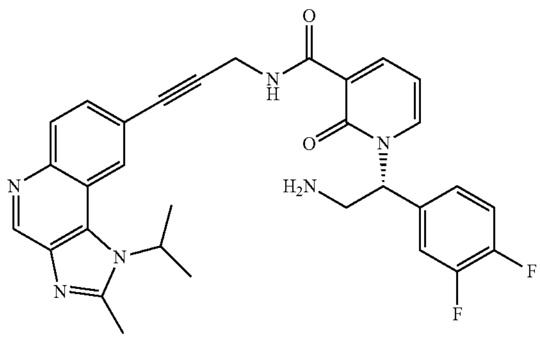 [SMILES: Cc1nc2cnc3ccc(C#CCNC(=O)c4cccn([C@@H](CN)c5ccc(F)c(F)c5)c4=O)cc3c2n1C(C)C] | 555 | 1.67 LCMSBAS1 |
| II-31 | 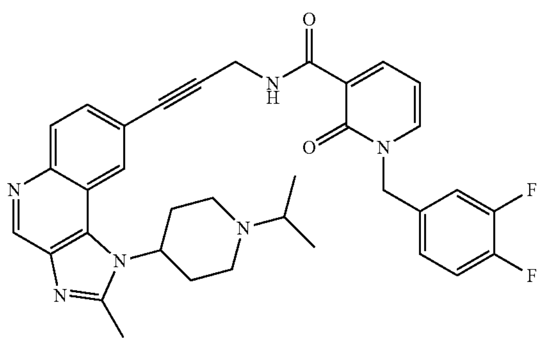 [SMILES: Cc1nc2cnc3ccc(C#CCNC(=O)c4cccn(Cc5ccc(F)c(F)c5)c4=O)cc3c2n1C1CCN(C(C)C)CC1] | 609 | 1.89 LCMSBAS1 |
| II-32 | 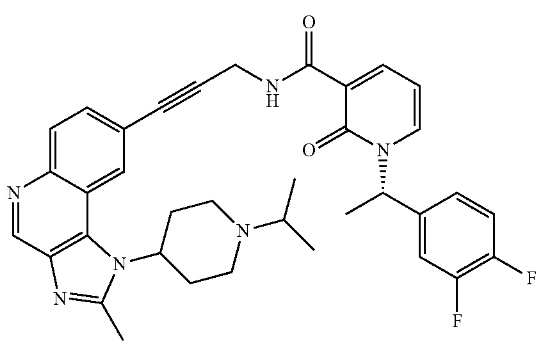 [SMILES: Cc1nc2cnc3ccc(C#CCNC(=O)c4cccn([C@@H](C)c5ccc(F)c(F)c5)c4=O)cc3c2n1C1CCN(C(C)C)CC1] | 623 | 1.90 LCMSBAS1 |
| II-33 | 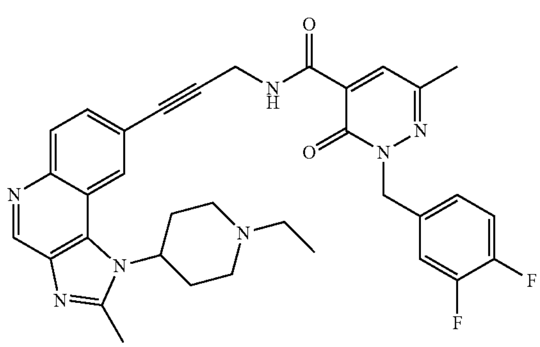 | 638 | 2.25 LCMSBAS1 |

| # | Structure | MS (M + H)+ | t_Ret. HPLC [min] HPLC method |
|---|---|---|---|
| II-34 | 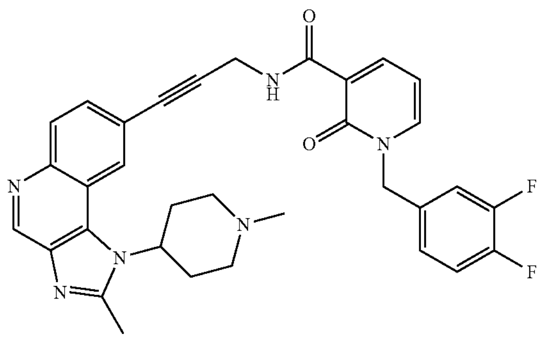 [SMILES: Cc1nc2cnc3ccc(C#CCNC(=O)c4cccn(Cc5ccc(F)c(F)c5)c4=O)cc3c2n1C1CCN(C)CC1] | 581 | 1.73 LCMSBAS1 |
| II-35 | 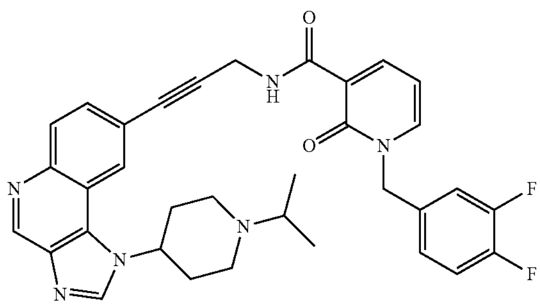 | 595 | 1.82 LCMSBAS1 |
| III-1 | 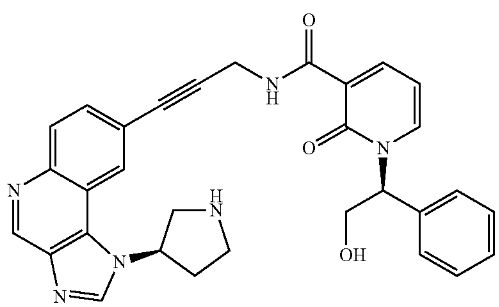 [SMILES: O=C(NCC#Cc1ccc2ncc3ncn([C@@H]4CCNC4)c3c2c1)c1cccn([C@H](CO)c2ccccc2)c1=O] | 533 | 1.44 LCMSBAS1 |
| III-2 | 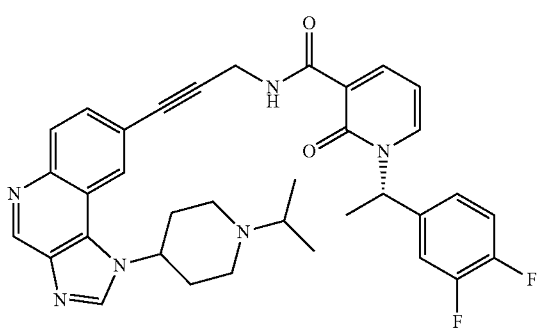 [SMILES: CC(C)N1CCC(n2cnc3cnc4ccc(C#CCNC(=O)c5cccn([C@@H](C)c6ccc(F)c(F)c6)c5=O)cc4c32)CC1] | 609 | 1.93 LCMSBAS1 |
| III-3 | 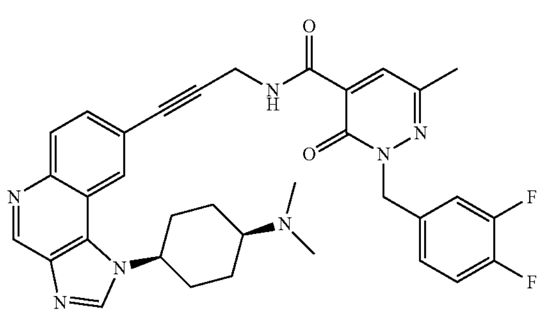 [SMILES: Cc1cc(C(=O)NCC#Cc2ccc3ncc4ncn([C@H]5CC[C@@H](N(C)C)CC5)c4c3c2)c(=O)n(Cc2ccc(F)c(F)c2)n1] | 610 | 2.06 LCMSBAS1 |

-continued
| # | Structure | MS (M + H)+ | t_Ret. HPLC [min] HPLC method |
|---|---|---|---|
| III-4 | 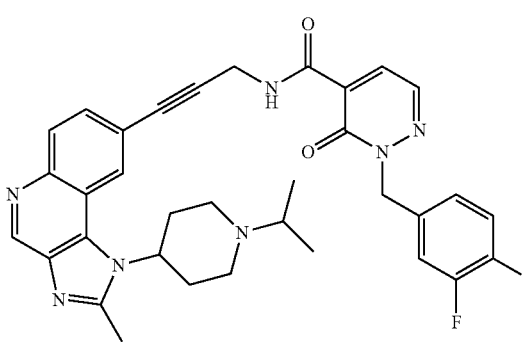 | 610 | 2.06 LCMSBAS1 |
| III-5 | 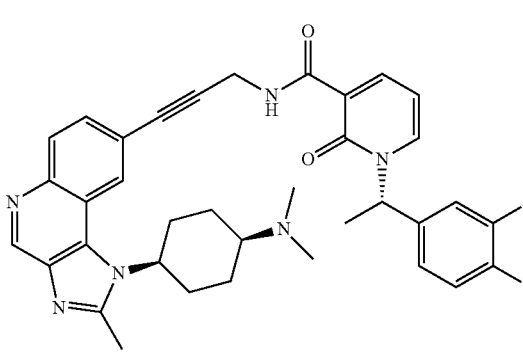 | 623 | 2.13 LCMSBAS1 |
| III-6 | 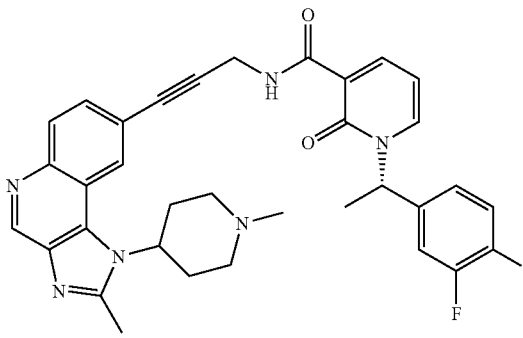 | 595 | 1.82 LCMSBAS1 |
| III-7 | 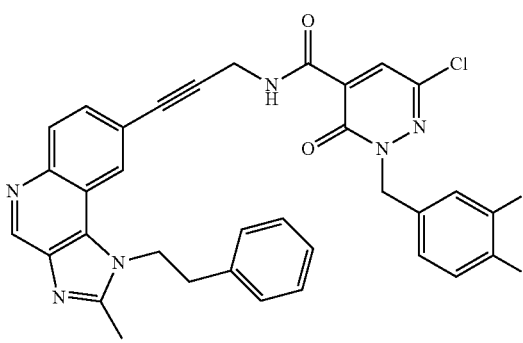 | 625 | 1.78 LCMSBAS1 |

| # | Structure | MS (M + H)+ | t_Ret. HPLC [min] HPLC method |
|---|---|---|---|
| III-8 | 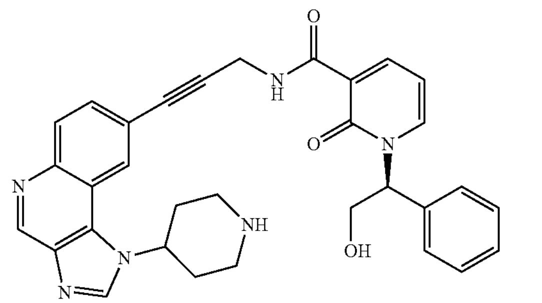 [SMILES: O=C(NCC#Cc1ccc2ncc3ncn(C4CCNCC4)c3c2c1)c1cccn([C@H](CO)c2ccccc2)c1=O] | 547 | 1.48 LCMSBAS1 |
| III-9 | 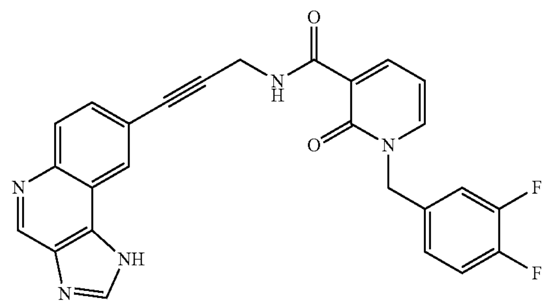 [SMILES: O=C(NCC#Cc1ccc2ncc3nc[nH]c3c2c1)c1cccn(Cc2ccc(F)c(F)c2)c1=O] | 468 | 1.42 LCMSBAS1 |
| III-10 | 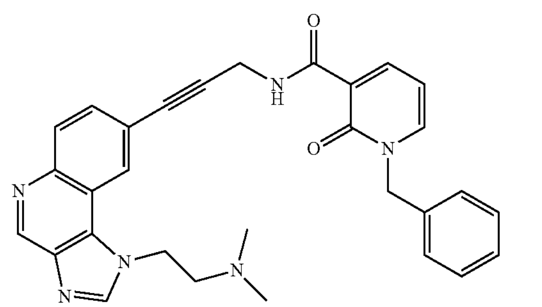 [SMILES: CN(C)CCn1cnc2cnc3ccc(C#CCNC(=O)c4cccn(Cc5ccccc5)c4=O)cc3c21] | 505 | 1.64 LCMSBAS1 |
| III-11 | 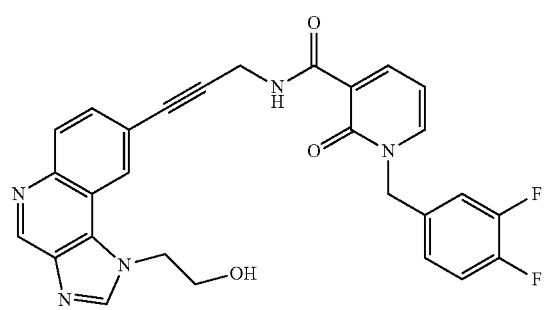 [SMILES: O=C(NCC#Cc1ccc2ncc3ncn(CCO)c3c2c1)c1cccn(Cc2ccc(F)c(F)c2)c1=O] | 514 | 1.55 LCMSBAS1 |
| III-12 | 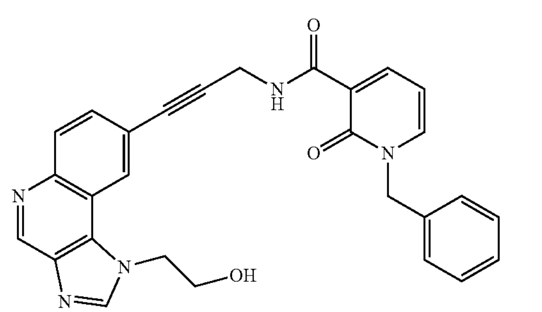 [SMILES: O=C(NCC#Cc1ccc2ncc3ncn(CCO)c3c2c1)c1cccn(Cc2ccccc2)c1=O] | 478 | 1.49 LCMSBAS1 |

| # | Structure | MS (M + H)+ | t_Ret. HPLC [min] HPLC method |
|---|---|---|---|
| III-13 | 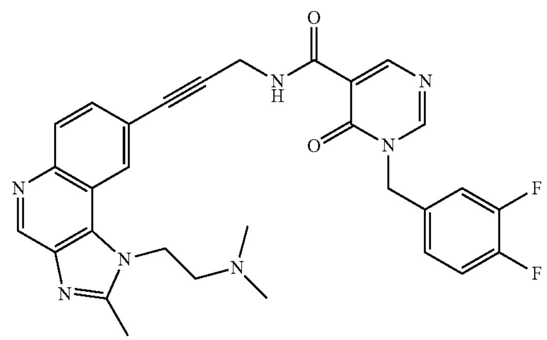 [SMILES: Cc1nc2cnc3ccc(C#CCNC(=O)c4cncn(Cc5ccc(F)c(F)c5)c4=O)cc3c2n1CCN(C)C] | 556 | 1.64 LCMSBAS1 |
| III-14 | 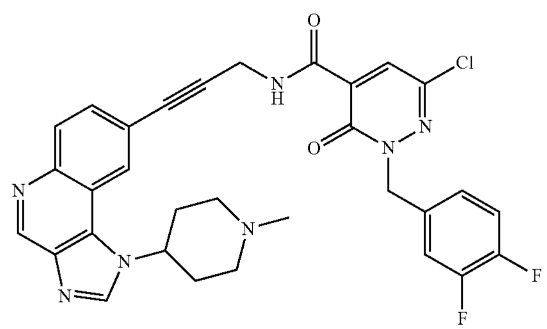 [SMILES: CN1CCC(n2cnc3cnc4ccc(C#CCNC(=O)c5cc(Cl)nn(Cc6ccc(F)c(F)c6)c5=O)cc4c32)CC1] | 604 | 1.92 LCMSBAS1 |
| III-15 | 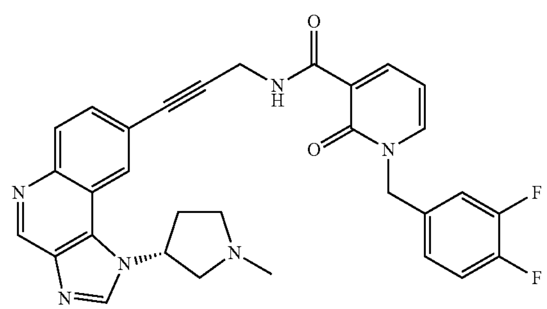 [SMILES: CN1CC[C@@H](n2cnc3cnc4ccc(C#CCNC(=O)c5cccn(Cc6ccc(F)c(F)c6)c5=O)cc4c32)C1] | 553 | 1.74 LCMSBAS1 |
| III-16 | 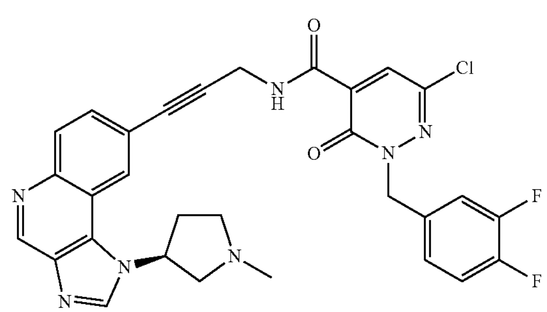 [SMILES: CN1CC[C@H](n2cnc3cnc4ccc(C#CCNC(=O)c5cc(Cl)nn(Cc6ccc(F)c(F)c6)c5=O)cc4c32)C1] | 588 | 1.97 LCMSBAS1 |

-continued
| # | Structure | MS (M + H)+ | t_Ret. HPLC [min] HPLC method |
|---|---|---|---|
| III-17 | 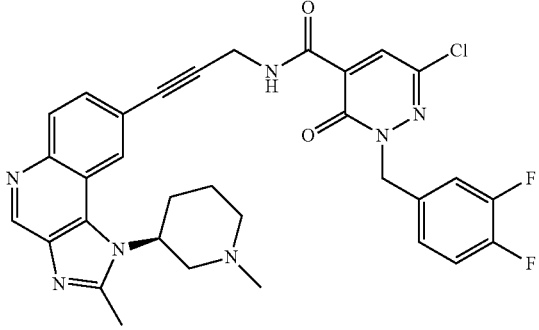 [SMILES: Cc1nc2cnc3ccc(C#CCNC(=O)c4cc(Cl)nn(Cc5ccc(F)c(F)c5)c4=O)cc3c2n1[C@H]1CCCN(C)C1] | 614 | 1.91 LCMSBAS1 |
| III-18 | 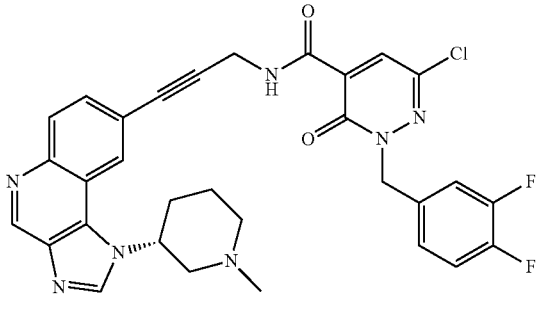 [SMILES: CN1CCC[C@@H](n2cnc3cnc4ccc(C#CCNC(=O)c5cc(Cl)nn(Cc6ccc(F)c(F)c6)c5=O)cc4c32)C1] | 602 | 1.92 LCMSBAS1 |
| III-19 | 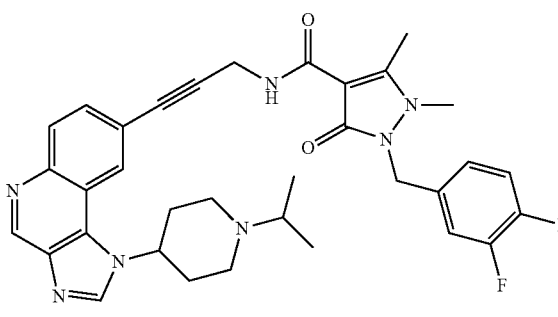 | 612 | 1.71 LCMSBAS1 |
| III-20 | 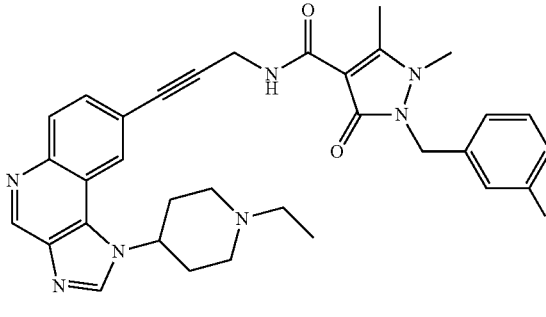 | 598 | 1.64 LCMSBAS1 |

-continued

| # | Structure | MS (M + H)+ | t_Ret. HPLC [min] HPLC method |
|---|---|---|---|
| III-21 | 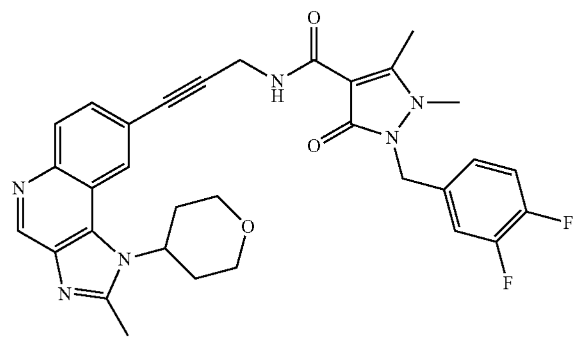 [SMILES: Cc1nc2cnc3ccc(C#CCNC(=O)c4c(C)n(C)n(Cc5ccc(F)c(F)c5)c4=O)cc3c2n1C1CCOCC1] | 585 | 1.60 LCMSBAS1 |
| III-22 | 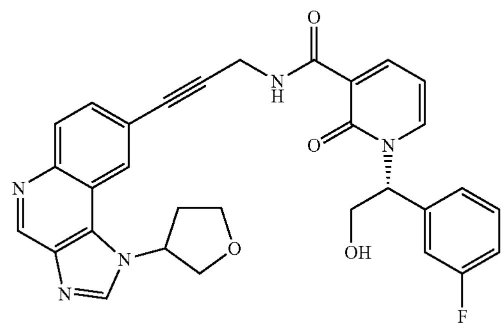 [SMILES: O=C(NCC#Cc1ccc2ncc3ncn(C4CCOC4)c3c2c1)c1cccn([C@@H](CO)c2cccc(F)c2)c1=O] | 552 | 1.55 LCMSBAS1 |
| III-23 | 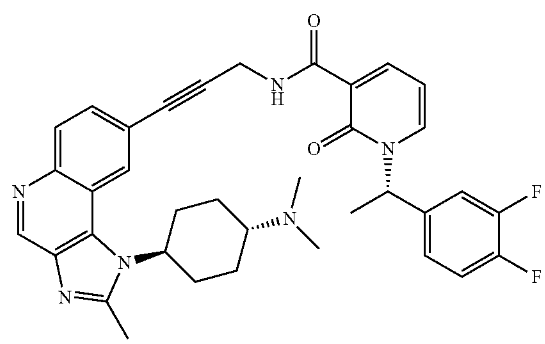 [SMILES: Cc1nc2cnc3ccc(C#CCNC(=O)c4cccn([C@@H](C)c5ccc(F)c(F)c5)c4=O)cc3c2n1[C@H]1CC[C@H](N(C)C)CC1] | 623 | 1.91 LCMSBAS1 |
| III-24 | 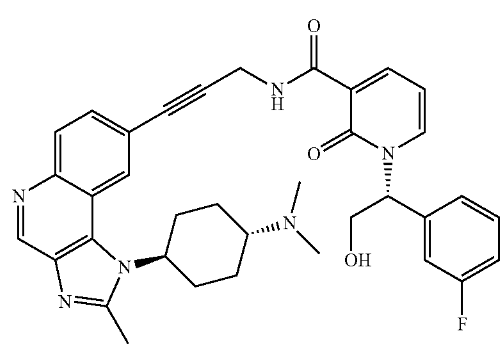 [SMILES: Cc1nc2cnc3ccc(C#CCNC(=O)c4cccn([C@@H](CO)c5cccc(F)c5)c4=O)cc3c2n1[C@H]1CC[C@H](N(C)C)CC1] | 621 | 1.70 LCMSBAS1 |

-continued

| # | Structure | MS (M + H)+ | t_Ret. HPLC [min] HPLC method |
|---|---|---|---|
| III-25 | 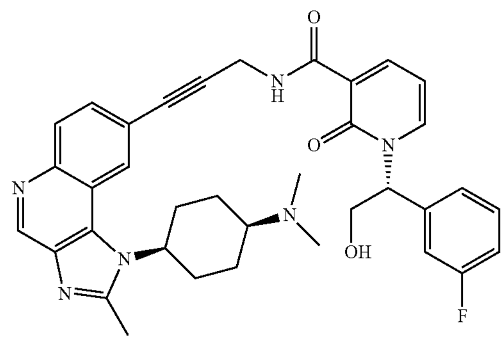 [SMILES: Cc1nc2cnc3ccc(C#CCNC(=O)c4cccn([C@@H](CO)c5cccc(F)c5)c4=O)cc3c2n1[C@H]1CC[C@@H](N(C)C)CC1] | 621 | 1.70 LCMSBAS1 |
| III-26 | 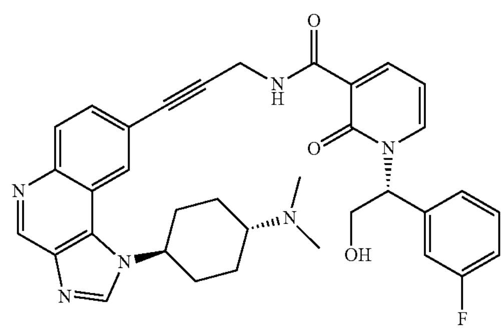 [SMILES: CN(C)[C@H]1CC[C@H](n2cnc3cnc4ccc(C#CCNC(=O)c5cccn([C@@H](CO)c6cccc(F)c6)c5=O)cc4c32)CC1] | 607 | 1.68 LCMSBAS1 |
| III-27 | 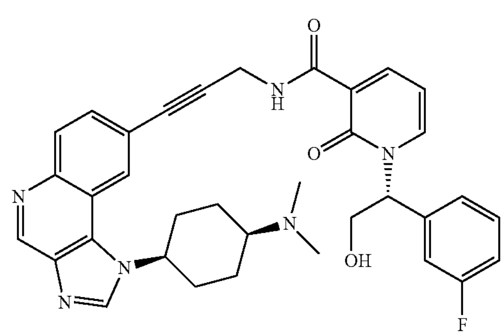 [SMILES: CN(C)[C@H]1CC[C@@H](n2cnc3cnc4ccc(C#CCNC(=O)c5cccn([C@@H](CO)c6cccc(F)c6)c5=O)cc4c32)CC1] | 607 | 1.75 LCMSBAS1 |
| III-28 | 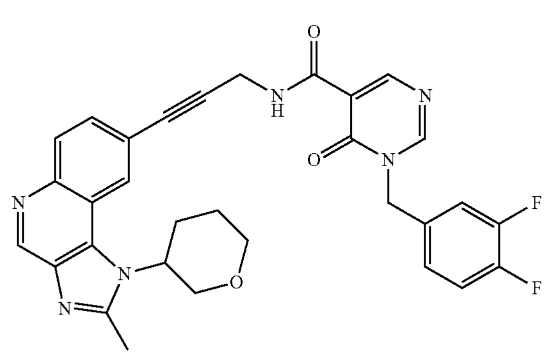 [SMILES: Cc1nc2cnc3ccc(C#CCNC(=O)c4cncn(Cc5ccc(F)c(F)c5)c4=O)cc3c2n1C1CCCOC1] | 569 | 1.70 LCMSBAS1 |

-continued

| # | Structure | MS (M + H)+ | t_Ret. HPLC [min] HPLC method |
|---|---|---|---|
| III-29 | 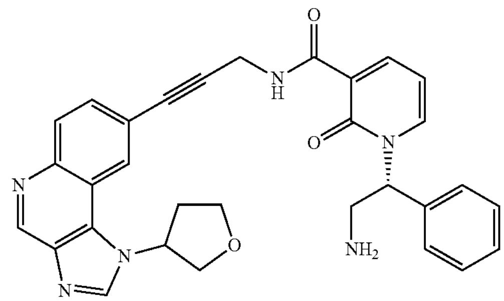 [SMILES: NC[C@@H](c1ccccc1)n1cccc(C(=O)NCC#Cc2ccc3ncc4ncn(C5CCOC5)c4c3c2)c1=O] | 533 | 1.48 LCMSBAS1 |
| III-30 | 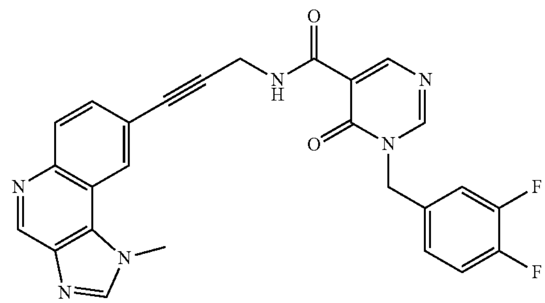 [SMILES: Cn1cnc2cnc3ccc(C#CCNC(=O)c4cncn(Cc5ccc(F)c(F)c5)c4=O)cc3c21] | 485 | 1.55 LCMSBAS1 |
| III-31 | 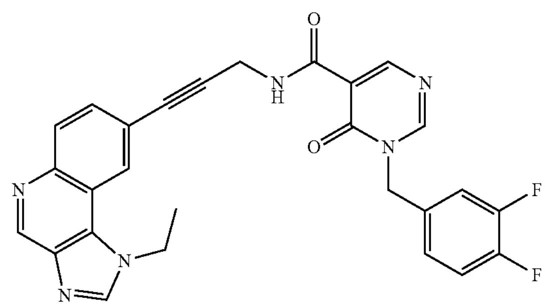 [SMILES: CCn1cnc2cnc3ccc(C#CCNC(=O)c4cncn(Cc5ccc(F)c(F)c5)c4=O)cc3c21] | 499 | 1.62 LCMSBAS1 |
| III-32 | 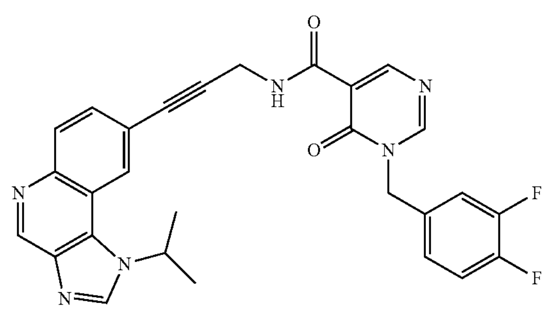 [SMILES: CC(C)n1cnc2cnc3ccc(C#CCNC(=O)c4cncn(Cc5ccc(F)c(F)c5)c4=O)cc3c21] | 513 | 1.68 LCMSBAS1 |
| III-33 | 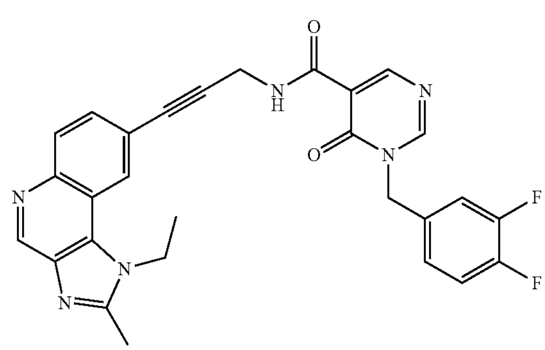 [SMILES: CCn1c(C)nc2cnc3ccc(C#CCNC(=O)c4cncn(Cc5ccc(F)c(F)c5)c4=O)cc3c21] | 513 | 1.65 LCMSBAS1 |

| # | Structure | MS (M + H)+ | $t_{Ret.}$ HPLC [min] HPLC method |
|---|---|---|---|
| III-34 | 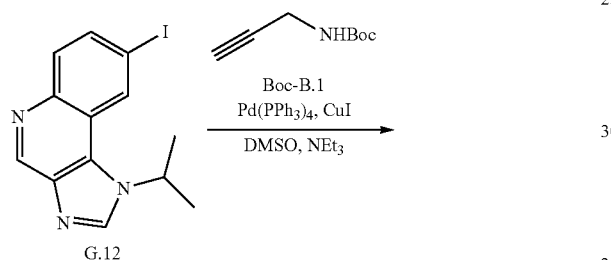 | 499 | 1.59 LCMSBAS1 |

Synthesis of Compounds (1) According to the Invention Using Method 2:

Method for synthesising 3-(1-isopropyl-1H-imidazo[4,5-c]quinolin-8-yl)-prop-2-ynylamine H.1

8-Iodo-1-isopropyl-1H-imidazo[4,5-c]quinoline G.12 (1.9 g, 5.5 mmol), tetrakis(triphenylphosphine)palladium(0) (192 mg, 0.2 mmol, 10 mol %) and copper(I)iodide (21 mg, 0.1 mmol, 5 mol %) are taken up in DMSO (15 mL), combined with DIPEA (4.5 mL, 27.7 mmol) and N-Boc-propargylamine Boc-B.1 (1.1 g, 6.7 mmol) and stirred for 22 h at 20° C. The reaction mixture is purified by prep. HPLC/MS (basic modifier) and intermediate product Z.8 (1.62 g, 80%) is obtained.

Intermediate product Z.8 (1.62 g, 4.5 mmol) is taken up in dioxane (5 mL), combined with HCl (15 mL, 60 mmol, in dioxane) and stirred for 30 min at 20° C. The precipitate is filtered off, washed with dioxane (20 mL) and diethyl ether (3×75 mL), dried and product H.1 (1.45 g, 54%) is obtained.

Method for synthesising 2-(3,4-difluorobenzyl)-6-ethoxy-3-oxo-2,3-dihydro-pyridazine-4-carboxylic acid [3-(1-isopropyl-1H-imidazo[4,5-c]quinolin-8-yl)-prop-2-ynyl]-amide IV-1

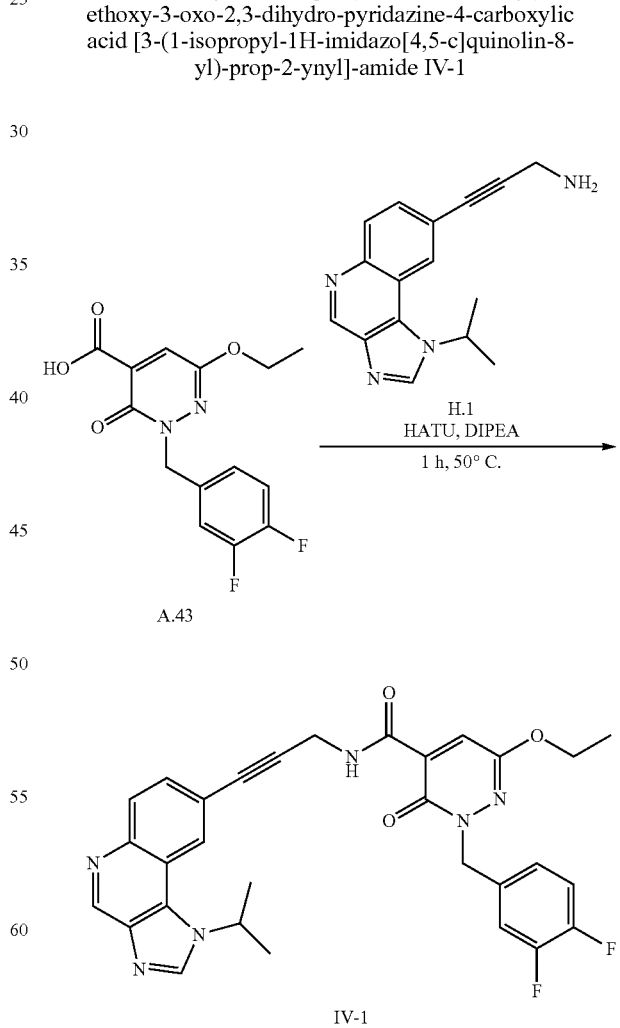

Carboxylic acid A.43 (55 mg, 0.16 mmol) is placed in DMSO (500 μL), combined with DIPEA (89 μL, 0.5 mmol)

and HATU (91 mg, 0.24 mmol) and stirred for 10 min at 20° C. Then amine H.1 (95 mg, 0.16 mmol) is added and the reaction mixture is heated to 50° C. for 1 h. The reaction mixture is purified by prep. HPLC/MS (basic modifier) and product IV-1 (15 mg, 17%; HPLC-MS: MS (M+H)$^+$=557; $t_{Ret.}$=2.07 min; method LCMSBAS1) is obtained (Table 11).

| # | Structure | MS (M + H)$^+$ | $t_{Ret.}$ HPLC [min] HPLC method |
|---|---|---|---|
| IV-1 | | 557 | 2.07 LCMSBAS1 | e) Synthesis of compounds (1) according to the invention via activated imidazo[4,5-c]quinolines G

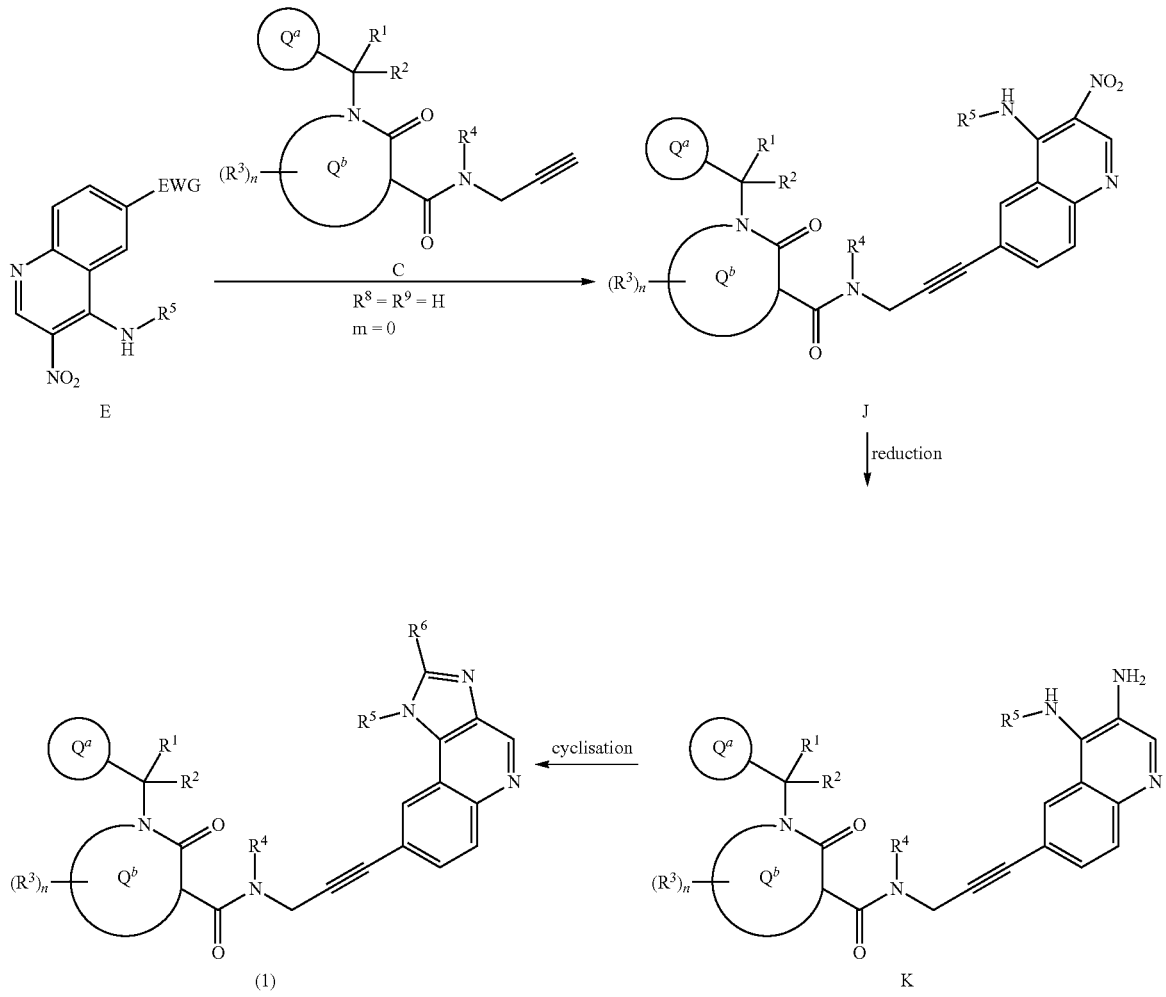

Reaction scheme E

Alternatively to the procedure according to Reaction scheme D the compounds (1) according to the invention may also be prepared by another method of synthesis starting from activated nitroquinolines E (Reaction scheme E). In a first step the nitroquinolines E are coupled with propargylamides C in a SONOGASHIRA reaction, the intermediates J obtained are reduced to form the diamines K and only then is cyclisation completed (analogously to the reaction of intermediates F to form G with e.g. orthocarbonates, orthocarboxylic acid esters, acid chlorides or aldehydes) to form the end compounds (1).

Method for Synthesising Intermediates J

The SONOGASHIRA reaction is carried out analogously to the conditions of the synthesis of Example compound I-1 as hereinbefore described with the corresponding components E and C (Table 12).

| # | Structure | MS (M + H)+ | $t_{Ret.}$ HPLC [min] HPLC method |
|---|-----------|-------------|------------------------------------|
| J.1 | 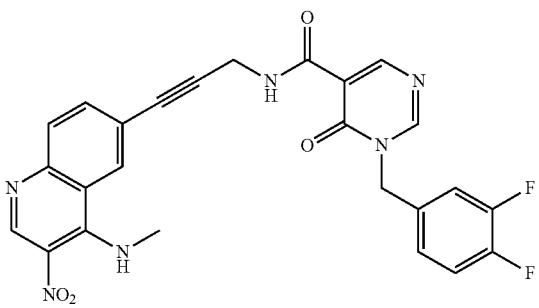 [SMILES: CNc1c([N+](=O)[O-])cnc2ccc(C#CCNC(=O)c3cncn(Cc4ccc(F)c(F)c4)c3=O)cc12] | 505 | 0.988 1_FEC |
| J.2 | 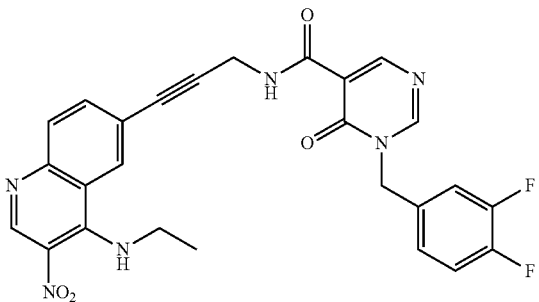 [SMILES: CCNc1c(N)cnc2ccc(C#CCNC(=O)c3cncn(Cc4ccc(F)c(F)c4)c3=O)cc12] | 519 | 1.126 1_FEC |
| J.3 | 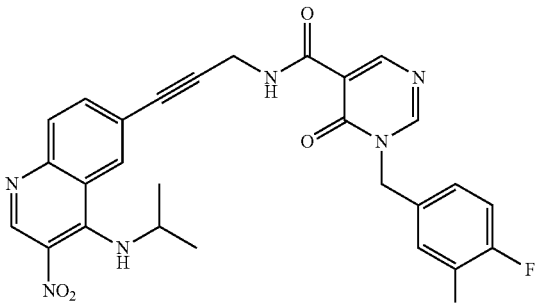 | 533 | 1.224 1_FEC |

Method for Synthesising Reduced Intermediates K (Diamines)

The reduction of the intermediates J is carried out analogously to the conditions of the reduction of E.1 to F.1 as hereinbefore described (Table 13).

| # | Structure | MS (M + H)⁺ | $t_{Ret.}$ HPLC [min] HPLC method |
|---|---|---|---|
| K.1 | 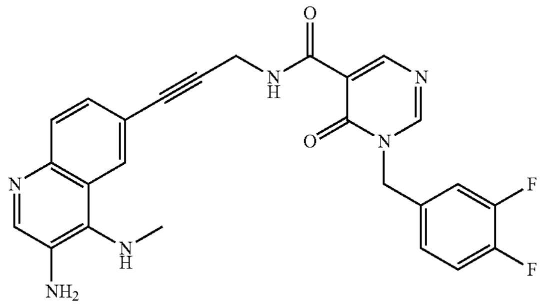 | 475 | 0.761<br>1_FEC |
| K.2 | 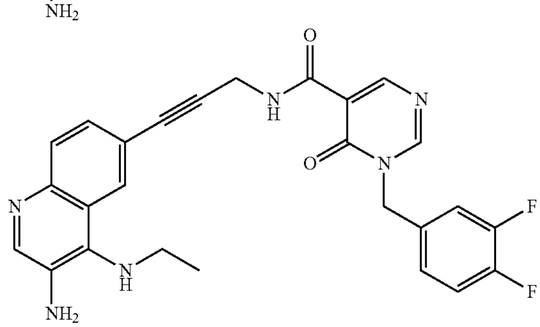 | 489 | 0.843<br>1_FEC |
| K.3 | 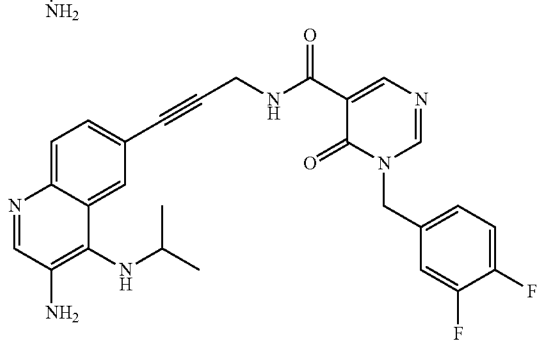 | 503 | 0.794<br>1_FEC |

Cyclisation Variant 1:

Method of synthesising 1-(3,4-difluoro-benzyl)-6-oxo-1,6-dihydro-pyrimidine-5-carboxylic acid [3-(2-ethoxy-1-methyl-1H-imidazo[4,5-c]quinolin-8-yl)-prop-2-ynyl]-amide (V-1)

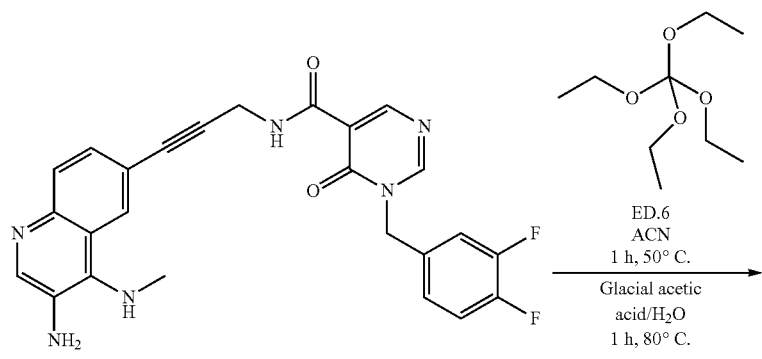

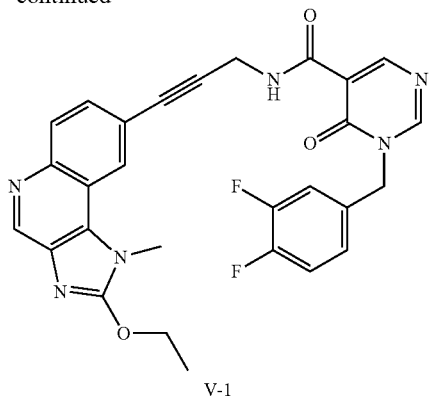

V-1

Diamine K.1 (50 mg, 0.1 mmol) is placed in acetonitrile (1 mL), combined with tetraethylorthocarbonate ED.6 (235 mg, 1.1 mmol) and stirred for 1 h at 50° C. The reaction mixture is combined with glacial acetic acid (1 mL) and water (0.5 mL), stirred for 1 h at 80° C., the solvent is eliminated, the residue is purified by prep. HPLC (ACN/water, HCOOH as modifier) and example compound V-1 (59 mg, 72%; HPLC-MS: MS $(M+H)^+=529$; $t_{Ret.}=1.76$ min; method LCMSBAS1) is obtained.

The example compounds V-2-V.4 are synthesised analogously to compound V-1 (Table 14).

Cyclisation Variant 2:

Method of synthesising 1-(3,4-difluoro-benzyl)-6-oxo-1,6-dihydro-pyrimidine-5-carboxylic acid {3-[2-(2-methoxy-ethyl)-1-methyl-1H-imidazo[4,5-c]quinolin-8-yl]-prop-2-ynyl}-amide (V-5)

Diamine K.1 (50 mg, 0.10 mmol) is placed in THF (1 mL), combined with 3-methoxypropionic acid chloride ED.7 (16 mg, 0.14 mmol) in THF (1 mL) and the reaction mixture is stirred for 30 min at 50° C. The solvent is removed, the residue is taken up in glacial acetic acid (1 mL) and stirred for 1 h at 90° C. Then the reaction mixture is combined with ethyl acetate (2 mL), heated for 10 min at 130° C. and for 15 min at 145° C. in the microwave reactor, then purified by prep. HPLC/MS (MeOH/water, $NH_3/NH_4HCO_3$ as modifier) and example compound V-5 (12 mg, 20%; HPLC-MS: MS $(M+H)^+=543$; $t_{Ret.}=1.65$ min; method LCMSBAS1) is obtained (Table 14).

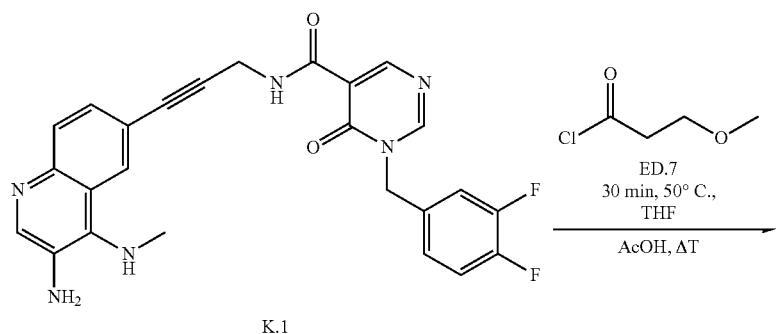

K.1

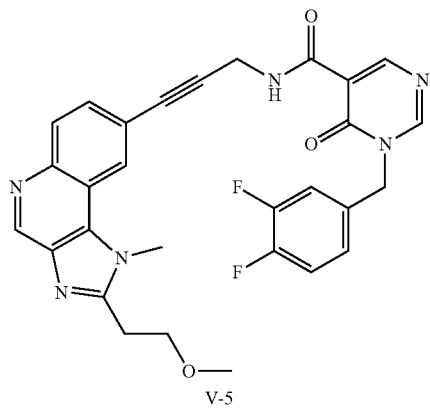

V-5

Cyclisation Variant 3:

Method of synthesising 1-(3,4-difluoro-benzyl)-6-oxo-1,6-dihydro-pyrimidine-5-carboxylic acid [3-(2-fluoromethyl-1-methyl-1H-imidazo[4,5-c]quinolin-8-yl)-prop-2-ynyl]-amide (V-6)

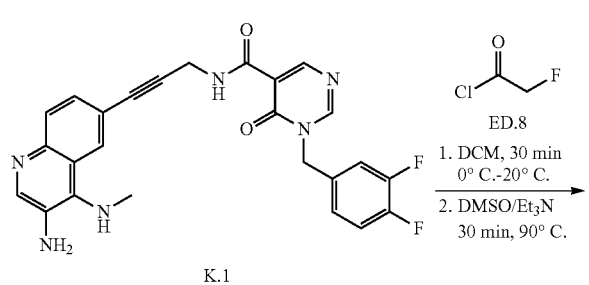

Diamine K.1 (55 mg, 0.1 mmol) is placed in DCM (1 mL), mixed with triethylamine (18 mg, 0.2 mmol) and cooled to 0° C. Fluoroacetyl chloride ED.8 (18 mg, 0.2 mmol) in DCM (1 mL) is added dropwise within 1 min, the reaction mixture is heated to 20° C. and stirred for 30 min at 20° C. The solvent is removed, the residue is taken up in DMSO (1 mL) and triethylamine (24 mg, 0.2 mmol) and heated for 30 min to 90° C. The reaction mixture is purified directly by prep. HPLC/MS (MeOH/water, $NH_3/NH_4HCO_3$ as modifier) and example compound V-6 (11 mg, 18%; HPLC-MS: MS $(M+H)^+=517$; $t_{Ret.}=1.65$ min; method LCMSBAS1) is obtained.

Example compound V-7 is synthesised analogously to V-6 (Table 14).

Cyclisation Variant 4:

Method of synthesising 1-(3,4-difluoro-benzyl)-6-oxo-1,6-dihydro-pyrimidine-5-carboxylic acid [3-(2-dimethylaminomethyl-1-methyl-1H-imidazo[4,5-c]quinolin-8-yl)-prop-2-ynyl]-amide (V-8)

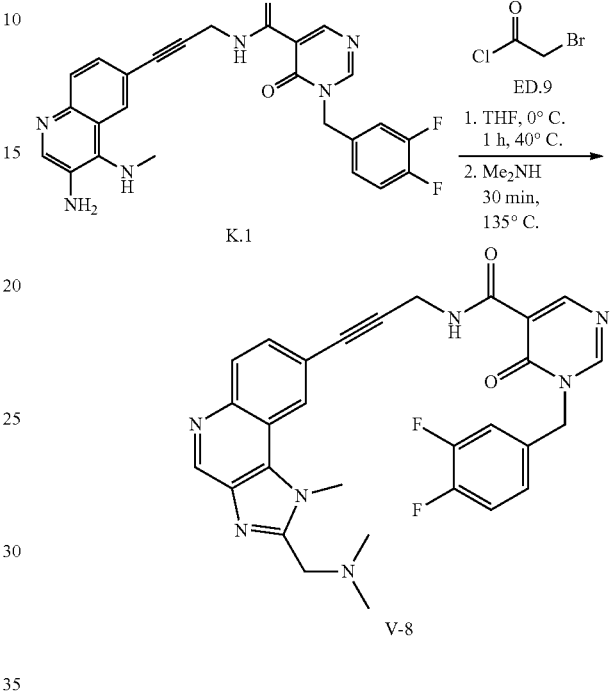

Diamine K.1 (60 mg, 0.1 mmol) is placed in THF (1 mL), cooled to 0° C., combined with bromoacetyl chloride ED.9 (23.9 mg, 0.2 mmol) in THF (1 mL), heated to 20° C. and stirred for 1 h at 40° C. Then the reaction mixture is combined with dimethylamine (3 mL, 6.0 mmol in THF) and stirred for 30 min at 135° C. in the microwave reactor. The solvent is eliminated, the residue is purified by prep. HPLC/MS (ACN/water, HCOOH as modifier) and example compound V-8 (10 mg, 15%; HPLC-MS: MS $(M+H)^+=542$; $t_{Ret.}=1.60$ min; method LCMSBAS1) is obtained.

Example compounds V-9 and V-10 are synthesised analogously to V-8 (Table 14).

Cyclisation Variant 5:

Method of synthesising 1-(3,4-difluoro-benzyl)-6-oxo-1,6-dihydro-pyrimidine-5-carboxylic acid {3-[2-(2-hydroxy-ethyl)-1-methyl-1H-imidazo[4,5-c]quinolin-8-yl]-prop-2-ynyl}-amide (V-11)

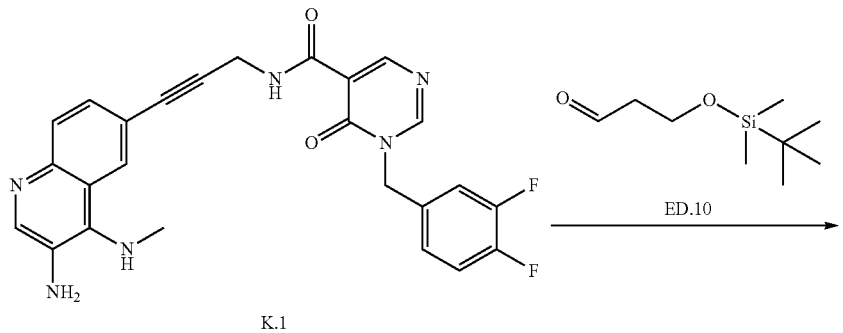

-continued

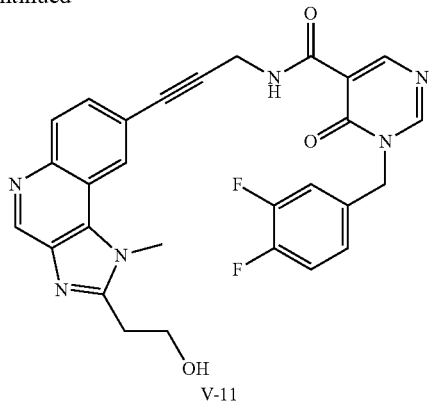
V-11

Diamine K.1 (70 mg, 0.2 mmol) and 3-[(tert-butyldimethylsilyl)oxy]-1-propanal ED.10 (18 mg, 0.1 mmol) are stirred for 1 h at 20° C. and for 1 h at 50° C. in DMF (2 mL). More ED.10 (15 mg, 0.1 mmol) and glacial acetic acid (30 µL) are added and the mixture is stirred for 18 h at 50° C. The reaction mixture is combined with glacial acetic acid (1 mL) and water (500 µL), stirred for 2 h at 65° C., the solvent is eliminated, the residue is purified by prep. HPLC/MS (ACN/water, HCOOH as modifier) and example compound V-11 (27 mg, 35%; HPLC-MS: MS (M+H)$^+$=527; $t_{Ret.}$=1.51 min; method LCMSBAS1) is obtained (Table 14).

TABLE 14

| # | Structure | MS (M + H)$^+$ | $t_{Ret.}$ HPLC [min] HPLC method |
|---|---|---|---|
| V-1 | 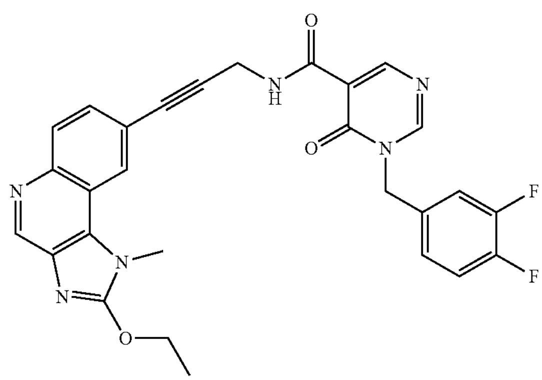 [SMILES: CCOc1nc2cnc3ccc(C#CCNC(=O)c4cncn(Cc5ccc(F)c(F)c5)c4=O)cc3c2n1C] | 529 | 1.76 LCMSBAS1 |
| V-2 | 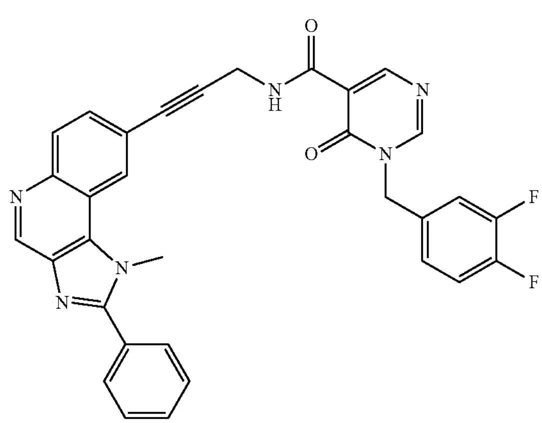 [SMILES: Cn1c(-c2ccccc2)nc2cnc3ccc(C#CCNC(=O)c4cncn(Cc5ccc(F)c(F)c5)c4=O)cc3c21] | 561 | 1.83 LCMSBAS1 |

TABLE 14-continued

| # | Structure | MS (M + H)+ | t_Ret. HPLC [min] HPLC method |
|---|---|---|---|
| V-3 | 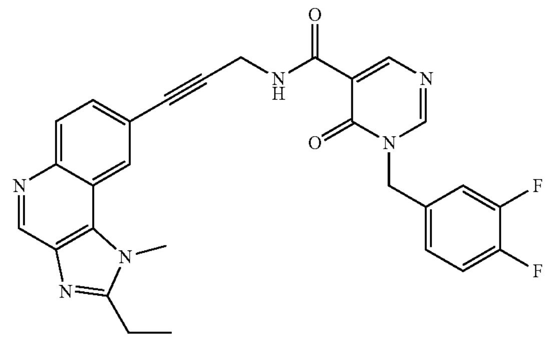 [SMILES: CCc1nc2cnc3ccc(C#CCNC(=O)c4cncn(Cc5ccc(F)c(F)c5)c4=O)cc3c2n1C] | 513 | 1.66 LCMSBAS1 |
| V-4 | 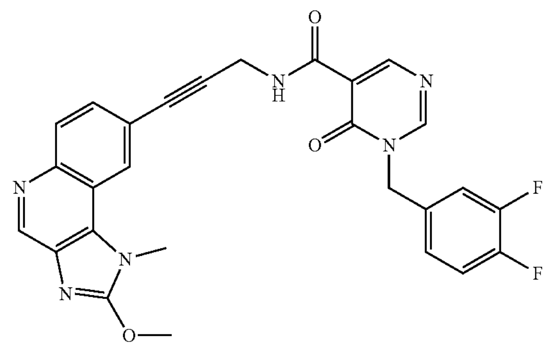 [SMILES: COc1nc2cnc3ccc(C#CCNC(=O)c4cncn(Cc5ccc(F)c(F)c5)c4=O)cc3c2n1C] | 515 | 1.68 LCMSBAS1 |
| V-5 | 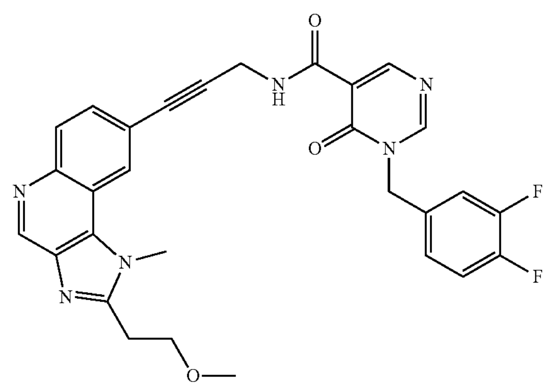 [SMILES: COCCc1nc2cnc3ccc(C#CCNC(=O)c4cncn(Cc5ccc(F)c(F)c5)c4=O)cc3c2n1C] | 543 | 1.65 LCMSBAS1 |
| V-6 | 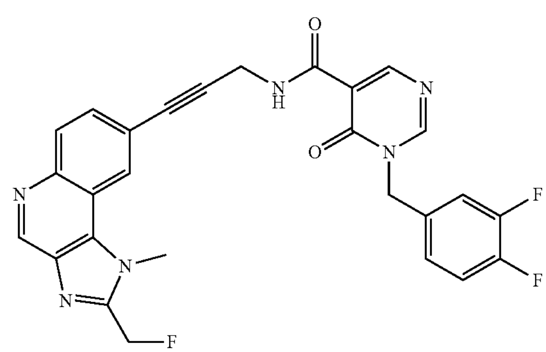 [SMILES: Cn1c(CF)nc2cnc3ccc(C#CCNC(=O)c4cncn(Cc5ccc(F)c(F)c5)c4=O)cc3c21] | 517 | 1.65 LCMSBAS1 |

TABLE 14-continued

| # | Structure | MS (M + H)+ | $t_{Ret.}$ HPLC [min] HPLC method |
|---|---|---|---|
| V-7 | 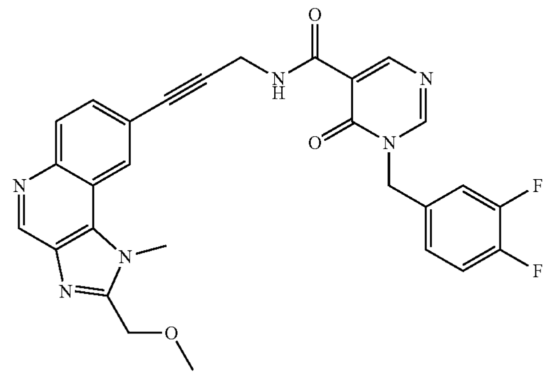 [SMILES: COCc1nc2cnc3ccc(C#CCNC(=O)c4cncn(Cc5ccc(F)c(F)c5)c4=O)cc3c2n1C] | 529 | 1.63 LCMSBAS1 |
| V-8 | 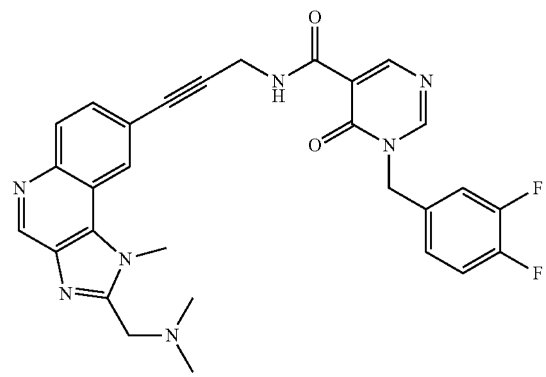 [SMILES: CN(C)Cc1nc2cnc3ccc(C#CCNC(=O)c4cncn(Cc5ccc(F)c(F)c5)c4=O)cc3c2n1C] | 542 | 1.60 LCMSBAS1 |
| V-9 | 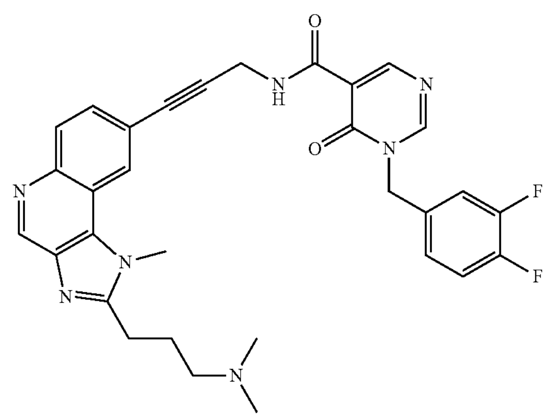 [SMILES: CN(C)CCCc1nc2cnc3ccc(C#CCNC(=O)c4cncn(Cc5ccc(F)c(F)c5)c4=O)cc3c2n1C] | 570 | 1.73 LCMSBAS1 |
| V-10 | 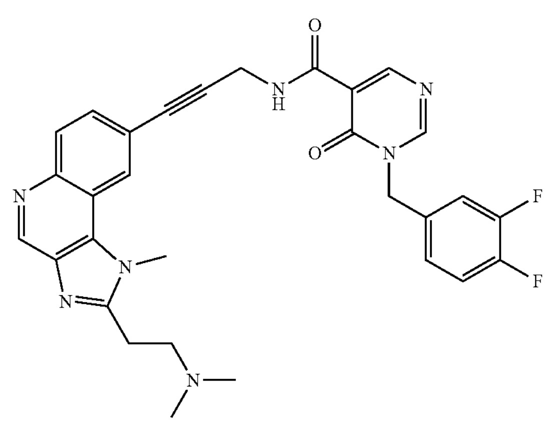 [SMILES: CN(C)CCc1nc2cnc3ccc(C#CCNC(=O)c4cncn(Cc5ccc(F)c(F)c5)c4=O)cc3c2n1C] | 556 | 1.65 LCMSBAS1 |

TABLE 14-continued

| # | Structure | MS (M + H)+ | $t_{Ret.}$ HPLC [min] HPLC method |
|---|---|---|---|
| V-11 | (structure) | 527 | 1.51 LCMSBAS1 |

The following Examples describe the biological activity of the compounds according to the invention, without restricting the invention to these Examples.

Compounds of general formula (1) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

The activity of the compounds according to the invention on the kinase PDK1 which inhibits the signal transduction pathway is determined in an in vitro kinase assay with recombinantly prepared protein:

PDK1 Kinase Assay

Recombinant human PDK1 enzyme (aa 52-556) linked at its N-terminal end to $His_6$ is isolated from baculovirus-infected insect cells. Purified enzyme may be obtained for example from the University of Dundee, Scotland. The following components are combined in a well of a 96-well round-based dish (Greiner bio-one, No. 650101):

1. 15 µL of compound to be tested in varying concentrations (e.g. starting at 10 µM, and diluted in steps of 1:5) in APT buffer (50 mM Tris/Cl pH7.5; 0.05% β-mercaptoethanol; 10 mM Mg-acetate; 0.0166% Tween 20; 3.33% DMSO)
2. 15 µL $His_6$-PDK1 (aa 52-556) 3.33 ng/well) and PDKtide (KTFCGTPEYLAPEVRRE PRILSEEEQEMFRDFDY-IADWC), synthesised by Pepceuticals Limited, Nottingham, United Kingdom; 25 µM final concentration); $His_6$-PDK1 and PDKtide are together diluted accordingly in assay buffer (50 mM tris pH 7.5, 0.05% β-mercaptoethanol, 10 mM Mg-acetate); PDKtide is present in this mixture as an 83.3 µM solution. These 30 µl are routinely incubated for 30 min at RT.
3. 20 µL ATP solution (25 µM ATP with 1.0 µCi/well gamma-P33-ATP). The final concentration of Tween 20 is 0.005%.

The reaction is started by adding the ATP solution and the mixture is incubated for 90 min at RT. At the start of the reaction the dishes are shaken gently. The reaction is stopped by the addition of 50 µL/well of 500 mM phosphoric acid ($H_3PO_4$) and incubated for about 20 min at RT. The precipitate is transferred by harvesting onto filter plates (96-well microtitre filter plate: UniFilter GF/C; Perkin Elmer; No. 6005174), then washed 6 times with 50 mM $H_3PO_4$ and dried at 60° C. Then the plate is stuck down with sealing tape, 25 µL/well of scintillation solution (Microscint 0; Perkin Elmer;

No. 6013611) are added and the amount of P33 precipitated is measured using the Wallac Betacounter. The measured data are evaluated using Graphpad Prism software.

Table 15 shows the $IC_{50}$ values of the example compounds determined using the above assay.

TABLE

| # | PDK1 $IC_{50}$ [nM] |
|---|---|
| I-1 | 1 |
| I-2 | 4 |
| I-3 | 4 |
| I-4 | 2 |
| I-5 | 50 |
| I-6 | 26 |
| I-7 | 18 |
| I-8 | 16 |
| I-9 | 10 |
| I-10 | 2 |
| I-11 | 11 |
| I-12 | 9 |
| I-13 | 16 |
| I-14 | 8 |
| I-15 | 28 |
| II-1 | 2 |
| II-2 | 8 |
| II-3 | 2 |
| II-4 | 5 |
| II-5 | 4 |
| II-6 | 1 |
| II-7 | 55 |
| II-8 | 507 |
| II-9 | 2 |
| II-10 | 2 |
| II-11 | 70 |
| II-12 | 5 |
| II-13 | 2 |
| II-14 | 34 |
| II-15 | 5 |
| II-16 | 5 |
| II-17 | 1 |
| II-18 | 14 |
| II-19 | 1 |
| II-20 | 2 |
| II-21 | 2 |
| II-22 | 16 |
| II-23 | 15 |
| II-24 | 590 |
| II-25 | 1015 |
| II-26 | 27 |
| II-27 | 1096 |
| II-28 | 221 |

TABLE-continued

| # | PDK1 IC$_{50}$ [nM] |
|---|---|
| II-29 | 202 |
| II-30 | 2 |
| II-31 | 8 |
| II-32 | 3 |
| II-33 | 13 |
| II-34 | 6 |
| II-35 | 7 |
| III-1 | 18 |
| III-2 | 2 |
| III-3 | 15 |
| III-4 | 21 |
| III-5 | 1 |
| III-6 | 2 |
| III-7 | 7 |
| III-8 | 2007 |
| III-9 | 4 |
| III-10 | 277 |
| III-11 | 18 |
| III-12 | 68 |
| III-13 | 53 |
| III-14 | 1 |
| III-15 | 20 |
| III-16 | 11 |
| III-17 | 111 |
| III-18 | 787 |
| III-19 | 45 |
| III-20 | 32 |
| III-21 | 5 |
| III-22 | 7 |
| III-23 | 1 |
| III-24 | 3 |
| III-25 | 4 |
| III-26 | 1 |
| III-27 | 3 |
| III-28 | 2 |
| III-29 | 681 |
| III-30 | 5 |
| III-31 | 1 |
| III-32 | 2 |
| III-33 | 2 |
| III-34 | 8 |
| IV-1 | 5 |
| V-1 | 33 |
| V-2 | 72 |
| V-3 | 8 |
| V-4 | 18 |
| V-5 | 24 |
| V-6 | 19 |
| V-7 | 41 |
| V-8 | 79 |
| V-9 | 6 |
| V-10 | 22 |
| V-11 | 14 |

The antiproliferative activity of the compounds according to the invention is determined in the proliferation test on cultivated human tumour cells and/or in a cell cycle analysis, for example on PC-3 tumour cells:

Inhibition of Proliferation on Cultivated Human Tumour Cells (PC-3)

To measure proliferation on prostate carcinoma tumour cell line PC-3 (obtained from American Type Culture Collection (ATCC)) the cells are cultivated in Ham's F12K (Gibco) and 10% foetal calf serum (Gibco) and harvested in the log growth phase. Then the PC-3 cells are placed in 96-well plates (Costar) at a density of 2000 cells per well and incubated overnight in an incubator (at 37° C. and 5% CO$_2$), wherein on each plate 16 wells are used as controls (8 wells with cells to which only DMSO solution has been added (should yield 30-50% maximum value of reduced AlamarBlue), 4 wells containing only medium (medium control, after the addition of oxidised AlamarBlue reagent the background signal is obtained) and 4 wells where again only medium is added (after the addition of reduced AlamarBlue reagent it acts as a maximum value)). The active substances are added to the cells in various concentrations (dissolved in DMSO; DMSO final concentration: 0.2%) (in each case as a double or triple measurement). After 5 d incubation 20 µl AlamarBlue reagent (Serotec) are added to each well, and the cells are incubated for a further 5-7 h. As a control, 20 µl reduced AlamarBlue reagent is added to each of 4 wells (AlamarBlue reagent which is autoclaved for 30 min). After incubation the colour change of the AlamarBlue reagent in the individual wells is determined in a SpectraMax Photometer (Molecular Devices) (extinction 530 nm, emission 590 nm, 5 measuring time). The amount of AlamarBlue reagent reacted represents the metabolic activity of the cells. The relative cell activity is calculated in relation to the control (PC-3 cells without inhibitor) and the active substance concentration which inhibits the cell activity by 50% (EC$_{50}$) is derived. The values are calculated from the average of two or three individual measurements.

Many of the compounds according to the invention cause inhibition of proliferation by interfering with intracellular signal transduction pathways which are important for cell survival, predominantly, but not exclusively, in cells which have become dependent on these signal pathways during their development.

Compounds (1) according to the invention generally demonstrate good activity in cell assays of this kind, i.e. for example an EC$_{50}$ value in the PC-3 proliferation test of less than 10 µmol/L, often less than 5 µmol/L.

Biomarker Inhibition:

The substances of the present invention bring about cellular inhibition of PDK1-substrates. Examples of the latter are Phospho-Thr308/AKT, Phospho-Ser221,227/RSK, or phosphorylation sites on p70S6 kinase (Thr229). In order to determine the inhibitory effect, the cells are treated with substance for 2 h, for example, lysed and analysed by Western Blot and/or BioPlex analysis for phosphoproteins of this kind. Commercially obtainable phospho-specific antibodies to the above-mentioned phosphorylation sites are used.

In PC-3 or other signal pathway-mutated cell lines as a rule EC$_{50}$ values of less than 5 µmol/L, often less than 0.5 µmol/L, are achieved with the present compounds on these phosphorylation sites compared with the carrier control and after standardisation to the corresponding whole protein.

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation or by aberrant activation of the phosphatidylinositol-3-kinase (PI3K)-PDK1-AKT signal pathway.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4,3-alethine, 131-I-TM-601, 3CPA, 7-ethyl-10-hydroxy-camptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992, BIBF 1120, bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-100, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PK1166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhuMAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, xeloda, XELOX, XL-281, XL-518/R-7420, YM-511, YM-598, ZD-4190, ZD-6474, ZD-4054, ZD-0473, ZD-6126, ZD-9331, ZD1839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:
Examples of Pharmaceutical Formulations

| A) | Tablets | per tablet |
|---|---|---|
| | active substance according to formula (1) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (1) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (1) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of the formula (1)

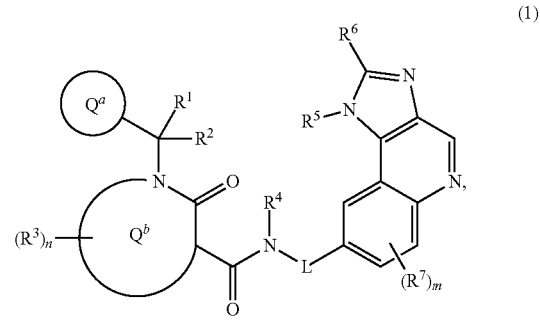

wherein
$Q^a$ is a ring system optionally substituted by one or more, identical or different $R^a$ and/or $R^b$, selected from among $C_{3-10}$cycloalkyl, $C_{6-10}$aryl, 5-12 membered heteroaryl and 3-14 membered heterocyclyl;
$R^1$ and $R^2$ are selected independently of one another from among hydrogen, halogen, $C_{1-4}$alkyl, $C_{2-4}$alkenyl, $C_{2-4}$alkynyl, $C_{1-4}$haloalkyl, —$NH_2$, —CN, —$NHC_{1-4}$alkyl, —$N(C_{1-4}$alkyl$)_2$, —OH, —$OC_{1-4}$alkyl, HO—$C_{1-4}$alkylene-, $C_{1-4}$alkyl-O—$C_{1-4}$alkylene-, $H_2N$—$C_{1-4}$alkylene-, —O—$C_{1-4}$haloalkyl, ($C_{1-4}$alkyl)NH—$C_{1-4}$alkylene- and ($C_{1-4}$alkyl$)_2N$—$C_{1-4}$alkylene-, wherein the alkyl, alkenyl, alkynyl and alkylene mentioned in the above groups may optionally be substituted by one or more identical or different halogen atoms;

the ring system $Q^b$ is

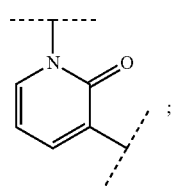

each $R^3$ is independently selected from among halogen, $C_{1-4}$alkyl, $C_{2-4}$alkenyl, $C_{2-4}$alkynyl, $C_{1-4}$haloalkyl, —NH$_2$, —CN, —N(C$_{1-4}$alkyl, —N(C$_{1-4}$alkyl)$_2$, —OH, —O—C$_{1-4}$alkyl, HO—C$_{1-4}$alkylene-, HO—C$_{2-4}$alkylene-O—, C$_{1-4}$alkyl-O—C$_{1-4}$alkylene-, C$_{1-4}$haloalkyl-O—C$_{1-4}$alkylene-, H$_2$N—C$_{1-4}$alkylene-, C$_{1-4}$alkyl-O—C$_{2-4}$alkylene-O—, (C$_{1-4}$alkyl)NH—C$_{1-4}$alkylene-, (C$_{1-4}$alkyl)$_2$N—C$_{1-4}$alkylene-, —OC$_{1-4}$haloalkyl, H$_2$N—C$_{2-4}$alkylene-O—, —NH(C$_{2-4}$alkylene-NH$_2$), —NH[C$_{2-4}$alkylene-NH(C$_{1-4}$alkyl)], NH[C$_{2-4}$alkylene-N(C$_{1-4}$alkyl)$_2$], (C$_{1-4}$alkyl)$_2$N—C$_{2-4}$alkylene-O—, (C$_{1-4}$haloalkyl)$_2$N—C$_{2-4}$alkylene-O—, (C$_{1-4}$haloalkyl)NH—C$_{2-4}$alkylene-O— and (C$_{1-4}$alkyl)NH—C$_{2-4}$alkylene-O—;

n denotes the number 0, 1, 2 or 3;
  wherein a group $R^3$ in the ring system $Q^b$-4 replaces a hydrogen in each case;
$R^4$ denotes hydrogen or $C_{1-4}$alkyl;
L denotes the group

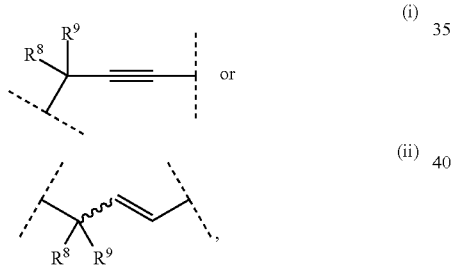

wherein
  the group —CR$^8$R$^9$— binds to the group —NR$^4$—, in case (ii) both a cis and a trans configuration may be present with respect to the double bond and
$R^8$ and $R^9$ are independently selected from among hydrogen, halogen, $C_{1-4}$alkyl and $C_{1-4}$haloalkyl;
$R^5$ is selected from among $R^a$ and $R^b$;
$R^6$ is selected from among $R^a$ and $R^b$;
each $R^7$ is independently selected from among $R^a$ and $R^b$;
m denotes the number 0, 1 or 2;
each $R^a$ independently denotes hydrogen or a group optionally substituted by one or more, identical or different $R^b$ and/or $R^c$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;
each $R^b$ is independently selected from among —OR$^c$, —NR$^c$R$^c$, halogen, —CN, —NO$_2$, —C(O)R$^c$, —C(O)OR$^c$, —C(O)NR$^c$R$^c$, —S(O)$_2$R$^c$, —S(O)$_2$NR$^c$R$^c$, —NHC(O)R$^c$ and —N(C$_{1-4}$alkyl)C(O)R$^c$ as well as the bivalent substituent =O, wherein the latter may only be a substituent in non-aromatic ring systems;

each $R^c$ independently denotes hydrogen or a group optionally substituted by one or more, identical or different $R^d$ and/or $R^e$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;
each $R^d$ is independently selected from among —OR$^e$, —NR$^e$R$^e$, halogen, —CN, —NO$_2$, —C(O)R$^e$, —C(O)OR$^e$, —C(O)NR$^e$R$^e$, —S(O)$_2$Re, —S(O)$_2$NR$^e$R$^e$, —NHC(O)R$^e$ and —N(C$_{1-4}$alkyl)C(O)R$^e$, as well as the bivalent substituent =O, wherein the latter may only be a substituent in non-aromatic ring systems;
each $R^e$ independently denotes hydrogen or a group optionally substituted by one or more, identical or different $R^f$ and/or $R^g$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;
each $R^f$ is independently selected from among —OR$^g$, —NR$^g$R$^g$, halogen, —CN, —NO$_2$, —C(O)R$^g$, —C(O)OR$^g$, —C(O)NR$^g$R$^g$, —S(O)$_2$R$^g$, —S(O)$_2$NR$^g$R$^g$, —NHC(O)R$^g$ and —N(C$_{1-4}$alkyl)C(O)R$^g$, as well as the bivalent substituent =O, wherein the latter may only be a substituent in non-aromatic ring systems and
each $R^g$ is independently selected from among hydrogen, $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;
wherein the compounds (1) may optionally also be present in the form of their tautomers, racemates, enantiomers, diastereomers or mixtures thereof or as the respective salts of all the above-mentioned forms.

2. The compound according to claim 1, wherein
$Q^a$ is a ring system optionally substituted by one or more, identical or different $R^a$ and/or $R^b$, selected from among $C_{5-6}$cycloalkyl, phenyl, 5-6 membered heteroaryl and 5-7 membered heterocyclyl, and
$R^a$ and $R^b$ are defined as in claim 1.

3. The compound according to claim 2, wherein
the ring system $Q^a$ optionally carries one or more identical or different substituents, selected from among halogen and $C_{1-4}$alkyl.

4. The compound according to claim 1, wherein
$R^1$ and $R^2$ are selected independently of one another from among hydrogen, $C_{1-4}$alkyl, $C_{2-4}$alkynyl, —CN, HO—C$_{1-4}$alkylene-, H$_2$N—C$_{1-4}$alkylene-, (C$_{1-4}$alkyl)NH—C$_{1-4}$alkylene-, (C$_{1-4}$halolkyl)NH—C$_{1-4}$alkylene-, (C$_{1-4}$alkyl)$_2$N—C$_{1-4}$alkylene- and (C$_{1-4}$haloalkyl)$_2$N—C$_{1-4}$alkylene-.

5. The compound according to claim 4, wherein
$R^1$ denotes hydrogen.

6. The compound according to claim 1, wherein
the ring system $Q^b$ is

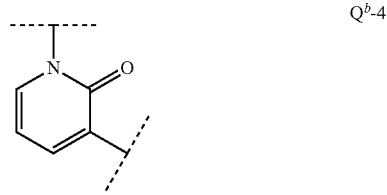

each $R^3$ is independently selected from among halogen, $C_{1-4}$alkyl, —OC$_{1-4}$alkyl, HO—C$_{1-4}$alkylene, C$_{1-4}$alkyl-O—C$_{1-4}$alkylene, —NH(C$_{2-4}$alkylene-NH$_2$), —NH[C$_{2-4}$alkylene-NH(C$_{1-4}$alkyl)] and —NH[C$_{2-4}$alkylene-N(C$_{1-4}$alkyl)$_2$];

n denotes the number 0, 1, 2 or 3,
wherein a group $R^3$ in the ring system $Q^b$-4 replaces a hydrogen in each case.

7. The compound according to claim 6, wherein the ring system $Q^b$ is

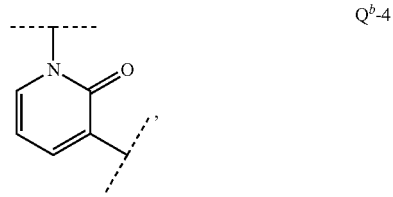

$Q^b$-4 and n has the value 0.

8. The compound according to claim 1, wherein $R^4$ denotes hydrogen or methyl.

9. The compound according to claim 1, wherein L denotes the group

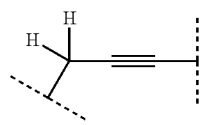

and the group —$CH_2$— binds to the group —$NR^4$—.

10. The compound according to claim 1, wherein $R^5$ is selected from among $R^{a1}$ and $R^{b1}$;

$R^{a1}$ denotes hydrogen or a group optionally substituted by one or more identical or different $R^{b1}$ and/or $R^{c1}$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^{b1}$ is independently selected from among —$OR^{c1}$, —$NR^{c1}R^{c1}$, halogen, —CN, —$NO_2$, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$ and —$N(C_{1-4}alkyl)C(O)R^{c1}$ as well as the bivalent substituent =O, wherein the latter may only be a substituent in non-aromatic ring systems;

each $R^{c1}$ independently denotes hydrogen or a group optionally substituted by one or more identical or different $R^{d1}$ and/or $R^{e1}$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^{d1}$ is independently selected from among —$OR^{e1}$, —$NR^{e1}R^{e1}$, halogen, —CN, —$NO_2$, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —$NHC(O)R^{e1}$ and —$N(C_{1-4}alkyl)C(O)R^{e1}$, as well as the bivalent substituent =O, wherein the latter may only be a substituent in non-aromatic ring systems;

each $R^{e1}$ independently denotes hydrogen or a group optionally substituted by one or more identical or different $R^{f1}$ and/or $R^{g1}$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^{f1}$ is independently selected from among —$OR^{g1}$, —$NR^{g1}R^{g1}$, halogen, —CN, —$NO_2$, —$C(O)R^{g1}$, —$C(O)OR^{g1}$, —$C(O)NR^{g1}R^{g1}$, —$S(O)_2R^{g1}$, —$S(O)_2NR^{g1}R^{g1}$, —$NHC(O)R^{g1}$ and —$N(C_{1-4}alkyl)C(O)R^{g1}$, as well as the bivalent substituent =O, wherein the latter may only be a substituent in non-aromatic ring systems and each $R^{g1}$ is independently selected from among hydrogen, $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl.

11. The compound according to claim 10, wherein $R^5$ is selected from among $R^{a1}$ and $R^{b1}$;

$R^{a1}$ denotes hydrogen or a group optionally substituted by one or more, identical or different $R^{b1}$ and/or $R^{c1}$, selected from among $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl;

each $R^{b1}$ is independently selected from among —$OR^{c1}$, —$NR^{c1}R^{c1}$, halogen, —CN, —$NO_2$, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$ and —$N(C_{1-4}alkyl)C(O)R^{c1}$ as well as the bivalent substituent =O, wherein the latter may only be a substituent in non-aromatic ring systems and each Rd is independently selected from among hydrogen, $C_{1-6}$alkyl, $C_{2-6}$alkenyl, $C_{2-6}$alkynyl, $C_{3-10}$cycloalkyl, $C_{6-10}$aryl, 5-12 membered heteroaryl and 3-14 membered heterocyclyl.

12. The compound according to claim 11, wherein $R^5$ is selected from among $R^{a1}$ and $R^{b1}$;

$R^{a1}$ denotes hydrogen or a group optionally substituted by one or more, identical or different $R^{b1}$ and/or $R^{c1}$, selected from among $C_{1-6}$alkyl, $C_{3-10}$cycloalkyl and 3-14 membered heterocyclyl;

each $R^{b1}$ is independently selected from among —$OR^{c1}$ and —$NR^{c1}R^{c1}$ and each $R^{c1}$ is independently selected from among hydrogen, $C_{1-6}$alkyl and $C_{6-10}$aryl.

13. The compound according to claim 1, wherein $R^6$ is selected from among hydrogen, $C_{1-6}$alkyl, HO—$C_{1-4}$alkylene-, $C_{1-4}$alkyl-O—$C_{1-4}$alkylene-, $C_{1-6}$alkyl-O, phenyl, $C_{1-6}$haloalkyl, $H_2N$—$C_{1-4}$alkylene-, $(C_{1-4}alkyl)NH$—$C_{1-4}$alkylene- and $(C_{1-4}alkyl)_2N$—$C_{1-4}$alkylene-.

14. The compound according to claim 13, wherein $R^6$ is selected from among hydrogen and $C_{1-6}$alkyl.

15. The compound according to claim 1, wherein m has the value 0.

16. A compound according to claim 1 selected from

1-[(1R)-1-(3,4-difluorophenyl)ethyl]-N-[3-[2-methyl-1-(1-methylpiperidin-4-yl)imidazo[4,5-c]quinolin-8-yl]prop-2-ynyl]-2-oxopyridine-3-carboxamide;

1-[(1S)-1-(3,4-difluorophenyl)ethyl]-N-[3-(2-methyl-1-propan-2-ylimidazo[4,5-c]quinolin-8-yl)prop-2-ynyl]-2-oxopyridine-3-carboxamide;

1-[(3,4-difluorophenyl)methyl]-N-[3-[2-methyl-1-(1-methylpiperidin-4-yl)imidazo[4,5-c]quinolin-8-yl]prop-2-ynyl]-2-oxopyridine-3-carboxamide;

1-[(1R)-1-(3,4-difluorophenyl)ethyl]-N-[3-[1-[4-(dimethylamino)cyclohexyl]-2-methylimidazo[4,5-c]quinolin-8-yl]prop-2-ynyl]-2-oxopyridine-3-carboxamide;

1-[(1R)-2-amino-1-(3,4-difluorophenyl)ethyl]-N-[3-(2-methyl-1-propan-2-ylimidazo[4,5-c]quinolin-8-yl)prop-2-ynyl]-2-oxopyridine-3-carboxamide;

1-[(1R)-1-(3,4-difluorophenyl)ethyl]-N-[3-[1-[4-(dimethylamino)cyclohexyl]-2-methylimidazo[4,5-c]quinolin-8-yl]prop-2-ynyl]-2-oxopyridine-3-carboxamide;

1-[[(1S,4R)-3-bicyclo[2.2.1]heptanyl]methyl]-N-[3-(2-methyl-1-propan-2-ylimidazo[4,5-c]quinolin-8-yl)prop-2-ynyl]-2-oxopyridine-3-carboxamide;

1-[(1R)-1-(3-fluorophenyl)-2-hydroxyethyl]-N-[3-(2-methyl-1-propan-2-ylimidazo[4,5-c]quinolin-8-yl)prop-2-ynyl]-2-oxopyridine-3-carboxamide;

1-[(3,4-difluorophenyl)methyl]-2-oxo-N-[3-[1-(1-propan-2-ylpiperidin-4-yl)imidazo[4,5-c]quinolin-8-yl]prop-2-ynyl]pyridine-3-carboxamide;

1-[(3,4-difluorophenyl)methyl]-N-[3-[1-[(3S)-1-methylpyrrolidin-3-yl]imidazo[4,5-c]quinolin-8-yl]prop-2-ynyl]-2-oxopyridine-3-carboxamide;

1-[(3,4-difluorophenyl)methyl]-N-[3-[2-methyl-1-(1-propan-2-ylpiperidin-4-yl)imidazo[4,5-c]quinolin-8-yl]prop-2-ynyl]-2-oxopyridine-3-carboxamide;

N-[3-[1-[4-(dimethylamino)cyclohexyl]imidazo[4,5-c]quinolin-8-yl]prop-2-ynyl]-1-[(1R)-1-(3-fluorophenyl)-2-hydroxyethyl]-2-oxopyridine-3-carboxamide; and N-[3-[1-[4-(dimethylamino)cyclohexyl]-2-methylimidazo[4,5-c]quinolin-8-yl]prop-2-ynyl]-1-[(1R)-1-(3-fluorophenyl)-2-hydroxyethyl]-2-oxopyridine-3-carboxamide.

17. The compound of formula (1) according to claim 1 wherein the salt is a pharmaceutically acceptable salt.

18. A pharmaceutical composition comprising a therapeutically effective amount of a compound of the formula (1) according to claim 1—or a pharmaceutically acceptable salt thereof—in combination with a conventional excipient and/or carrier.

\* \* \* \* \*